(12) United States Patent
Daugharthy et al.

(10) Patent No.: US 11,718,874 B2
(45) Date of Patent: Aug. 8, 2023

(54) HYBRIDIZATION CHAIN REACTION METHODS FOR IN SITU MOLECULAR DETECTION

(71) Applicant: President and Fellows of Harvard College, Cambridge, MA (US)

(72) Inventors: Evan R. Daugharthy, Cambridge, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/170,751

(22) Filed: Oct. 25, 2018

(65) Prior Publication Data

US 2019/0218608 A1 Jul. 18, 2019

Related U.S. Application Data

(63) Continuation of application No. PCT/US2017/029333, filed on Apr. 25, 2017.

(60) Provisional application No. 62/326,959, filed on Apr. 25, 2016.

(51) Int. Cl.
| | |
|---|---|
| *C12Q 1/6876* | (2018.01) |
| *C12Q 1/682* | (2018.01) |
| *C12N 15/115* | (2010.01) |
| *C12Q 1/6806* | (2018.01) |
| *C12Q 1/6816* | (2018.01) |

(52) U.S. Cl.
CPC .......... *C12Q 1/6876* (2013.01); *C12N 15/115* (2013.01); *C12Q 1/682* (2013.01); *C12Q 1/6806* (2013.01); *C12Q 1/6816* (2013.01); *C12N 2310/16* (2013.01); *C12N 2320/10* (2013.01)

(58) Field of Classification Search
CPC .................................. C07H 21/00; C12Q 1/68
See application file for complete search history.

(56) References Cited

U.S. PATENT DOCUMENTS

| | | | |
|---|---|---|---|
| 4,123,610 A | 10/1978 | Summerton et al. | |
| 4,844,617 A | 7/1989 | Kelderman et al. | |
| 4,886,741 A | 12/1989 | Schwartz | |
| 4,981,985 A | 1/1991 | Kaplan et al. | |
| 5,151,189 A * | 9/1992 | Hu .................... | B01D 67/0093 204/464 |
| 5,424,413 A | 6/1995 | Hogan et al. | |
| 5,563,056 A | 10/1996 | Swan et al. | |
| 5,594,235 A | 1/1997 | Lee | |
| 5,635,352 A * | 6/1997 | Urdea .................. | C12Q 1/6813 435/808 |
| 5,695,940 A | 12/1997 | Drmanac et al. | |
| 5,830,708 A | 11/1998 | Naughton | |
| 5,834,758 A | 11/1998 | Trulson et al. | |
| 5,871,921 A * | 2/1999 | Landegren ........... | C12Q 1/6813 435/6.1 |
| 6,068,979 A | 5/2000 | Akhavan-Tafti | |
| 6,083,726 A * | 7/2000 | Mills, Jr. ............. | B01J 19/0046 435/6.11 |
| 6,194,148 B1 | 2/2001 | Hori et al. | |
| 6,232,067 B1 | 5/2001 | Hunkapiller et al. | |
| 6,306,597 B1 | 10/2001 | Macevicz | |
| 6,534,266 B1 | 3/2003 | Singer | |
| 6,586,176 B1 | 7/2003 | Trnovsky et al. | |
| 6,632,655 B1 * | 10/2003 | Mehta .................. | C12Q 1/6874 506/14 |
| 7,255,994 B2 | 8/2007 | Lao | |
| 7,323,305 B2 | 1/2008 | Leamon et al. | |
| 7,427,479 B2 | 9/2008 | Karger et al. | |
| 7,473,767 B2 | 1/2009 | Dimitrov | |
| 7,534,991 B2 | 5/2009 | Miller et al. | |
| 7,555,155 B2 | 6/2009 | Levenson et al. | |
| 7,655,898 B2 | 2/2010 | Miller | |
| 7,745,129 B1 | 6/2010 | Schatz | |
| 7,771,949 B2 | 8/2010 | Kramer | |
| 7,906,285 B2 | 3/2011 | Drmanac | |
| 7,910,304 B2 | 3/2011 | Drmanac | |
| 7,941,279 B2 | 5/2011 | Hwang et al. | |
| 7,989,166 B2 | 8/2011 | Koch et al. | |
| 8,013,134 B2 | 9/2011 | Fredriksson | |

(Continued)

FOREIGN PATENT DOCUMENTS

| | | |
|---|---|---|
| CN | 1580283 A | 2/2005 |
| CN | 1959384 A | 5/2007 |

(Continued)

OTHER PUBLICATIONS

Brown et al., Review Article : In situ Hybridization with Riboprobes : An Overview for Veterinary Pathologists. Veterinary Pathology 35 : 159-167 (Year: 1998).*

(Continued)

*Primary Examiner* — Ethan C Whisenant
(74) *Attorney, Agent, or Firm* — Banner & Witcoff, Ltd.

(57) ABSTRACT

The disclosure provides a method for detecting a target analyte in a biological sample including contacting the sample with one or more probe sets each comprising a primary probe and a linker, contacting the sample with an initiator sequence, contacting the sample with a plurality of fluorescent DNA hairpins, wherein the probe binds the target molecule, the linker connects the probe to the initiator sequence, and wherein the initiator sequence nucleates with the cognate hairpin and triggers self-assembly of tethered fluorescent amplification polymers, and detecting the target molecule by measuring fluorescent signal of the sample.

16 Claims, 28 Drawing Sheets

Specification includes a Sequence Listing.

(56) References Cited

U.S. PATENT DOCUMENTS

| | | |
|---|---|---|
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,329,404 B2 | 12/2012 | McKernan et al. |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,501,459 B2 | 8/2013 | Chen et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,946,389 B2 | 2/2015 | Gao et al. |
| 8,986,926 B2 | 3/2015 | Ferree et al. |
| 9,017,992 B2 | 4/2015 | Winther et al. |
| 9,201,063 B2 | 12/2015 | Sood et al. |
| 9,217,151 B2 | 12/2015 | Yin et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,896,720 B2 | 2/2018 | Raj et al. |
| 9,909,167 B2 | 3/2018 | Samusik et al. |
| 10,030,261 B2 | 7/2018 | Frisen et al. |
| 10,032,064 B2 | 7/2018 | Hoyt |
| 10,126,242 B2 | 11/2018 | Miller et al. |
| 10,138,509 B2 | 11/2018 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisen et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,844,426 B2 | 11/2020 | Daugharthy et al. |
| 10,872,679 B2 | 12/2020 | Cai et al. |
| 10,964,001 B2 | 3/2021 | Miller |
| 11,021,737 B2 | 6/2021 | Church et al. |
| 2002/0015952 A1 | 2/2002 | Anderson et al. |
| 2002/0029979 A1 | 3/2002 | Freund et al. |
| 2002/0155989 A1 | 10/2002 | Efimov et al. |
| 2002/0172950 A1* | 11/2002 | Kenny .................. C12Q 1/682 435/6.11 |
| 2003/0148335 A1 | 8/2003 | Shen et al. |
| 2003/0165852 A1 | 9/2003 | Schueler et al. |
| 2004/0077014 A1 | 4/2004 | Becker |
| 2004/0248144 A1 | 12/2004 | Mir |
| 2004/0259190 A1 | 12/2004 | Naughton |
| 2005/0064435 A1 | 3/2005 | Su et al. |
| 2005/0106629 A1 | 5/2005 | McGrath et al. |
| 2005/0147981 A1 | 7/2005 | Yamakawa et al. |
| 2005/0191687 A1* | 9/2005 | Wang .................. C12Q 1/682 435/6.11 |
| 2005/0233318 A1 | 10/2005 | Chee et al. |
| 2006/0024711 A1 | 2/2006 | Lapidus et al. |
| 2006/0077536 A1 | 4/2006 | Bromage et al. |
| 2006/0177833 A1 | 8/2006 | Brenner |
| 2006/0183107 A1* | 8/2006 | Melkonyan .......... C12Q 1/6869 435/5 |
| 2006/0216339 A1* | 9/2006 | Ambron ............... A61K 38/465 514/17.4 |
| 2006/0228733 A1* | 10/2006 | Pierce .................. C12Q 1/682 536/25.32 |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0190543 A1 | 8/2007 | Livak |
| 2007/0206275 A1 | 9/2007 | Hemmer et al. |
| 2007/0231823 A1* | 10/2007 | McKernan ........... C12Q 1/6837 435/6.11 |
| 2007/0292877 A1 | 12/2007 | Dimitrov |
| 2008/0050718 A1 | 2/2008 | Gesteland et al. |
| 2008/0176769 A1 | 7/2008 | Rank et al. |
| 2008/0269068 A1* | 10/2008 | Church ................ C12Q 1/6874 506/9 |
| 2009/0005259 A1 | 1/2009 | Drmanac |
| 2009/0105082 A1 | 4/2009 | Chetverin et al. |
| 2009/0208965 A1 | 8/2009 | Tafas et al. |
| 2009/0220968 A1* | 9/2009 | Issadore ................ B01L 7/52 435/6.11 |
| 2009/0246879 A1 | 10/2009 | Drmanac et al. |
| 2010/0009868 A1 | 1/2010 | Yan et al. |
| 2010/0047924 A1 | 2/2010 | Webster et al. |
| 2010/0049448 A1 | 2/2010 | Doyle et al. |
| 2010/0087325 A1 | 4/2010 | Buermann |
| 2010/0151472 A1* | 6/2010 | Nolan .................. C12Q 1/682 435/6.1 |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0033520 A1* | 2/2011 | Mather ................. A61P 31/00 424/445 |
| 2011/0086774 A1 | 4/2011 | Dunaway |
| 2011/0092376 A1 | 4/2011 | Colston, Jr. et al. |
| 2011/0104693 A1 | 5/2011 | Seligmann |
| 2011/0208040 A1* | 8/2011 | Carmi ................. A61K 49/126 600/431 |
| 2011/0223585 A1 | 9/2011 | Gullberg et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2012/0126142 A1 | 5/2012 | Matsui et al. |
| 2012/0252686 A1 | 10/2012 | Umbarger et al. |
| 2012/0270214 A1 | 10/2012 | Bernitz et al. |
| 2012/0330636 A1 | 12/2012 | Albou |
| 2013/0017229 A1 | 1/2013 | Mooney |
| 2013/0245096 A1 | 9/2013 | Abitbol |
| 2013/0288249 A1 | 10/2013 | Gullberg et al. |
| 2013/0323729 A1 | 12/2013 | Landegren et al. |
| 2014/0049632 A1 | 2/2014 | Hemmer |
| 2014/0087378 A1 | 3/2014 | Chatre et al. |
| 2014/0087427 A1 | 3/2014 | Bujnicki et al. |
| 2014/0200146 A1 | 7/2014 | Xie et al. |
| 2014/0220578 A1 | 8/2014 | Bohannon et al. |
| 2014/0220587 A1 | 8/2014 | Green, Jr. et al. |
| 2014/0270435 A1 | 9/2014 | Dunn |
| 2015/0004598 A1* | 1/2015 | Gao .................... C12Q 1/6841 435/6.11 |

(56) References Cited

U.S. PATENT DOCUMENTS

| | | |
|---|---|---|
| 2015/0133319 A1 | 5/2015 | Fu et al. |
| 2015/0267251 A1* | 9/2015 | Cai .............. C12Q 1/6841 |
| | | 506/26 |
| 2016/0002704 A1 | 1/2016 | Diehl et al. |
| 2016/0024555 A1 | 1/2016 | Church et al. |
| 2016/0108458 A1 | 4/2016 | Frei et al. |
| 2016/0253584 A1 | 9/2016 | Fodor et al. |
| 2016/0265046 A1 | 9/2016 | Zhang et al. |
| 2016/0289740 A1 | 10/2016 | Fu et al. |
| 2016/0305856 A1 | 10/2016 | Boyden et al. |
| 2016/0358326 A1 | 12/2016 | Sarachan et al. |
| 2016/0376642 A1 | 12/2016 | Landegren et al. |
| 2017/0009278 A1* | 1/2017 | Söderberg ........ G01N 33/54306 |
| 2017/0067096 A1 | 3/2017 | Wassie et al. |
| 2017/0081489 A1 | 3/2017 | Rodriques et al. |
| 2017/0010672 A1 | 4/2017 | Luo et al. |
| 2017/0176338 A1 | 6/2017 | Wu et al. |
| 2017/0212983 A1* | 7/2017 | Cai ...................... G16B 40/00 |
| 2017/0220733 A1 | 8/2017 | Zhuang et al. |
| 2017/0253918 A1 | 9/2017 | Kohman |
| 2017/0262984 A1 | 9/2017 | Barnes et al. |
| 2018/0010166 A1* | 1/2018 | Pierce .............. C12Q 1/6816 |
| 2018/0051322 A1* | 2/2018 | Church ............. C12Q 1/6869 |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0282787 A1* | 10/2018 | Walter .............. C12Q 1/6804 |
| 2019/0017106 A1 | 1/2019 | Frisen et al. |
| 2019/0032128 A1 | 1/2019 | Chen et al. |
| 2019/0119735 A1 | 4/2019 | Deisseroth et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2020/0010891 A1 | 1/2020 | Beechem et al. |
| 2020/0034347 A1 | 1/2020 | Selly |
| 2020/0090786 A1 | 3/2020 | Quiroz Zarate et al. |
| 2020/0140920 A1 | 5/2020 | Pierce et al. |
| 2020/0239946 A1 | 7/2020 | Dewal |
| 2020/0354782 A1 | 11/2020 | Dewal |
| 2021/0017587 A1 | 1/2021 | Cai et al. |
| 2021/0115504 A1 | 4/2021 | Cai et al. |

FOREIGN PATENT DOCUMENTS

| | | |
|---|---|---|
| CN | 101553306 A | 10/2009 |
| EP | 2878671 A1 | 6/2015 |
| JP | H04-268359 A | 9/1992 |
| JP | 2012-170337 A | 9/2012 |
| JP | 2014-513523 A | 6/2014 |
| KR | 20080003402 A | 1/2008 |
| WO | 9746704 A1 | 12/1997 |
| WO | 98/56955 A1 | 12/1998 |
| WO | 01/26708 A1 | 4/2001 |
| WO | 01/37266 A1 | 5/2001 |
| WO | 2003044229 A1 | 5/2003 |
| WO | 2004/104645 A2 | 12/2004 |
| WO | 2006/138257 A2 | 12/2006 |
| WO | 2007/001986 A2 | 1/2007 |
| WO | 2007076128 A2 | 7/2007 |
| WO | 2007086900 A2 | 8/2007 |
| WO | 2007/121489 A2 | 10/2007 |
| WO | 2007/123744 A2 | 11/2007 |
| WO | 2007/149696 A1 | 12/2007 |
| WO | 2008069973 A2 | 6/2008 |
| WO | 2008157696 A2 | 12/2008 |
| WO | 2009/046348 A1 | 4/2009 |
| WO | 2009046149 A1 | 4/2009 |
| WO | 2010080134 A1 | 7/2010 |
| WO | 2010/087325 A1 | 8/2010 |
| WO | 2010104533 A2 | 9/2010 |
| WO | 2011/143583 A1 | 11/2011 |
| WO | 2012005595 A2 | 1/2012 |
| WO | 2012/058638 A2 | 5/2012 |
| WO | 2012/110899 A2 | 8/2012 |
| WO | 2012150035 A1 | 11/2012 |
| WO | 2013/055995 A2 | 4/2013 |
| WO | 2013096851 A1 | 6/2013 |
| WO | 2014/048083 A1 | 4/2014 |
| WO | 2014/0163886 A1 | 10/2014 |
| WO | 2014/182528 A2 | 11/2014 |
| WO | WO 2014/182528 * | 11/2014 |
| WO | 2015/118029 A1 | 8/2015 |
| WO | 2015/127183 A2 | 8/2015 |
| WO | WO 2015/118029 * | 8/2015 |
| WO | 2016007839 A1 | 1/2016 |
| WO | 2016081740 A1 | 5/2016 |
| WO | 2017079382 A1 | 5/2017 |
| WO | 2017079406 A1 | 5/2017 |
| WO | 2017143155 A2 | 8/2017 |
| WO | 2017/161251 A1 | 9/2017 |

OTHER PUBLICATIONS

Choi et al., Programmable in situ amplification for multiplexed imaging of mRNA expression. Nature Biotechnology 28(11) : 1208 (Year: 2010).*

Choi & Love et al., Immuno-Hybridization Chain Reaction for Enhancing Detection of Individual Cytokine-Secreting Human Peripheral Mononuclear Cells. Analytical Chemistry 83 : 6890-6895 (Year: 2011).*

Hansen et al., Sensitive ligand-based protein quantification using immuno-PCR: A critical review of single-probe and proximity ligation assays. Biotechniques 56:217-228 (Year: 2014).*

Kuimelis et al., Cleavage properties of an oligonucleotide containing a bridged internucleotide 5-phosphorothioate RNA linkage. Nucleic Acids Research 23 (23) : 4753-4760 (Year: 1999).*

Mag et al., Synthesis and selective cleavage of an oligodeoxynucleotide containing a bridged internucleotide 5'-phosphorothioate linkage. Nucleic Acids Research 19(7) : 1437 (Year: 1991).*

Richardson et al., Experimental and Theoretical Studies of Light-to-Heat Conversion and Collective Heating Effects in Metal Nanoparticle Solutions. Nano Letters 9(3) : 1139-1146 (Year: 2009).*

Song et al., Hybridization chain reaction-based aptameric system for the highly selective and sensitive detection of protein. Analyst 137 : 1396 (Year: 2012).*

Srinivas et al., On the biophysics and kinetics of toehold-mediated DNA strand displacement. Nucleic Acids Research 41(22) : 10641-10658 (Year: 2013).*

Xiao et al., Single-step electronic detection of femtomolar DNA by target-induced strand displacement in an electrode-bound duplex PNAS 103(45) : 16677-16680 (Year: 2006).*

Zhang et al., Dynamic DNA nanotechnology using strand-displacement reactions. Nature Chemistry 3 : 103-113 (Year: 2011).*

Zhao et al., An electrochemical aptasensor based on hybridization chain reaction with enzyme-signal amplification for interferon-gamma detection. Biosensors and Bioelectronics 36 : 129-134 (Year: 2012).*

Choi et al., Next-Generation in Situ Hybridization Chain Reaction: Higher Gain, Lower Cost, Greater Durability. ACS Nano 8(5):4284 (Year: 2014).*

Ho et al., Sequencing by ligation variation with endonuclease V digestion and deoxyinosine containing query oligonucleotides. BMC Genomics 12:598 (Year: 2011).*

Jiang et al., Solar thermal polymerase chain reaction for smartphone-assisted molecular diagnostics. Scientific Reports 4:4137 (Year: 2014).*

Ju et al., Four-color DNA sequencing by synthesis using cleavable fluorescent nucleotide reversible terminators. PNAS 103(52) : 19635 (Year: 2006).*

Lubeck et al., Single-cell in situ RNA profiling by sequential hybridization. Nature Methods 11(4) : 36-361 (Year: 2014).*

Parinov et al., DNA sequencing by hybridization to microchip octa- and decanucleotides extended by stacked pentanucleotides. Nucleic Acids Research 24(15) : 2998 (Year: 1996).*

(56) References Cited

OTHER PUBLICATIONS

Schouten et al., Relative quantification of 40 nucleic acid sequences by multiplex ligation-dependent probe amplification. Nucleic Acids Research 30(12) : e57 (Year: 2002).*

Choi et al., Immuno-Hybridization Chain Reaction for Enhancing Detection of Individual Cytokine-Secreting Human Peripheral Mononuclear Cells. Analytical Chemistry 83:6890-6895 (Year: 2011).*

Lubeck et al., Single-cell in situ RNA profiling by sequential hybridization. Nature Methods 11(4) : 360-361 (Year: 2014).*

Choi et al.Supplementary Information from article published in Nature Biotechnology 28:1208-1212 (OCT) (Year: 2010).*

The International SNP Mapping Group. Nature 409 : 928 (Year: 2001).*

Eid et al., Science 232:133 (Year: 2009).*

Cao, Yi et al.," In-situ immuno-PCR to detect antigens," The Lancet, Sep. 16, 2000, pp. 1002-1003, vol. 356.

Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retreived from the Internet: URL:http://dspace.mit.edu/bitstream/handle/1721.1/107103/971494098-MIT.pdf?sequence=1 [retreived on Feb. 20, 2019].

Doillon et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.

Extended European Search Report dated May 13, 2019 for EP Application No. 16862929.3.

Extended European Search Report dated May 21, 2019 for European Application No. 16862945.9.

International Search Report and Written Opinion based on PCT/US2018/027583 dated Jun. 29, 2018.

Lee, Je Hyuk et al., "Fluorescent in situ sequencing (FISSEQ) or RNA for gene expression profiling in intact cells and tissues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.

Sano, Takeshi et al. "Immuno-PCR: Very Sensitive Antigen Detection by Means of Specific Antibody-DNA Conjugates," Science, Oct. 2, 1992, pp. 120-122, vol. 258.

Schweitzer, Barry et al., "Immunoassays with rolling circle DNA amplification: A versatile platform for ultrasensitive antigen detection" PNAS, Aug. 29, 2000, pp. 10113-10119, vol. 97, No. 18.

Soderberg, Ola et al.,"Direct observation of individual endogenous protein complexes in situ by proximity ligation," Nature Methods, Dec. 2006, pp. 995-1000, vol. 3, No. 12, Nature Publishing Group.

Choi, Harry M.T. et al., "Next-Generation in Situ Hybridization Chain Reaction: Higher Gain, Lower Cost, Greater Durability" ACS NANO, vol. 8, No. 5, May 27, 2014 (May 27, 2014), pp. 4284-4294, XP055409053, US.

Extended European Search Report issued for EP Application No. 17790240.0 dated Sep. 4, 2019.

Ravan, Hadi, et al. "Isothermal RNA detection through the formation of DNA concatemers contiaining HRP-mimicking DNAzymes on the surface of gold nanoparticles", Biosensors and Bioelectronics, Elsevier Science Ltd. UK, Amsterdam, NL, vol. 80, Jan. 18, 2016 (Jan. 18, 2016), pp. 67-73, XP029441324.

Zhou et al. "In Situ Detection of Messenger RNA Using Digoxigenin-Labeled Oligonucleotides and Rolling Circle Amplification" Experimental and Molecular Pathology 70, 281-288 (2001).

Chen et al., "Nanoscale imaging of RNA with expansion microscopy," Nature Methods, vol. 133, No. 8, pp. 679-684 (Aug. 1, 2016).

Chen et al., "Expansion microscopy," Science, vol. 347, No. 6221, pp. 543-548 (Jan. 30, 2015).

Chozinski et al., "Expansion microscopy with conventional antibodies and fluorescent proteins," Nature Methods, vol. 13, No. 6, pp. 485-488 (Jun. 1, 2016).

Amasino, "Acceleration of nucleic acid hybridization rate by polyethylene glycol," Analytical Biochemistry, vol. 152, No. 2, pp. 304-307 (Feb. 1, 1986).

Bouché et al., "The effect of spermidine on endonuclease inhibition by agarose contaminants," Analytical Biochemistry, vol. 115, No. 1, pp. 42-45 (Jul. 15, 1981).

Kuznetsova et al., "What Macromolecular Crowding Can Do to a Protein," Int J. Mol Sci., vol. 15, No. 12, pp. 23090-23140 (Dec. 1, 2014).

Oupicky et al., "Laterally stabilized complexes of DNA with linear reducible polycations: Strategy for triggered Intracellular actication of DNA delivery vectors," Journal of the American Chemical Society, vol. 124, No. 1, pp. 8-9 (Jan. 9, 2002).

Nguyen, Son C., "Strategies for Studying Chromatin Regulation and Organization," Doctoral Dissertation, Harvard University (May 1, 2018); retrieved from https://dash.harvard.edu/bitstream/handle/1/33493431/NGUYEN-DISSERTATION-2016.pdf?sequence=4&isAllowed=y on Apr. 8, 2020.

Clausson et al: "Compaction of rolling circle amplification products increases signal integrity and signal-to-noise ratio", Scientific Reports, vol. 5, Jul. 23, 2015 (Jul. 23, 2015), p. 12317, XP055305777, DOI: 10.1038/srep12317.

Ke et al: 11 In situ sequencing for RNA analysis in preserved tissue and cells 11 Nature Methods, vol. 10, No. 9, Jul. 14, 2013 (Jul. 14, 2013), pp. 857-860, XP055163946, ISSN: 1548-7091, DOI: 10.1038/nmeth.2563 * the whole document *.

Larsson, Chatarina; Grundberg, Ida; Sbderberg, Ola; Nilsson, Mats: 11 In situ detection and genotyping of individual mRNA molecules, Nature Methods, vol. 7, No. 5 Apr. 11, 2010 (Apr. 11, 2010), pp. 395-397, XP055035168, DOI: 10.1038/nmeth.1448 Retrieved from the Internet: URL:http://www.nature.com/nmeth/journal/v7/n5/pdf/nmeth.1448.pdf [retrieved on Aug. 9, 2012] * the whole document *.

Lee et al: "Highly Multiplexed Subcellular RNA Sequencing in Situ", Science, vol. 343, No. 6177, Feb. 27, 2014 (Feb. 27, 2014), pp. 1360-1363, XP055305772, us ISSN: 0036-8075, DOI: 10.1126/science.1250212.

Mitra R. D. et al: 11 In situ localized amplification and contact replication of many individual DNA molecules 11 Nucleic Acids Research, Information Retrieval Ltd, GB, vol. 27, No. 24, Dec. 15, 1999 (Dec. 15, 1999), p. e34, XP002292358, ISSN: 0305-1048, DOI: 10.1093/NAR/27.24.E34 * abstract *.

Nadji et al.,"Photochemically and Photoenzymatically Cleavable DNA," J. Am. Chem. Soc. 1992, 114, 9266-9269.

Nuovo: "Co-labeling Using In Situ PCR: A Review "Journal of Histochemistry & Cytochemistry, vol. 19, No. 11, Nov. 1, 2001 (Nov. 1, 2001), pp. 1329-1339, XP055164942, ISSN: 0022-1554, DOI: 10.1177/002215540104901101 * the whole document *.

Weibrecht, Irene et al., "Simultaneous Visualization of Both Signaling Cascade Activity and End-Point Gene Expression in Single Cells", Plos One, vol. 6, No. 5, May 25, 2011 (May 25, 2011).

Wright et al., "Dynamic closed-loop system for focus tracking using a spatial light modulator and a deformable membrane mirror," Optics Express, vol. 14, No. 1, pp. 222-228 (Jan. 9, 2006).

Wang et al., "The method of axial drift compensation of laser differential confocal microscopy based on zero-tracking," Proc. of SPIE, vol. 9618, 96180X (2015).

Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.

Dec. 18, 2014 (PCT) International Preliminary Report—App PCT/US2013/044241.

Ascano, M et al. Identification of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.

Benner et al. "Gene Expression analysis by massively parallel signature sequencing (MPSS) on microbead arrays". Nature Biotechnology, vol. 18, pp. 630-634 (Jun. 31, 2000).

Brenner, et al. "Gene expression analysis by massively parallel signature sequencing (MPSS) on microbead arrays". Nature Biotechnology vol. 18, pp. 630-634 (2000) doi:10.1038/76469.

Eliscovich et al. mRNA on the move: The road to its biological destiny. Journal of Biological Chemistry, vol. 288, No. 28, pp. 20361-20368, Jul. 2013, in press May 2013 (Year: 2013).

(56) References Cited

OTHER PUBLICATIONS

Extended European Seach Report issued in corresponding European Application No. 12860433.7, dated Aug. 13, 2015.
Ginart, P et al. RNA Sequencing In Situ. Nat Biotechnol. Jun. 2014, vol. 32, No. 6; pp. 543-544; DOI: 10.1038/nbt.2921.
Grompe (1993) Nature Genetics DOI: 10.1038/ng1093-111.
Han et al. "Quantum-dot-tagged microbeads for multiplexed optical coding of biomolecules". Nature Biotechnology, vol. 19, 99. 631-635 (Jul. 31, 2001).
International Search Report and Written Opinion issued in corresponding International Application No. PCT/US2012/071398, dated Apr. 8, 2013.
Jambhekar et al. Cis-acting determinants of asymmetric, cytoplasmic RNA transport. RNA, vol. 13, pp. 625-642, 2007 (Year: 2007).
Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).
Lee, JH et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, first column, first paragraph; p. 1363, first column, second paragraph to second column, first paragraph; DOI: 10.1126/science.1250212.
Matlin et al. Spatial expression of the genome: the signal hypothesis at forty. Nature Reviews. Molecular Cell Biology, vol. 12, No. 5, pp. 333-340, May 2011, Epub Apr. 2011. (Year: 2011).
Meeks et al. Characterization of genes encoding poly(A) polymerases in plants: Evidence for duplication and functional specialization. PLoS ONE, vol. 4, No. 11, e8082, Nov. 2009, printed as pp. 1/10-10/10. (Year: 2009).
Office Action issued for corresponding European Patent Application No. 12780609.9, dated Sep. 23, 2015.
Polidoros et al. Rolling circle amplification-RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year: 2006).
Saliba, AE et al. Single-Cell RNA-Seq: Advances and Future Challenges. Nucleic Acids Res. Jul. 22, 2014, vol. 42, No. 14; pp. 8845-8860; DOI: 10.1093/nar/gku555.
Seo, et al. Four-color DNA sequencing by synthesis on a chip using photocleavable fluorescent nucleotides. Proceeding of the National Academy of Sciences, Apr. 2005, 102 (17) 5926-5931.
Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10 1126/SCIENCE.1117839.
Singer-Kruger et al. Here, there, everywhere. RNA Biology, vol. 11, No. 8, pp. 1031-1039, Aug. 2014. (Year: 2014).
Thisse et al. "High-Resolution in situ hybridization to whole-mount zebrafish embryos" 2008. Nature Protocols. vol. 3 No.1 pp. 59-69. Doi:10.1038/nprot.2007.514.
Thisse et al. 2008 Nature protocols vol. 3 No 1 pp. 59-69. Doi:10.1038/nprot.2007.514.
Tsaftaris et al. Isolation of three homologous AP1-like MADS-box genes in crocus (*Crocus sativus* L.) and characterization of their expression. Plant Science, vol. 166, No. 5, pp. 1235-1243, May 2004. (Year: 2004).
Weis et al. Protein targeting to subcellular organelles via mRNA localization. Biochimica et Biophysica Acta, vol. 1833, pp. 260-273, 2013, available online Apr. 2012 (Year: 2012).
Supplemental Material for Schweitzer et al. (PNAS 2000; 97(18):10113-10119) (Year: 2000).
Markaki et al. "Fluorescence In Situ Hybridization Applications for Super-Resolution 3D Structured Illumination Microscopy" Methods in Microbiology, Jan. 2013.
Achim et al. "High-throughput spatial mapping of single-cell RNA-seq data to tissue of origin" Nature Biotechnology, Apr. 13, 2015.

PI: Piezo Nano Positioning, 2008 (online), retrieved on Aug. 12, 2020, pp. 1-6 <https://www.pi-usa.us/fileadmin/user_upload/pi_us/files/product_datasheets/N725_Piezo_Focus_Positioner.pdf>.
Gusev et al. "Rolling Circle Amplification: A New Approach to Increase Sensitivity for Immunohistochemistry and Flow Cyometry" American Journal of Pathology, vol. 159, No. 1, Jul. 2001, pp. 63-69.
Pihlak et al. "Rapid genome sequencing with short universal tiling probes" Nature Biotechnology, vol. 26, No. 6, Jun. 2008, pp. 676-684.
Lizardi "Next-generation sequencing-by-hybridization" Nature Biotechnology, vol. 26, No. 6, Jun. 2008, pp. 649-650.
Mignardi et al. "Fourth-generation sequencing in the cell and the clinic" Genome Medicine, 2014, 6:31.
Terry R, Porreca G, McCarthy K, Church GM. 2008. Polonator Instrument http://www.polonator.org; Wayback Machine (Aug. 7, 2008) "Open, Affordable, Sequencing".
Terry R, Porreca G, McCarthy K, Church GM. 2008. Polonator Instrument http://www.polonator.org; Wayback Machine (Aug. 7, 2008) "The Vision".
Terry R, Porreca G, McCarthy K, Church GM. 2008. Polonator Instrument http://www.polonator.org; Wayback Machine (Aug. 7, 2008) "The Polonator Ecosystem".
Terry R, Porreca G, McCarthy K, Church GM. 2008. Polonator Instrument http://www.polonator.org; Wayback Machine (Aug. 7, 2008) "Instrument Overview".
Terry R, Porreca G, McCarthy K, Church GM. 2008. Polonator Instrument http://www.polonator.org; Wayback Machine (Aug. 7, 2008) "Protocols".
Terry R, Porreca G, McCarthy K, Church GM. 2008. Polonator Instrument http://www.polonator.org; Wayback Machine (Sep. 5, 2008) "PET (Paired End-Tag) Genomic Shotgun Library Construction Protocol".
Terry R, Porreca G, McCarthy K, Church GM. 2008. Polonator Instrument http://www.polonator.org; Wayback Machine (Sep. 5, 2008) "Emulsion PCR Protocol".
Terry R, Porreca G, McCarthy K, Church GM. 2008. Polonator Instrument http://www.polonator.org; Wayback Machine (Sep. 5, 2008) "Emulsion Breaking Protocol".
Terry R, Porreca G, McCarthy K, Church GM. 2008. Polonator Instrument http://www.polonator.org; Wayback Machine (Sep. 5, 2008) "Bead Enrichment Protocol".
Terry R, Porreca G, McCarthy K, Church GM. 2008. Polonator Instrument http://www.polonator.org; Wayback Machine (Sep. 5, 2008) "Bead Capping Protocol".
Terry R, Porreca G, McCarthy K, Church GM. 2008. Polonator Instrument http://www.polonator.org; Wayback Machine (Sep. 5, 2008) "Coverslip Aminosilanation and Arraying Protocol".
Terry R, Porreca G, McCarthy K, Church GM. 2008. Polonator Instrument http://www.polonator.org; Wayback Machine (Sep. 5, 2008) "Polony Sequence by Ligation Protocol".
Terry R, Porreca G, McCarthy K, Church GM. 2008. Polonator Instrument http://www.polonator.org; Wayback Machine (Jul. 5, 2008) "Polony Sequence Protocols".
Terry R, Porreca G, McCarthy K, Church GM. 2008. Polonator Instrument http://www.polonator.org; Wayback Machine (Sep. 5, 2008) "Help Wanted".
Terry R, Porreca G, McCarthy K, Church GM. 2008. Polonator Instrument http://www.polonator.org; Wayback Machine (Aug. 7, 2008) "Software".
Terry R, Porreca G, McCarthy K, Church GM. 2008. Polonator Instrument http://www.polonator.org; Wayback Machine (Aug. 7, 2008) "Reagent Kits".
Terry R, Porreca G, McCarthy K, Church GM. 2008. Polonator Instrument http://www.polonator.org; Wayback Machine (Sep. 5, 2008) "Run Kits".
Terry R, Porreca G, McCarthy K, Church GM. 2008. Polonator Instrument http://www.polonator.org; Wayback Machine (Sep. 5, 2008) "Paired-Leg Library Kits".
Terry R, Porreca G, McCarthy K, Church GM. 2008. Polonator Instrument http://www.polonator.org; Wayback Machine (Sep. 5, 2008) "Emulsion PCR/Bead Capping Kits".

(56) References Cited

OTHER PUBLICATIONS

Terry R, Porreca G, McCarthy K, Church GM. 2008. Polonator Instrument http://www.polonator.org; Wayback Machine (Sep. 5, 2008) "Enrichment Kits".
Terry R, Porreca G, McCarthy K, Church GM. 2008. Polonator Instrument http://www.polonator.org; Wayback Machine (Aug. 7, 2008) "Flow Cells".
Church GM. 2006. "Genomes for all" Sci Am 294: 46-54.
De Bakker PI, Yelensky R, Pe'er I, Gabriel SB, Daly MJ, Altshuler D. 2005. "Efficiency and power in genetic association studies" Nat Genet 37:1217-23.
Dixon AL, Liang L, Moffatt MF, Chen W, Heath S, Wong KC, Taylor J, Burnett E, Gut I, Farrall M, Lathrop GM, Xbecasis GR, Cookson WO. 2007. "A genome-wide association study of global gene expression" Nat Genet 39: 1202-7.
Emilsson V, Thorleifsson G, Zhang B, Leonardson AS, Zink F, Zhu J, Carlson S, Helgason A, Walters GB, Sunnarsdottir S, Mouy M, Steinthorsdottir V, Eiriksdottir GH, Bjornsdottir G, Reynisdottir I, Gudbjartsson D, Helgadottir A, Jonasdottir A, Jonasdottir A, Styrkarsdottir U, Gretarsdottir S, Magnusson KP, Stefansson H, Fossdal R, Kristjansson K, Gislason HG, Stefansson T, Leifsson BG, Thorsteinsdottir U, Lamb JR, Gulcher JR, Reitman ML, Kong A, Schadt EE, Stefansson K. 2008; "Genetics of gene expression and its effect on disease" Nature 452: 423-8.
Risch N, Merikangas K. 1996. "The future of genetic studies of complex human diseases" Science 273: 1516-7.
Schadt EE, Monks SA, Drake TA, Lusis AJ, Che N, Colinayo V, Ruff TG, Milligan SB, Lamb JR, Cavet G, Linsley PS, Mao M, Stoughton RB, Friend SH. 2003. "Genetics of gene expression surveyed in maize, mouse and man" Nature 422: 297-302.
Altshuler D, Daly MJ, Lander ES. 2008. "Genetic mapping in human disease" Science 322: 881-8.
Cookson W, Liang L, Abecasis G, Moffatt M, Lathrop M. 2009. "Mapping complex disease traits with global gene expression" Nat Rev Genet 10: 184-94.
International HapMap C. 2005. "A haplotype map of the human genome" Nature 437:1299-320. PMC ID: PMC1880871.
Klein RJ. 2007. "Power analysis for genome-wide association studies" BMC Genet 8: 58. PMC ID: PMC2042984.
Kwan T, Benovoy D, Dias C, Gurd S, Provencher C, Beaulieu P, Hudson TJ, Sladek R, Majewski J. 2008. "Genome-wide analysis of transcript isoform variation in humans" Nat Genet 40: 225-31.
McCarroll SA. 2008. "Extending genome-wide association studies to copy-number variation" Hum Mol Genet 17: R135-42.
Morley M, Moiony CM, Weber TM, Devlin JL, Ewens KG, Spielman RS, Cheung VG. 2004. "Genetic analysis of genome-wide variation in human gene expression" Nature 430: 743-7.
Schadt EE, Molony C, Chudin E, Hao K, Yang X, Lum PY, Kasarskis A, Zhang B, Wang S, Suver C, Zhu J, Millstein J, Sieberts S, Lamb J, GuhaThakurta D, Derry J, Storey JD, Avila-Campillo I, Kruger MJ, Johnson JM, Rohl CA, van Nas A, Mehrabian M, Drake TA, Lusis AJ, Smith RC, Guengerich FP, Strom SC, Schuetz E, Rushmore TH, Ulrich R. 2008. "Mapping the genetic architecture of gene expression in human liver" PLoS Biol 6: e107. PMC ID: PMC2365981.
Serre D, Gurd S, Ge B, Sladek R, Sinnett D, Harmsen E, Bibikova M, Chudin E, Barker DL, Dickinson T, Fan JB, Hudson TJ. 2008. "Differential allelic expression in the human genome: a robust approach to identify genetic and epigenetic cis-acting mechanisms regulating gene expression" PLoS Genet 4: e1000006. PMC ID: PMC2265535.
Ball MP, Li JB, Gao Y, Lee J, LeProust E, Park I-H, Xie B, Daley GQ, Church GM. 2009. "Targeted and whole-genome methylomics reveals gene-body signatures in human cell lines" Nat Biotechnol 27: 361-8.
Brenner S, Williams SR, Vermaas EH, Storck T, Moon K, McCollum C, Mao JI, Luo S, Kirchner JJ, Eletr S, DuBridge RB, Burcham T, Albrecht G. 2000. "In vitro cloning of complex mixtures of DNA on microbeads: physical separation of differentially expressed cDNAs" Proc Natl Acad Sci U S A 97: 1665-70. PMC ID: PMC26493.
Chiang DY, Getz G, Jaffe DB, O'Kelly MJ, Zhao X, Carter SL, Russ C, Nusbaum C, Meyerson M, Lander ES. 2009. "High-resolution mapping of copy-number alterations with massively parallel sequencing" Nat Methods 6: 99-103. PMC ID: PMC2630795.
Choy E, Yelensky R, Bonakdar S, Plenge RM, Saxena R, De Jager PL, Shaw SY, Wolfish CS, Slavik JM, Cotsapas C, Rivas M, Dermitzakis ET, Cahir-McFarland E, Kieff E, Hafler D, Daly MJ, Altshuler D. 2008. "Genetic analysis of human traits in vitro: drug response and gene expression in lymphoblastoid cell lines" PLoS Genet 4: e1000287. PMC ID: PMC2583954.
Christian AT, Pattee MS, Attix CM, Reed BE, Sorensen KJ, Tucker JD. 2001. "Detection of DNA point mutations and mRNA expression levels by rolling circle amplification in individual cells" Proc Natl Acad Sci U S A 98: 14238-43. PMC ID: PMC64666.
Church GM, Porreca GJ, Terry RC, Lares M. 2008. "High-Speed Imaging for DNA Sequencing" Biophotonics (<http://www.photonics.com/Content/ReadArticle.aspx?ArticleID=33989>).
Deng J, Shoemaker R, Xie B, Gore A, LeProust EM, Antosiewicz-Bourget J, Egli D, Maherali N, Park IH, Yu J, Daley GQ, Eggan K, Hochedlinger K, Thomson J, Wang W, Gao Y, Zhang K. 2009. "Targeted bisulfite sequencing reveals changes in DNA methylation associated with nuclear reprogramming" Nat Biotechnol 27: 353-60.
Eberwine J, Kacharmina JE, Andrews C, Miyashiro K, McIntosh T, Becker K, Barrett T, Hinkle D, Dent G, Marciano P. 2001 "mRna expression analysis of tissue sections and single cells" J Neurosci 21: 8310-4.
Kolb HC, Finn MG, B. SK. 2001. "Click Chemistry: Diverse Chemical Function from a Few Good Reactions" Angew. Chem. Int. 40: 2004-21.
Kwiatkowski M, Fredriksson S, Isaksson A, Nilsson M, Landegren U. 1999. "Inversion of in situ synthesized oligonucleotides: improved reagents for hybridization and primer extension in DNA microarrays" Nucleic Acids Res 27: 4710-4. PMC ID: PMC148770.
Li JB, Gao Y, Aach J, Zhang K, Kryukov GV, Xie B, Ahiford A, Yoon J-K, Rosenbaum AM, Wait-Zaranek A, LeProust E, Sunyaev S, Church GM. 2009. "Multiplex padlock capture and sequencing reveal human hypermutable CpG variations" Genome Res in press.
Mitra RD, Butty VL, Shendure J, Williams BR, Housman DE, Church GM. 2003. "Digital genotyping and haplotyping with polymerase colonies" Proc Natl Acad Sci U S A 100: 5926-31. PMC ID: PMC156303.
Pan X, Urban AE, Palejev D, Schulz V, Grubert F, Hu Y, Snyder M, Weissman SM. 2008. "A procedure for highly specific, sensitive, and unbiased whole-genome amplification" Proc Natl Acad Sci U S A 105: 15499-504. PMC ID: PMC2563063.
Stougaard M, Lohmann JS, Zajac M, Hamilton-Dutoit S, Koch J. 2007. "In situ detection of non-polyadenylated RNA molecules using Turtle Probes and target primed rolling circle PRINS" BMC Biotechnol 7: 69. PMC ID: PMC2203993.
Wang Z, Gerstein M, Snyder M. 2009. "RNA-Seq: a revolutionary tool for transcriptomics" Nat Rev Genet 10: 57-63.
Wu J, Zhang S, Meng Q, Cao H, Li Z, Li X, Shi S, Kim DH, Bi L, Turro NJ, Ju J. 2007. "3'-O-modified nucleotides as reversible terminators for pyrosequencing" Proc Natl Acad Sci U S A 104: 16462-7. PMC ID: PMC2034218.
Zhang K, Li JB, Gao Y, Egli D, Xie B, Deng J, Li Z, Lee J, Aach J, Leproust E, Eggan K, Church GM. 2009. "Digital RNA Allelotyping Reveals Tissue-specific and Allele-specific Gene Expression in Human" (submitted to Nature Methods).
Bakal C, Aach J, Church G, Perrimon N. 2007. "Quantitative morphological signatures define local signaling networks regulating cell morphology" Science 316: 1753-6.
Bang D, Church GM. 2008. "Gene synthesis by circular assembly amplification" Nat Methods 5: 37-9.
Bell J. 2004. "Predicting disease using genomics" Nature 429: 453-6.
Harris TD, Buzby PR, Babcock H, Beer E, Bowers J, Braslavsky I, Causey M, Colonell J, Dimeo J, Efcavitch JW, Giladi E, Gill J, Healy J, Jarosz M, Lapen D, Moulton K, Quake SR, Steinmann K, Thayer E, Tyurina A, Ward R, Weiss H, Xie Z. 2008. "Single-molecule DNA sequencing of a viral genome" Science 320: 106-9.

(56) References Cited

OTHER PUBLICATIONS

Kim JB, Porreca GJ, Song L, Greenway SC, Gorham JM, Church GM, Seidman CE, Seidman JG. 2007. "Polony multiplex analysis of gene expression (PMAGE) in mouse hypertrophic cardiomyopathy" Science 316: 1481-4.
Kurimoto K, Yabuta Y, Ohinata Y, Saitou M. 2007. "Global single-cell cDNA amplification to provide a template for representative high-density oligonucleotide microarray analysis" Nat Protoc 2: 739-52.
Li JB, Levanon EY, Yoon J-K, Aach J, Xie B, LeProust E, Zhang K, Gao Y, G.M. C. 2009. "Genome-wide Identification of Human RNA Editing Sites by Parallel DNA Capturing and Sequencing" Science in press.
Meng Q, Kim DH, Bai X, Bi L, Turro NJ, Ju J. 2006. "Design and synthesis of a photocleavable fluorescent nucleotide 3'-O-allyl-dGTP-PC-Bodipy-FL-510 as a reversible terminator for DNA sequencing by synthesis" J Org Chem 71: 3248-52.
Mitra RD, Shendure J, Olejnik J, Edyta Krzymanska O, Church GM. 2003. "Fluorescent in situ sequencing on polymerase colonies" Anal Biochem 320: 55-65.
Porreca GJ, Shendure J, Church GM. 2006. "Polony DNA sequencing" Curr Protoc Mol Biol Chapter 7: Unit 7 8.
Porreca GJ, Zhang K, Li JB, Xie B, Austin D, Vassallo SL, LeProust EM, Peck BJ, Emig CJ, Dahl F, Gao Y, Church GM, Shendure J. 2007. "Multiplex amplification of large sets of human exons" Nat Methods 4: 931-6.
Shendure J, Mitra RD, Varma C, Church GM. 2004. "Advanced sequencing technologies: methods and goals" Nat Rev Genet 5: 335-44.
Shendure JA, Porreca GJ, Church GM. 2008. "Overview of DNA sequencing strategies" Curr Protoc Mol Biol Chapter 7: Unit 7 1.
Tang F, Barbacioru C, Wang Y, Nordman E, Lee C, Xu N, Wang X, Bodeau J, Tuch BB, Siddiqui A, Lao K, Surani MA. 2009. "mRNA-Seq whole-transcriptome analysis of a single cell" Nat Methods 6: 377-82.
Vigneault F, Sismour AM, Church GM. 2008."Efficient microRNA capture and bar-coding via enzymatic oligonucleotide adenylation" Nat Methods 5: 777-9.
Zhang K, Martiny AC, Reppas NB, Barry KW, Malek J, Chisholm SW, Church GM. 2006. "Sequencing genomes from single cells by polymerase cloning" Nat Biotechnol 24: 680-6.
Zhang K, Zhu J, Shendure J, Porreca GJ, Aach JD, Mitra RD, Church GM. 2006. "Long-range polony haplotyping of individual human chromosome molecules" Nat Genet 38: 382-7.
Church et al.; Center for Casual Consequences of Variation (CCV) "An NHGRI Center for Excellence in Genomic Science" http://ccv.med.harvard.edu; Wayback Machine (Jul. 3, 2011).
Church et al.; Center for Casual Consequences of Variation (CCV) "Our four Specific Aims" http://ccv.med.harvard.edu/specific_aims.htm; Wayback Machine (Aug. 13, 2011).
Church; "Proposal for a Center for the determination of the Casual Transcriptional Consequences of Human Genetic Variation (CTCHGV)" http://ccv.med.harvard.edu/CEGS09_Complete_Proposal_minus_Admin_Sections.09May21.final.pdf; Wayback Machine (Aug. 13, 2011).
J. H. Lee, M.D. Ph.D. presentation entitled "Population-wide Tissue-specific Functional Analysis of Human iPS Cells Using Single-Cell In Situ Sequencing" George Church Laboratory, Wyss Institute for Biology Inspired Engineering, Harvard Medical School, Boston, Jan. 10, 2010.
Tillberg et al., "Protein-retention expansion microscopy of cells and tissues labeled using standard fluorescent proteins and antibodies," Nat Biotechnol., vol. 34, No. 9, pp. 987-992 (2016).
Goransson et al. "A single molecule array for digital targeted molecular analyses" Nucleic Acids Research, 2009, vol. 37, No. 1, e7, doi:10.1093/nar/gkn921.
Dirks et al. "Triggered amplificaiton by hybridization chain reaction" PNAS; Oct. 26, 2004; vol. 101, No. 43, pp. 15275-15278.
Lubeck et al. "Single cell systems biology by super-resolution imaging and combinatorial labeling" Nature Methods; 9 (7); pp. 743-748; 2012.
Wang et al. "Rapid and Sensitive Detection of Severe Acute Respiratory Syndrome Coronavirus by Rolling Circle Amplification" Journal of Clinical Microbiology, vol. 43, No. 5, May 2005, pp. 2339-2344.
Bibikova et al. "Quantitative Gene Expression Profiling in Formalin-Fixed, Paraffin-Embedded Tissues Using Universal Bead Arrays" American Journal of Pathology, vol. 165, No. 5, Nov. 2004.
Capodieci et al. "Gene expression profiling in single cells within tissue" Nature Methods, Sep. 14, 2005, 2(9) pp. 663-665.
Conze et al. "Single molecule analysis of combinatorial splicing" Nucleic Acids Research, Jun. 29, 2010, vol. 38, No. 16; e163.
Femino et al. "Visualization of Single RNA Transcripts in Situ" Science, Apr. 24, 1998, vol. 280, pp. 585-590.
Gavrilovic et al. "Automated Classification of Multicolored Rolling Circle Products in Dual-Channel Wide-Field Fluroescence Microscopy" Cytometry Part A, Jul. 2011, 79(7), pp. 518-527.
Geiss et al. "Direct multiplexed measurement of gene expression with color-coded probe pairs" Nature Biotechnology, vol. 26, No. 3, Mar. 2008, pp. 317-325.
Gunderson et al. "Decoding Randomly Ordered DNA Arrays" Genome Research, May 2004, 14(5), pp. 870-877.
Han et al. "Quantum-dot-tagged microbeads for multiplexed optical coding of biomolecules" Nature Biotechnology, Jul. 2001, vol. 19, No. 7, pp. 631-635.
Itzkovitz et al. "Validating Transcripts with Probes and Imaging Technology" Nature Methods, Apr. 2011, 8(4 Suppl): S12-S19.
Itzkovitz et al. "Single molecule transcript counting of stem cell markers in the mouse intestine" Nat Cell Biol., Nov. 2011, 14(1), pp. 106-114.
Lagunavicius et al. "Novel application of Phi29 DNA polymerase: RNA detection and analysis in vitro and in situ by target RNA-primed RCA" RNA, May 2009, 15(5), pp. 765-771.
Larsson et al. "In situ detection and genotyping of individual mRNA molecules" Nature Methods, vol. 7, No. 5, May 2010, pp. 395-397.
Levsky et al. "Fluorescence in situ hybridization: past, present and future" Journal of Cell Science, Jul. 15, 2003, 116 (Pt 14), pp. 2833-2838.
Levsky et al. "Single-Cell Gene Expression Profiling" Science, Aug. 2, 2002, 297(5582), pp. 836-840.
Maierhofer et al. "Multicolor Deconvolution Microscopy of Thick Biological Specimens" American Journal of Pathology, vol. 162, No. 2, Feb. 2003, pp. 373-379.
Meade et al. "Multiplexed DNA detection using spectrally encoded porous" Analytical Chemistry, Apr. 1, 2009, 81(7), pp. 2618-2625.
Raj et al. "Imaging individual mRNA molecules using multiple singly labeled probes" Nature Methods, Oct. 2009, 5 (10), pp. 877-879.
Sun et al. "Composite Organic-Inorganic Nanoparticles as Raman Labels for Tissue Analysis" Nano Letters, Feb. 2007, vol. 7, No. 2, pp. 351-356.
Wahlby et al. "Sequential Immunofluorescence Staining and Image Analysis for Detection of Large Numbers of Antigens in Individual Cell Nuclei" Cytometry, Jan. 1, 2002, 47(1), pp. 32-41.
Weibrecht et al. "Simultaneous Visualization of Both Signaling Cascade Activity and End-Point Gene Expression in Single Cells" PLoS One, May 2011, vol. 6, Issue 5, e20148.
Wilson et al. "Encoded Microcarriers for High-Throughput Multiplexed Detection" Angewandte Chemie International Edition, Sep. 18, 2006, 45(37), pp. 6104-6117.
Zhao et al. "Advances of multiplex and high throughput biomolecular detection technologies based on encoding microparticles" Science China Chemistry, Aug. 2011, vol. 54, No. 8, pp. 1185-1201.
Leuchowius et al. "Parallel visualization of multiple protein complexes in individual cells in tumor tissue" Molecular & Cellular Proteomics; vol. 12; No. 6; pp. 1563-1571; Jun. 2013; published online Feb. 22, 2013.
Miarblestone et al. "Rosetta Brains: A strategy for molecularly-annotated connectomics" arXiv:1404.5103v1 -q-bio. NC], https://doi.org/10.48550/arXiv.1404.5103, pp. 1-18; Apr. 21, 2014.

(56) References Cited

OTHER PUBLICATIONS

Chen et al. "Functional organization of the human 4D Nucleome" PNAS, vol. 112, No. 26, Jun. 15, 2015, pp. 8002-8007.
Jarvius et al. "Digital quantification using amplified single-molecule detection" Nature Methods, vol. 3, No. 9, Sep. 2006, pp. 725-727.
Chen, et al. "Spatially resolved, highly multiplexed RNA profiling in single cells". Science. Apr. 24, 2015;348(6233): aaa6090, pp. 1-14.
Tam, et al. A microfluidic platform for correlative live-cell and super-resolution microscopy. PloS one. Dec. 29, 2014;9(12):e115512, pp. 1-20.
Bálint, et al. Correlative live-cell and superresolution microscopy reveals cargo transport dynamics at microtubule intersections. Proceedings of the National Academy of Sciences. Feb. 26, 2013;110(9): pp. 3375-3380.
Manders, et al. Direct imaging of DNA in living cells reveals the dynamics of chromosome formation. The Journal of cell biology. Mar. 8, 1999;144(5):813-822.
Douse et al. "Multiplexed and Reiterative Fluorescence Labeling via DNA Circuitry" Bioconjug Chem. Dec. 15, 2010;21 (12):2327-31. doi: 10.1021/bc100348q. Epub Nov. 16, 2010. (Supporting Information).
Douse et al. "Multiplexed and Reiterative Fluorescence Labeling via DNA Circuitry" Bioconjug Chem. Dec. 15, 2010;21 (12):2327-31. doi: 10.1021/bc100348q. Epub Nov. 16, 2010.
Muller et al. "Towards unlimited colors for fluorescence in-situ hybridization (FISH)" Chromosome Research; 10: 223-232, 2002.

\* cited by examiner

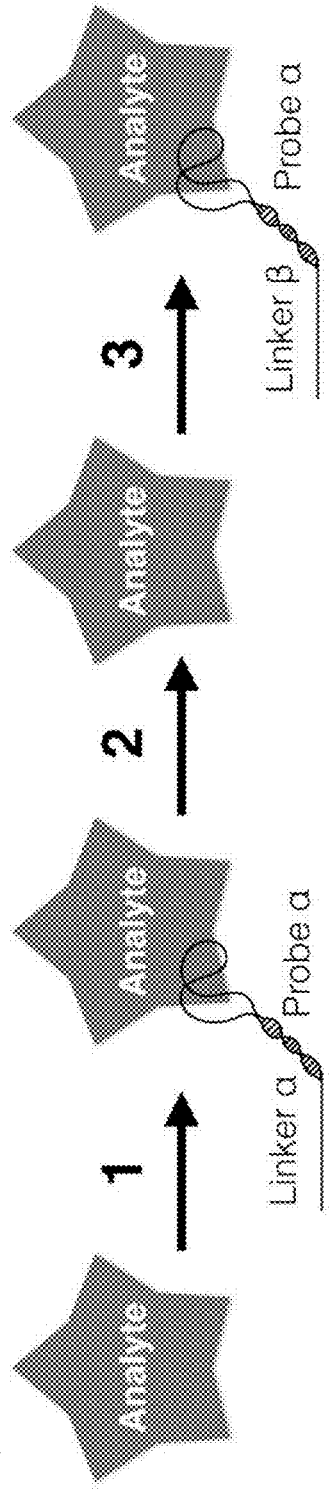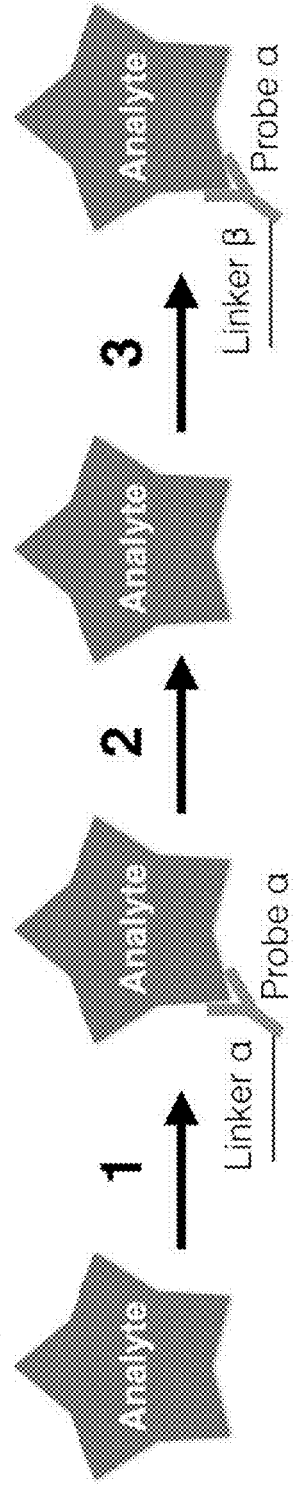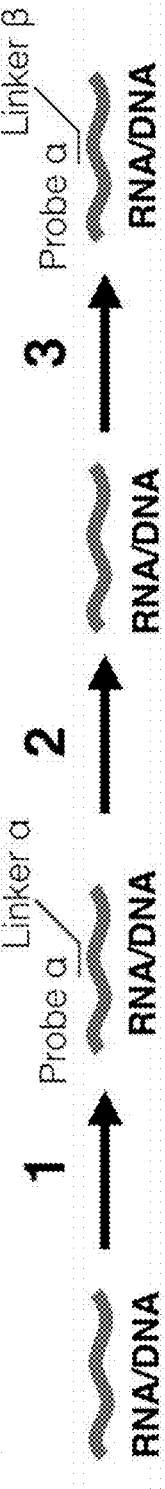

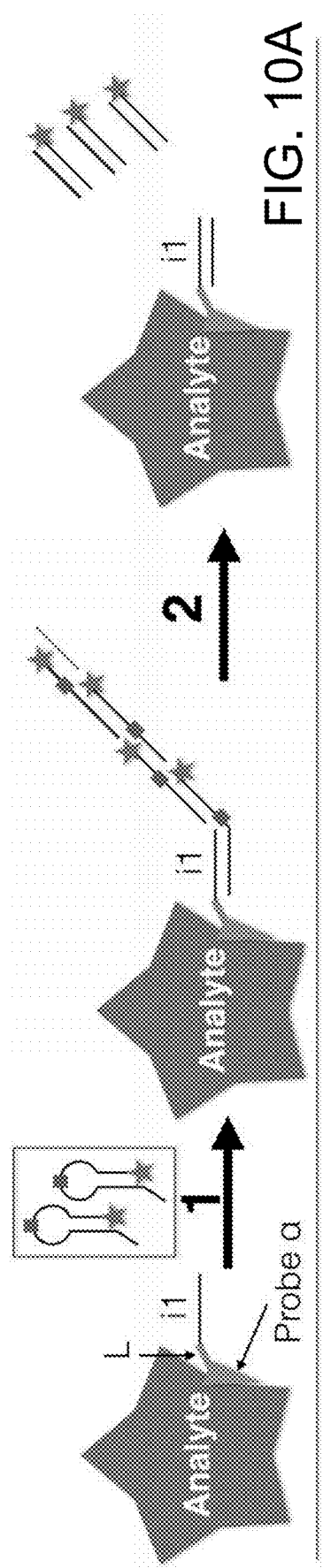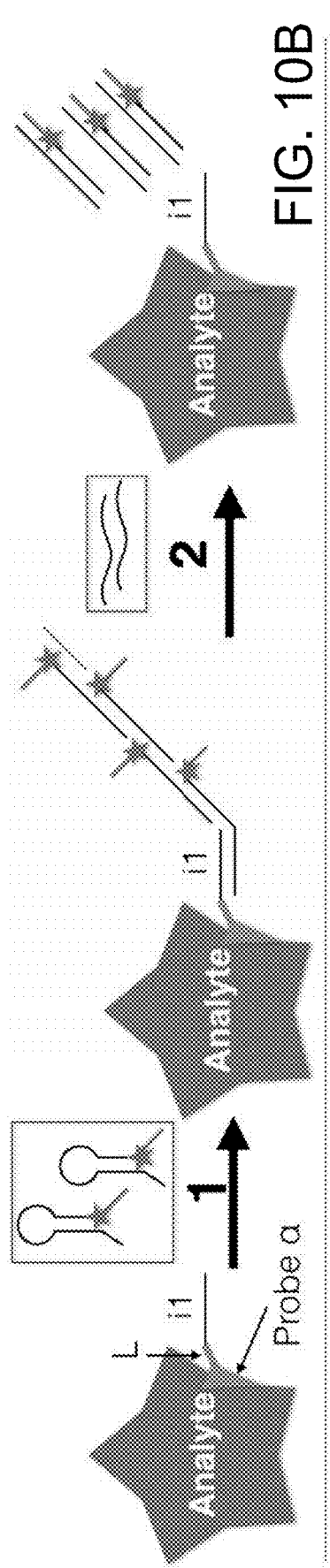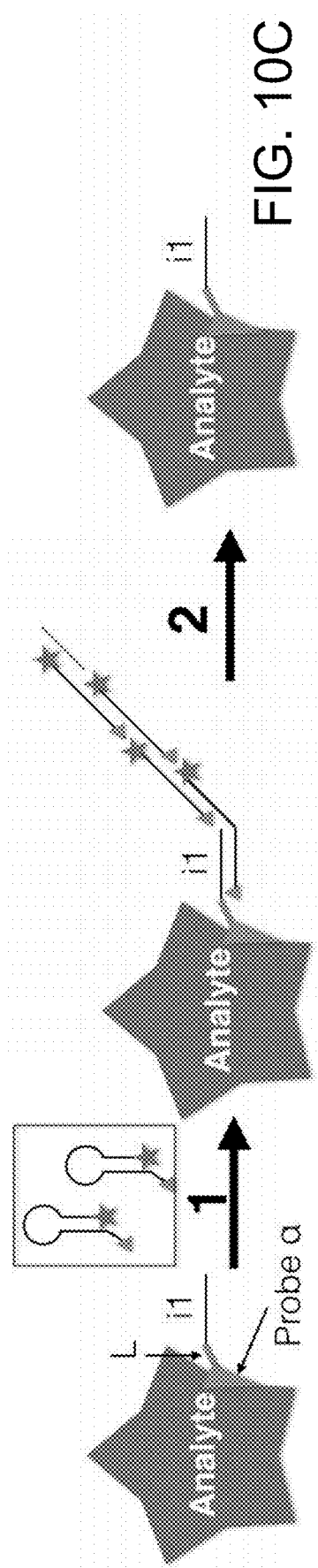

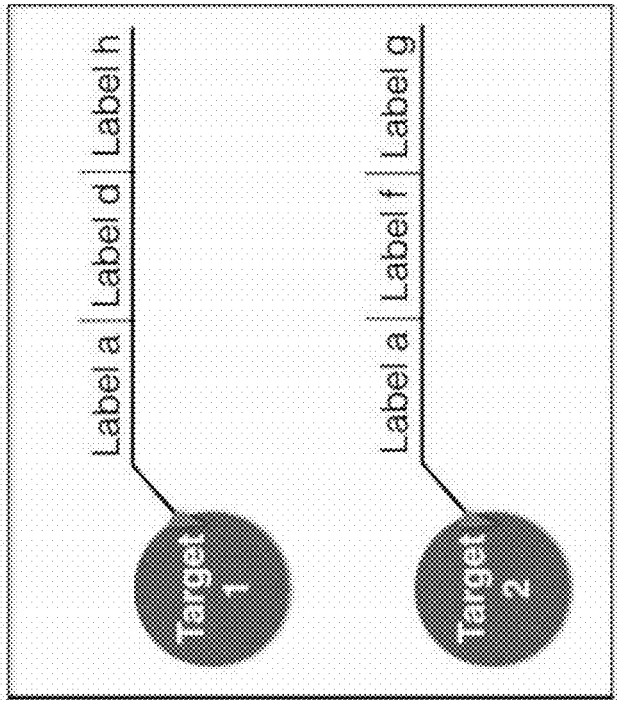
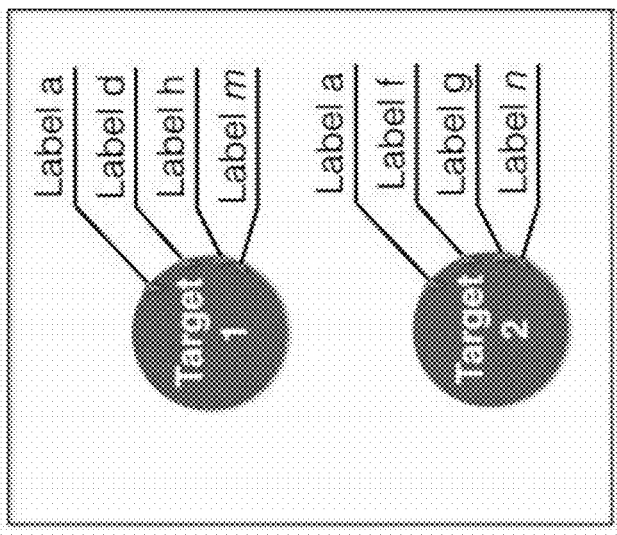

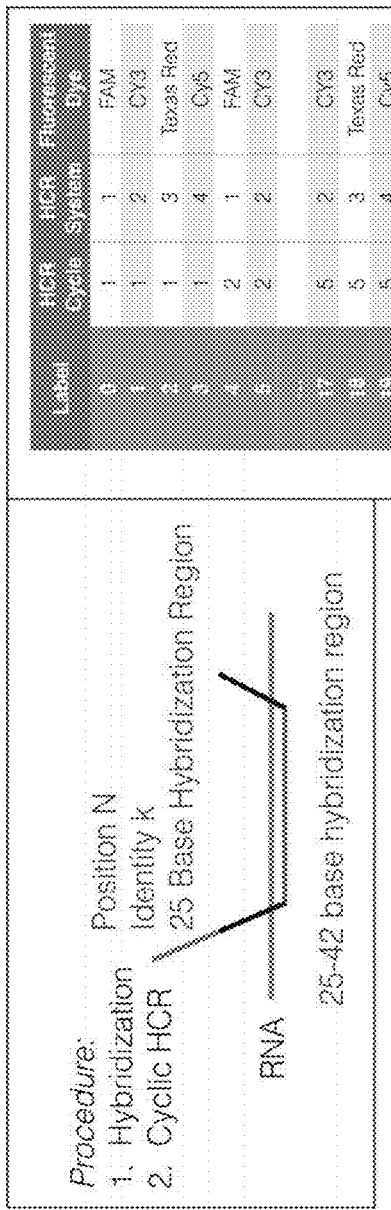
FIG. 18A
FIG. 18B
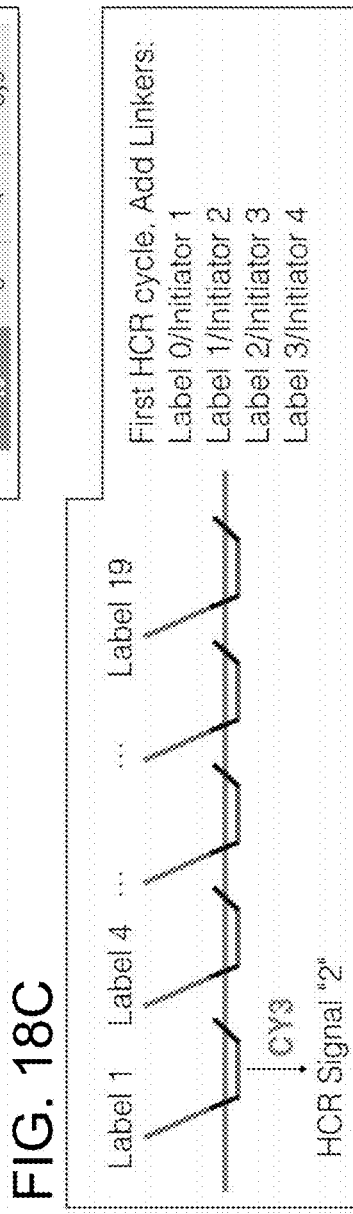
FIG. 18C
FIG. 18D

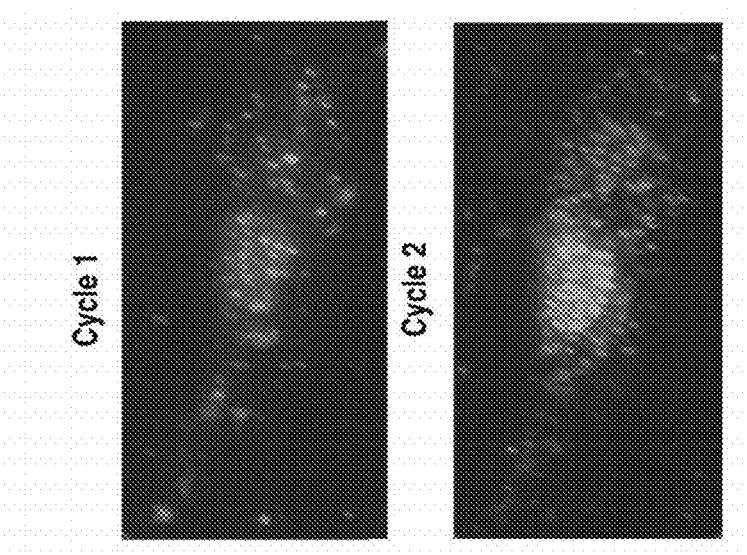
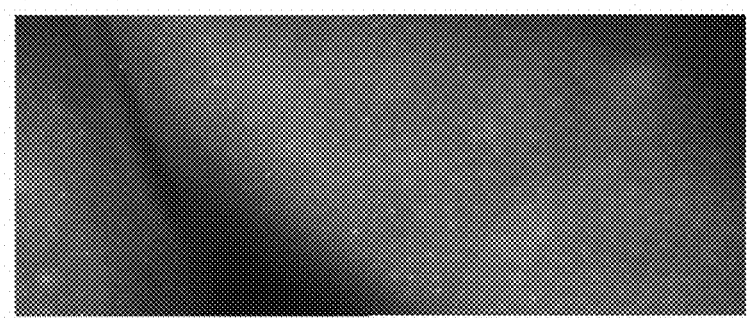
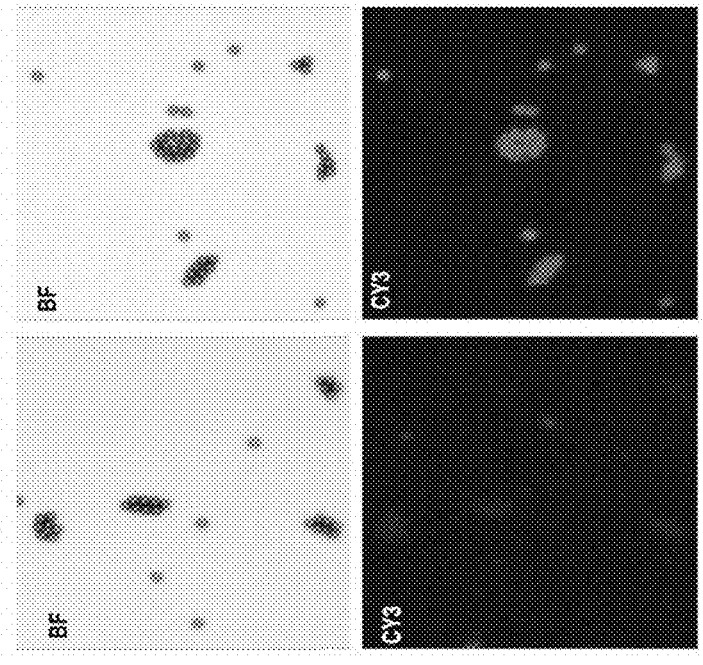

HYBRIDIZATION CHAIN REACTION METHODS FOR IN SITU MOLECULAR DETECTION

RELATED APPLICATION DATA

This application is a continuation application which claims priority to PCT Application PCT/US17/29333 designating the United States and filed Apr. 25, 2017; which claims the benefit of U.S. Provisional Application No. 62/326,959 and filed Apr. 25, 2016 each of which are hereby incorporated by reference in their entireties.

STATEMENT OF GOVERNMENT INTERESTS

This invention was made with government support under Grant No. DGE1144152 awarded by National Science Foundation and under Grant No. HG005550 awarded by National Institutes of Health. The government has certain rights in the invention.

BACKGROUND

A hybridization chain reaction method is described in Choi, Harry M T, Victor A. Beck, and Niles A. Pierce. "Next-generation in situ hybridization chain reaction: higher gain, lower cost, greater durability." *ACS nano* 8.5 (2014): 4284-4294. Other methods include those disclosed in US2005/0260635, US 2006/0228733, and U.S. Pat. No. 7,727,721.

SUMMARY

Embodiments of the present disclosure are directed to methods of using one or more or a plurality of probe sets based on the hybridization chain reaction ("HCR") for the identification and/or sequencing of one or more or a plurality of molecules in a sample, such as a biological sample. In general, hybridization chain reaction uses a nucleic acid initiator sequence, such as a DNA initiator sequence, and two or more or a plurality of metastable HCR monomers, which may take the form of a double stranded portion connected by a linker at one end of the double stranded portion and a single stranded sequence, such as a toe hold sequence, attached to one strand at the other end of the double stranded sequence. An exemplary metastable HCR monomer is a DNA hairpin with a toehold sequence. For ease of understanding, reference may be made to a hairpin sequence as exemplary of a metastable HCR monomer with the understanding that other metastable HCR monomers having a different structure may be used. The initiator sequence hybridizes to one strand of a first hairpin sequence causing the first hairpin sequence to open leaving a single stranded labeled extension which can then hybridize with a second hairpin sequence causing the second hairpin sequence to open leaving a single stranded extension which can then hybridize with a third hairpin sequence, etc., to form a polymer having a plurality of labels. Materials and methods regarding the use of the hybridization chain reaction are provided in US 2006/0228733 hereby incorporated by reference in its entirety.

Methods described herein incorporate hybridization chain reaction ("HCR") as a dynamic DNA-based sensing platform that can be used to read-out information encoded by the presence, abundance, and localization of initiator strand(s) of DNA or RNA, which trigger chain reaction of hybridization of nucleic acid molecules from a pool of stable or metastable, HCR monomers such as hairpins, which are generally understood herein to include a double stranded portion linked at one end by a linker or linker sequence. HCR amplifies the signal by increasing the number of detectable moieties, such as fluorophores, localized to the initiator strand. The initiator strand is said to be information encoding to the extent that initiator strands can be designed to be associated with a particular target molecule within a sample including a plurality of target molecules.

The disclosure provides hybridization chain reaction cycling strategies. Probe sets are used to create a plurality of HCR reactions, conducted in series, such as between 2 and 10 serial reactions, between 5 and 100 serial reactions, between 10 and 100 serial reactions, or between 20 and 100 serial reactions; or as sets of parallel reactions conducted in series, such as between 2 and 10 serial reaction sets, between 10 and 100 serial reaction sets, or between 20 and 100 serial reaction sets, of which each set of reactions contains between 2 and 4 HCR reactions, between 2 and 10 HCR reactions, between 2 and 20 HCR reactions, between 5 and 20 HCR reactions, or between 5 and 50 HCR reactions. These serial reactions or serial sets of parallel reactions can be used to achieve serial or combinatorial labeling of a plurality of analytes, such as between 10 and 1,000, between 10 and 10,000, between 100 and 1,000,000, between 500 and 100,000, or between 1,000 and 10,000 analytes. The disclosure provides methods of using sets of probes against a target analyte, whether modified or unmodified, using a schedule of serial probing events. The disclosure provides methods of programming the association between a probe against a target analyte and one or more HCR initiator sequences. The disclosure provides methods of programming the functionality of an HCR initiator sequence. The disclosure provides methods of using sets of HCR hairpins, whether modified or unmodified, for programmable assembly/disassembly of an HCR polymer. The disclosure provides methods of programming the association between an HCR polymer and a fluorescence signal.

Methods described herein incorporate features shown in FIGS. 1A-1C and as set forth in *ACS Nano* 8.5 (2014): 4284-4294 hereby incorporated by reference in its entirety. FIGS. 1A-1C depict in situ amplification via hybridization chain reaction (HCR). FIG. 1A depicts an HCR mechanism. Metastable fluorescent hairpins self-assemble into fluorescent amplification polymers upon detection of a cognate initiator. Initiator I1, comprised of single-stranded segments "b*-a*", nucleates with hairpin H1 via base-pairing to single-stranded toehold "a" of H1, mediating a branch migration that opens the hairpin to form complex I1·H1 containing single-stranded segment "c*-b*". This complex nucleates with hairpin H2 by means of base-pairing to single-stranded toehold "c", mediating a branch migration that opens the hairpin to form complex I1·H1·H2 containing single-stranded segment "b*-a*". Thus, the initiator sequence is regenerated, providing the basis for a chain reaction of alternating H1 and H2 polymerization steps. Red stars denote fluorophores. FIG. 1B depicts an in situ hybridization protocol. At the detection stage, probe sets including one or more or a plurality of initiator strands are hybridized to mRNA targets, and unused probes are washed from the sample. At the amplification stage using hybridization chain reaction by an initiator and a plurality of hairpins as described in FIG. 1A, initiators trigger self-assembly of tethered fluorescent amplification polymers from hairpins, and unused hairpins are washed from the sample. FIG. 1C depicts an experimental timeline. The same two-stage protocol is used independent of the number of target mRNAs.

For multiplexed experiments (three-color example depicted), probe sets for different target mRNAs (five probes depicted per set) carry orthogonal initiators that trigger orthogonal HCR amplification cascades labeled by spectrally distinct fluorophores.

An "HCR system," "HCR probe set," or "HCR initiator/hairpin set" include one or more initiator strands of nucleic acid together with one or more metastable HCR monomers, such as nucleic acid hairpins, that together are capable of forming the hybridization chain reaction polymer. According to methods described herein, an HCR system is designed using criteria to achieve the desired properties, such as orthogonality or non-reactivity with other nucleic acid species, as well as to have the desired kinetic and thermodynamic properties. The HCR system may be synthesized using standard methods, such as chemical nucleic acid synthesis, including commercial sources such as Integrated DNA Technologies (IDT, Coralville, Iowa), W. M. Keck Foundation Oligo Synthesis Resource (New Haven, Conn.), or Molecular Instruments (Pasadena, Calif.). Alternatively, the HCR system components may be synthesized and/or amplified using standard enzymatic methods, such as PCR followed by lambda exonuclease digestion of one strand to yield ssDNA, (see Current Protocols in Molecular Biology (2014): 14-23 hereby incorporated by reference in its entirety) or in vitro transcription followed by reverse transcription to yield ssDNA (see Science 348:6233 (2015): aaa6090 hereby incorporated by reference in its entirety.

Methods described herein utilizing features of hybridization chain reaction can be used for detecting one or more analytes or target molecules, such as for example within a biological sample (in situ), by designing of one or more or a plurality of HCR reactions, conducted in series, or as sets of parallel reactions conducted in series, for serial or combinatorial labeling of a plurality of target molecules, molecular identities, molecular qualities, or molecular compositions, such that each target is associated with a unique HCR signal or set of HCR signals over the totality of HCR reactions. Target molecules include nucleic acid polymers, such as RNA, DNA, and their analogs, amino acid polymers, including proteins, chemical modifications of any of the above, lipids, metabolites, biomolecules, and other small molecules, and molecular compositions including one or more of any of the above.

Target molecules or analytes are target by probes which may be connected to an initiator strand. The disclosure provides that the probe may be connected to the initiator strand by a linker. The disclosure provides that the initiator strand may be removable from the probe. The disclosure provides that the linker may be a cleavable linker. The disclosure provides that the linker may be formed from any binding pair of molecules which may bind together and be separated. The binding pair would connect the probe and the initiator strand such that the probe and the initiator would not be directly connected but would be indirectly connected through the binding pair of molecules.

Methods described herein allow rapid and isothermal amplification of a signal and detection of a diversity of analytes or target molecules in the same sample. Methods described herein include multiplexing by simultaneously using independent and orthogonal HCR systems to detect distinct analytes, multiplexing by simultaneously using independent and orthogonal HCR systems labeled with spectrally distinct dyes to detect distinct analytes, augmented space of spectrally distinct labels by combinatorial or colorimetric barcoding, as by simultaneously using one or more fluorophores per HCR system (see Science 297:836-840 (2002) hereby incorporated by reference in its entirety), specificity by using triggered probes that protect the initiators until the probes bind specifically to targets, reduced background by using self-quenching HCR system components with fluorophore/quencher pairs that become separated during assembly into amplification polymers, where unreacted HCR system components exhibit suppressed fluorescence, efficient penetration into a sample by using small HCR system components that diffuse rapidly and penetrate into a small-pore matrix such as a formaldehyde-fixed biological sample or polyacrylamide hydrogel, sensitive quantitative amplification by using nonlinear HCR mechanisms that offer exponential growth into polymers of a particular final size, and programmable amplification by using HCR systems exhibiting linear, quadratic, or exponential polymer growth.

Accordingly, methods described herein utilize target molecules or analytes which can be tracked for analysis as methods described herein utilize a cyclic method for analyzing such target molecules or analytes. That is, a particular target molecule or analyte is subjected to repeated or cyclic analysis using HCR as described herein and so is tracked in a manner that it is spectrally resolvable from other target molecules or analytes which may be in the same sample. One exemplary method of tracking a particular target molecule or analyte is by fixing the sample in a three dimensional matrix, so that each target molecule or analyte has a fixed known position within the matrix and can be subjected to repeated or cyclic HCR procedures as described herein wherein a signal resulting from HCR can be monitored and analyzed to produce time-ordered signals for the same or particular target molecule or analyte.

Methods described herein, such as repeated or cycling of certain method steps, advantageously overcome an upper limit on the number of orthogonal HCR systems associated with known systems. See ACS Nano 8.5 (2014):4284-4294. HCR has been known to be limited to five orthogonal DNA HCR probe sets. In order to be used simultaneously, the HCR probe sets must be non-reactive with each other, which is typically achieved by computationally designing the HCR probe sets simultaneously. This process may be computationally intensive, and scaling the number of simultaneously designed probe sets can dramatically increase the computational cost. In practice, growing the number of HCR probe sets comes at the cost of increased background and false-positive amplification, as the distance between probe sets in nucleic acid sequence space shrinks, given a nucleic acid sequence space defined by the size of the HCR system functional domains (e.g. an initiator domain and a propagation region). There may be other costs associated with engineering the HCR probes to be more specific by increasing the size of the nucleic acid sequence "design space", e.g. HCR probe sets with longer propagation regions may take significantly longer to polymerize.

Methods described herein advantageously overcome inherent barcoding limitations associated with known systems. If each HCR probe set is labeled with one of N spectrally distinct dyes, N analytes may be labeled simultaneously. If all combinatorial and single-color barcodes are used, the number of analytes labeled simultaneously is equal to $2^N-1$.

Biological systems exhibit enormous complexity in terms of molecular species, molecular qualities, and molecular configurations. Methods described herein can be used to simultaneously multiplex label a plurality of molecular species, molecular configurations, and molecular qualities, for the purpose of determining identity, abundance, and localization of molecules within biological systems, e.g. measuring the molecular configuration of biological systems. A certain property of the target analyte contains some "original information" regarding the existence, localization, abundance, number, identity, quality, configuration, or other property of the target, which is desired to be measured; where "information" is broadly considered to refer to what is conveyed or represented by the particular spatial and/or temporal arrangement of atoms, molecules, compounds, or molecular complexes, within a biological system, which is desired to be measured. During detection, this information or some fraction thereof is conveyed from the target analyte to a human or computer system via labeling and detection.

Given N orthogonal, independent, and spectrally distinct HCR systems, methods described herein provide greater multiplexity by using method steps of serial labeling of analytes for either linear or exponential barcoding. Linear Barcoding re-uses, (i.e. uses the same) N HCR systems serially k times to label k×N total analytes. This can be achieved by changing the association between the analyte and the HCR initiator between each round of HCR amplification and detection, such that each HCR initiator is associated with a different analyte during each round of HCR. Exponential barcoding re-uses (i.e. uses the same) N HCR systems serially k times to label $N^k$ total analytes. This can be achieved by changing the association between the analyte and the HCR initiator between each cycle of HCR amplification and detection, such that each analyte is associated with a number of HCR initiators over the totality of sequential HCR cycles (each analyte associated with between 0 and 1 HCR systems during each sequential cycle of HCR). Over the totality of HCR cycles, the combinatorial label associated with a target analyte is thereby constructed from the individual HCR signals within each cycle. In both cases, the relationship between the target analytes and the HCR reactions, which are understood to generate the detected fluorescence signals, is programmable, in that the HCR reactions are engineered over time to generate a coded set of fluorescence signals for the purpose of labeling analytes, such as those in situ. Collectively, this technology is referred to herein as cyclic HCR (CHCR), as steps within the overall labeling process can be cycled, i.e. occurring in a successive and recurring manner.

The disclosure provides methods and materials for "programming" the labeling cascade of HCR reaction including the steps of contacting the sample with a probe, contacting the sample with an HCR initiator sequence, contacting the sample with metastable HCR monomers, such as hairpins, and contacting the sample with fluorescent moieties, wherein the probe binds the target analyte, and wherein the HCR initiator sequence is associated with the probe, and wherein the initiator sequence nucleates with the cognate hairpin and triggers self-assembly of tethered amplification polymers, and wherein the tethered amplification polymer is associated with the fluorescent moieties, and wherein the target analyte is detected by measuring fluorescence of the sample.

The disclosure further provides methods and materials for "programming" the labeling cascade including the steps of contacting the sample with a probe, contacting the sample with an HCR initiator sequence, contacting the sample with metastable HCR monomers, such as hairpins, and contacting the sample with fluorescent moieties, wherein the probe binds the target analyte, and wherein the HCR initiator sequence is associated with the probe, and wherein the initiator sequence nucleates with the cognate hairpin and triggers self-assembly of tethered amplification polymers, and wherein the tethered amplification polymer is associated with the fluorescent moieties, and wherein the target analyte is detected by measuring fluorescence of the sample; and also including the steps of dissociating the fluorescent moieties from the HCR polymer and removing them, such as by washing, from the sample, of degrading or disassembling the HCR polymer and removing the constituent fragments from the sample, such as by washing, of dissociating or removing the HCR initiator sequence from the probe contacting the target analyte and removing it, such as by washing, from the sample, and/or of dissociating the probe from the target analyte and removing it, such as by washing, from the sample.

Cyclic HCR is enabled specifically by methods and materials to achieve programmability of each information transfer step. "Programmability" refers to the materials and methods enabling each step of the information transfer or labeling cascade to be either able to be gated, i.e. executed according to a pre-determined, discontinuous schedule, where the information transfer or labeling cascade is dependent upon one or more, or a plurality of inputs; or each step is able to be specifically reversed, i.e. where the information passed to a subsequent step in the labeling cascade is selectively deactivated, removed, destroyed or rendered undetectable, after being detected; or each step is able to be both gated and reversible. "Gated" as used herein may mean "inactive", "inhibited", "unable to proceed", and "ungated" as used herein may mean "active", "activated", "uninhibited", "able to proceed", and the like.

The disclosure provides a method for detecting a target analyte in a biological sample comprising the steps of: contacting the sample with a probe including an initiator sequence, contacting the sample with one or more, or a plurality of metastable fluorescent HCR monomers, such as hairpins, wherein the probe binds the target analyte, and wherein the initiator sequence nucleates with the cognate hairpin and triggers self-assembly of tethered fluorescent amplification polymers, and detecting the target analyte in the sample by measuring fluorescence of the sample. In one embodiment, a plurality of probes can be added for detecting multiple target analytes. In another embodiment, a plurality of metastable fluorescent hairpins having spectrally distinct fluorophores can be added for multiplexed detection. In one embodiment, the analyte comprises nucleic acid polymers including RNA, DNA and their analogs. In another embodiment, the analyte comprises amino acid polymers including proteins and chemical modifications thereof. In yet another embodiment, the analyte comprises lipids, metabolites, biomolecules, and other small molecules. In one embodiment, the initiator sequence is a DNA initiator sequence. In another embodiment, the method of the disclosure further comprises serial labeling of the analytes for either linear or exponential barcoding for multiplexed detection. In one embodiment, the method of the disclosure further comprises attaching a linker probe or secondary probe to the target analyte. In another embodiment, the linker probe or secondary probe binds to the probe including the initiator sequence. In certain embodiments, the initiator sequence is common or unique to the target analyte. In one embodiment, the probe is a triggered or activatable probe, such that the initiator sequence is protected or inhibited until the probe binds specifically to the target analyte, whereupon the initiator sequence is activated. In certain embodiments, a unique label associated with a target analyte is constructed from one or more, or a plurality of individual HCR signals using Cyclic HCR.

The disclosure further provides a method of in situ imaging comprising the steps of: contacting a biological sample with a probe, contacting the sample with an HCR initiator sequence that becomes associated with the probe, contacting the biological sample with a metastable HCR monomer(s) such as a hairpin(s), wherein the probe binds a target analyte in the biological sample, and wherein the HCR initiator sequence is associated with the probe, and wherein the initiator sequence nucleates with the cognate hairpin and triggers self-assembly of tethered amplification polymers, and wherein the tethered amplification polymer is associated with the fluorescent moieties, and wherein the target analyte is detected in the biological sample by measuring the fluorescence of the polymers.

In one embodiment, a plurality of probes can be added for imaging multiple target analytes. In another embodiment, a plurality of metastable fluorescent hairpins having spectrally distinct fluorophores can be added for multiplexed imaging. In another embodiment, the method of the disclosure further comprises serial labeling of the analytes for either linear or exponential barcoding for multiplexed detection. In one embodiment, the method of the disclosure further comprises attaching a linker probe or secondary probe to the target analyte wherein the linker probe or secondary probe is unique to the target analyte. In another embodiment, the linker probe or secondary probe binds to the probe comprising the initiator sequence. In certain embodiments, the initiator sequence is common or unique to the target analyte. In one embodiment, the probe is a triggered probe where the initiator sequence is protected or inhibited until the probe binds specifically to the target analyte whereupon the initiator sequence is activated. The method according to the present disclosure further comprises rounds of hybridization chain reaction "HCR" and detection cycles.

The disclosure provides a hybridization chain reaction "HCR" system including a probe including one or more nucleic acid initiator strands, and a metastable nucleic acid fluorescent HCR monomer such as a hairpin, wherein the initiator strand is capable of nucleating with the cognate hairpin and triggering self-assembly of HCR fluorescent polymers. In one embodiment, a plurality of probes are present for imaging multiple target analytes. In another embodiment, a plurality of metastable fluorescent hairpins having spectrally distinct fluorophores are present for multiplexed imaging. In one embodiment, the system is designed using criteria to achieve the desired properties, such as orthogonality or non-reactivity with other nucleic acid species, and to have the desired kinetic and thermal properties. In one embodiment, the hairpins can be generated by chemical and/or enzymatic synthesis. In some embodiments, rounds of hybridization chain reaction "HCR" and detection cycles can be performed. In one embodiment, the initiator and hairpin can be re-used. In another embodiment, the fluorescent signal can be programmatically generated and reset.

According to one aspect, the present disclosure provides a method for detecting one or more target analytes in a sample including contacting the sample with one or more probe sets wherein each probe set comprises one or more primary probes each cognate to a linker, and wherein each probe set is specific to a target analyte, contacting the sample with one or more hybridization chain reaction (HCR) initiators which bind to the linker, contacting the sample with one or more HCR amplifier systems, wherein each HCR amplifier system comprises two or more metastable HCR monomers, wherein at least one of the HCR monomers comprises a detectable label, wherein the primary probe binds the target analyte, wherein the linker connects the primary probe with the initiator, and wherein the initiator contacts the cognate HCR amplifier monomers and triggers hybridization chain reaction of self-assembled and tethered nucleic acid amplification polymer products, and wherein the detectable label is detected. In one embodiment, a plurality of probe sets each specific to a target analyte is designed for programmable and temporally ordered hybridization chain reactions. In another embodiment, the detectable label is fluorescent label and the totality of the temporally generated fluorescent signals provides a unique set of information for each target analyte including molecular identity, molecular quality, or molecular configuration. In one embodiment, the sample can be contacted with the probe set and the initiator simultaneously. In another embodiment, the HCR amplifier system is comprised of two metastable DNA hairpins. In one embodiment, the detectable label of the HCR amplifier system comprises spectrally distinct fluorescence signals for multiplexed detection. In another embodiment, the detectable label of the HCR amplifier system comprises a sequencing template for fluorescent sequencing by hybridization, fluorescent sequencing by ligation, or fluorescent sequencing by synthesis. In some embodiments, the target analytes comprise nucleic acid polymers including RNA, DNA and their analogs. In other embodiments, the target analytes comprise amino acid polymers including proteins and chemical modifications thereof. In some embodiments, the target analytes comprise lipids, metabolites, biomolecules, and other small molecules. In certain embodiments, the initiators comprise a nucleic acid hybridization chain reaction (HCR) initiation region. In one embodiment, the initiators comprise DNA. In some embodiments, the HCR amplifier monomers comprise metastable DNA double strands joined by a linker. In some embodiments, the target analytes are serially labeled. In one embodiment, the combined temporally ordered set of detected labels from the totality of cycles of HCR, wherein each cycle comprises detection of the detectable labels of one or more HCR systems, comprise a unique composite label for each target analyte. In another embodiment, the composite label comprises a linear or exponential barcode for multiplexed detection. In one embodiment, the unique composite label comprises a barcoded message. In another embodiment, the barcoded message further contains additional information including for error detection or error correction. In one embodiment, the design of a set of programmable and temporally ordered hybridization chain reactions and cognate fluorescent signals comprise a unique barcoded message for each target analyte. In one embodiment, cyclic HCR is enabled by the programmability of each information transfer step. The programmability refers to enabling each step of information transfer to be gated and or reversed. The gated information transfer refers to an execution according to a pre-determined, discontinuous schedule where the information transfer is dependent upon one or more inputs. In one embodiment, the binding of one or more primary probe sets to the target is repeated two or more times. In one embodiment, the primary probe and the linker are connected via covalent or non-covalent interactions. In another embodiment, the linker and the initiator are connected via covalent or non-covalent interactions. In one embodiment, the linker can be a bond or comprise a sequence portion that is complementary to a sequence portion of an oligonucleotide comprising an initiator sequence and hybridizes to the oligonucleotide comprising an initiator sequence. In another embodiment, the connection among the primary probe and the linker are programmably disrupted or reversed. In one embodiment, the connection among the linker and the initiator are programmably disrupted or reversed. In another embodiment, the linker comprises an initiator sequence cognate to a protecting group, which prevents the initiator from initiating HCR. In one embodiment, the initiator sequence is protected by a protecting oligonucleotide. In another embodiment, the protecting group is programmably disrupted from the linker, which allows the initiator to initiate HCR. In one embodiment, a de-protecting oligonucleotide can be introduced to remove the protecting oligonucleotide by toehold strand displacement. In another embodiment, the HCR polymer is degraded or disassembled after detecting the detectable label. In one embodiment, the connection among the HCR polymer and the detecting label is programmably disrupted or reversed after detection. In another embodiment, the binding of the primary probe to the target, and the connection among the primary probe, the linker, the initiator, the polymer, and the detecting moiety, can be programmably disrupted and reversed. In certain embodiments, the method further includes rounds of hybridization chain reaction "HCR" and detection cycles. In other embodiments, the method can be used for in situ imaging of a biological sample.

According to another aspect, the present disclosure provides a cyclic hybridization chain reaction "HCR" system including one or more probe sets wherein each probe set comprises one or more primary probes each cognate to a linker, and wherein each probe set is specific to a target analyte, an initiator, and one or more HCR amplifier systems, wherein each HCR amplifier system comprises two or more metastable HCR monomers, wherein at least one of the HCR monomers comprises a detectable label, wherein the initiator contacts the cognate HCR amplifier monomers and triggers hybridization chain reaction of self-assembled and tethered nucleic acid amplification polymer products, and wherein the detectable label is detected. In one embodiment, a plurality of probe sets each specific to a target analyte is designed for programmable and temporally ordered hybridization chain reactions. In another embodiment, the totality of the temporally generated fluorescent signals provides a unique set of information for each target analyte including molecular identity, molecular quality, or molecular configuration. In one embodiment, the HCR amplifier monomers are DNA hairpins. In another embodiment, the detectable label of the HCR amplifier monomers further comprises spectrally distinct fluorescent signals for multiplexed detection. In one embodiment, the system is designed using criteria to achieve the desired properties, such as orthogonality or non-reactivity with other nucleic acid species, and to have the desired kinetic and thermodynamic properties. In another embodiment, the HCR monomers can be generated by chemical and/or enzymatic synthesis. In one embodiment, non-fluorescent HCR monomers can be used. In another embodiment, the non-fluorescent HCR monomers are fluorescently labeled during or after the HCR polymerization stage. In one embodiment, the polymers formed from the non-fluorescent monomers are fluorescently labeled after the HCR polymerization stage. In another embodiment, the polymers formed from the non-fluorescent monomers are fluorescently labeled after the HCR polymerization stage by fluorescent sequencing by hybridization, fluorescent sequencing by ligation, or fluorescent sequencing by synthesis, by enzymatic reaction, or by chemical reaction. In certain embodiments, more than one round of hybridization chain reaction "HCR" and fluorescence detection can be performed. In other embodiments, the probes, linkers, initiators and HCR monomers can be re-used. In one embodiment, the linker is a nucleic acid sequence that is complementary to an oligonucleotide comprising an initiator. In another embodiment, the linker comprises a functional group for programmable disassociation from the initiator. In one embodiment, the linker comprises an initiator cognate to a protecting group, which prevents the initiator from initiating HCR. In another embodiment, the binding of the primary probe to the target, and the connection among the primary probe, the linker, the initiator, the polymers, and the detectable label can be disrupted and reversed during each round of hybridization chain reaction "HCR" and detection cycle to enable programmability of the system. In one embodiment, detection of the detectable label can be programmatically generated and reset. In another embodiment, the HCR amplifier monomers contain functional groups for programmable disassembly or degradation of the polymer. In one embodiment, the functional groups are comprised of toehold strand displacement sequences. In another embodiment, the functional groups comprise chemically labile, enzymatically labile, or photo-labile chemical groups. In certain embodiments, the probe binding to the target analyte is reversed by methods comprising chemical treatment, enzymatic treatment, DNase treatment of RNA ISH probes, exonuclease treatment of 5' phos ISH probes, nuclease treatment of nucleic acid probes, proteinase treatment of peptide probes, use of heat or denaturant to disrupt nucleic acid hybridization, use of heat or denaturant to disrupt aptamer binding, or use of heat or denaturant to disrupt bonding between antibody and protein. In one embodiment, the system comprises methods for programming HCR initiator functional linkage to bound probe. In another embodiment, the methods for programming HCR initiator functional linkage to bound probe comprise a) use of nucleic acid hybridization to add an initiator to a linker probe bearing a complementary nucleic acid molecule using sequencing by hybridization, b) use of an enzyme to add an initiator to a linker probe, c) use of heat or denaturant to disrupt nucleic acid hybridization to remove an initiator hybridized to a linker probe, d) use of toehold strand displacement to remove a protecting strand from an initiator that is localized to a target molecule via a linker probe, and e) incorporation of chemical, enzymatic, or photo-labile group between the initiator and linker probe, such that the initiator can be removed by chemical, enzymatic, or light treatments that disrupt the chemical linkage between the initiator and the linker probe. In one embodiment, the enzyme that adds the initiator to the linker probe is a DNA ligase that catalyzes a splint ligation reaction. In another embodiment, the system comprises methods for reversing a hybridization chain reaction. In one embodiment, the methods for reversing the hybridization chain reaction comprise a) using modified HCR monomers comprising one or more additional sequence for toehold strand displacement, such that addition of one or more complementary DNA strands will cause the HCR polymer to disassemble, and b) using modified HCR monomers comprising one or more enzymatic or chemical sensitive groups, or photo-labile groups in the DNA backbone of the HCR monomers, such that the HCR polymer can be fragmented or disrupted by chemical, enzymatic, or light treatments. In one embodiment, the system comprises methods for programming the functional generation of the HCR polymer fluorescent signal. In certain embodiments, the methods for programming the HCR polymer functional generation of fluorescent signal comprise a) using modified HCR monomers comprising additional sequence capable of being probed using sequencing by synthesis (SBS), sequencing by ligation (SBL), or sequencing by hybridization (SBH) to introduce fluorescent moieties to the HCR polymer, b) using modified HCR monomers comprising enzymatic, chemical, or photo-labile groups between the HCR DNA monomer backbone and fluorescent moieties, such that the fluorescent moieties can be removed by chemical, enzymatic, or light treatments, c) using modified fluorescent probes capable of labeling a HCR polymer such as by SBS, SBL, or SBH, wherein the fluorescent probes comprise additional sequence for toehold strand displacement such that the fluorescent probes can be removed from the HCR polymer by disrupting the hybridization between the fluorescent probes and the HCR polymer, and d) using modified fluorescent probes capable of labeling a HCR polymer such as by SBS, SBL, or SBH, wherein the fluorescent probes comprise enzymatic, chemical, or photo-labile groups between the HCR polymer backbone and fluorescent moieties, such that the fluorescent moieties can be removed by chemical, enzymatic, or light treatments.

According to one aspect, the present disclosure provides a method for detecting one or more target analytes in a biological sample in situ by hybridization chain reaction (HCR) including contacting the sample with one or more probe sets wherein each probe set comprises one or more primary probes each cognate to a linker, and wherein each probe set is specific to a target analyte, contacting the sample with one or more hybridization chain reaction (HCR) initiators, contacting the sample with one or more HCR amplifier systems, wherein each HCR amplifier system comprises two or more metastable HCR monomers, wherein at least one of the HCR monomers comprises a detectable label, wherein the primary probe binds the target analyte, wherein the linker connects the primary probe with the initiator, and wherein the initiator contacts the cognate HCR amplifier monomers and triggers hybridization chain reaction of self-assembled and tethered nucleic acid amplification polymer products, and wherein the detectable label is detected. In one embodiment, a plurality of probe sets each specific to a target analyte is designed for programmable and temporally ordered hybridization chain reactions. In another embodiment, the totality of the temporally generated fluorescent signals provides a unique set of information for each target analyte including molecular identity, molecular quality, or molecular configuration. In one embodiment, the sample can be contacted with the probe set and the initiator simultaneously. In another embodiment, the probe binding to the target analyte can be reversed so that the target analyte can be re-probed using hybridization chain reaction to amplify the signal. In certain embodiments, the probe binding to the target molecule is reversed by methods comprising chemical treatment, enzymatic treatment, DNase treatment of RNA ISH probes, exonuclease treatment of 5' phos ISH probes, nuclease treatment of nucleic acid probes, proteinase treatment of peptide probes, use of heat or denaturant to disrupt nucleic acid hybridization, use of heat or denaturant to disrupt aptamer binding, or use of heat or denaturant to disrupt bonding between antibody and protein. In one embodiment, the method further includes methods for programming HCR initiator functional linkage to bound probe. In one embodiment, the methods for programming HCR initiator functional linkage to bound probe comprise a) use of nucleic acid hybridization to add an initiator to a linker probe bearing a complementary nucleic acid molecule using sequencing by hybridization, b) use of an enzyme to add an initiator to a linker probe, c) use of heat or denaturant to disrupt nucleic acid hybridization to remove an initiator hybridized to a linker probe, d) use of toehold strand displacement to remove a protecting strand from an initiator that is localized to a target molecule via a linker probe, and e) incorporation of chemical, enzymatic, or photo-labile group between the initiator and linker probe, such that the initiator can be removed by chemical, enzymatic, or light treatments that disrupt the chemical linkage between the initiator and the linker probe. In one embodiment, the enzyme that adds the initiator to the linker probe is a DNA ligase that catalyzes a splint ligation reaction. In one embodiment, the method further includes methods for reversing a hybridization chain reaction. In one embodiment, the methods for reversing the hybridization chain reaction comprise a) using modified HCR monomers comprising one or more additional sequence for toehold strand displacement, such that addition of one or more complementary DNA strands will cause the HCR polymer to disassemble, and b) using modified HCR monomers comprising one or more enzymatic or chemical sensitive groups, or photo-labile groups in the DNA backbone of the HCR monomers, such that the HCR polymer can be fragmented or disrupted by chemical, enzymatic, or light treatments. In one embodiment, the method further includes methods for programming the functional generation of the HCR polymer fluorescent signal. In one embodiment, the methods for programming the HCR polymer functional generation of fluorescent signal comprise a) using modified HCR monomers comprising additional sequence capable of being probed using sequencing by synthesis (SBS), sequencing by ligation (SBL), or sequencing by hybridization (SBH) to introduce fluorescent moieties to the HCR polymer, b) using modified HCR monomers comprising enzymatic, chemical, or photo-labile groups between the HCR DNA monomer backbone and fluorescent moieties, such that the fluorescent moieties can be removed by chemical, enzymatic, or light treatments, c) using modified fluorescent probes capable of labeling a HCR polymer such as by SBS, SBL, or SBH, wherein the fluorescent probes comprise additional sequence for toehold strand displacement such that the fluorescent probes can be removed from the HCR polymer by disrupting the hybridization between the fluorescent probes and the HCR polymer, and d) using modified fluorescent probes capable of labeling a HCR polymer such as by SBS, SBL, or SBH, wherein the fluorescent probes comprise enzymatic, chemical, or photo-labile groups between the HCR polymer backbone and fluorescent moieties, such that the fluorescent moieties can be removed by chemical, enzymatic, or light treatments.

According to another aspect, the present disclosure provides a method for detecting one or more target analytes comprising contacting a sample with a cyclic hybridization chain reaction "HCR" system more than one time, wherein each target analyte within a sample is associated with one amplified fluorescence signal over the total number of HCR cycles. In one embodiment, the combination of HCR cycle and spectrally resolvable fluorescence signal generated by Cyclic HCR comprises a unique label for the target analyte.

According to another aspect, the present disclosure provides a method for detecting one or more target analytes comprising contacting a sample with a cyclic hybridization chain reaction "HCR" system more than one time, wherein each target analyte within a sample is associated with more than one amplified fluorescence signal over the total number of HCR cycles. In one embodiment, the amplified fluorescence signals generated by each target analyte are informatically combined into a composite label. In one embodiment, each target analyte is associated with a unique composite label. In another embodiment, the sample is fixed. In one embodiment, the composite label is generated by means of the spatial invariance of the target analytes between HCR cycles. In one embodiment, the target analytes are attached to a 3D matrix. In another embodiment, the composite label is generated by means of the spatial invariance of the target analytes between HCR cycles. In one embodiment, the composite label is generated by means of the positional order invariance of the target analytes between HCR cycles. In another embodiment, one or more components of the Cyclic HCR system are attached to a 3D matrix. In one embodiment, the composite label is generated by means of the spatial invariance of the target analytes between HCR cycles. In another embodiment, the composite label is generated by means of the positional order invariance of the target analytes between HCR cycles. In one embodiment, the association between the target analyte and the HCR fluorescence signal is programmable. In another embodiment, the association between the target analyte and the HCR fluorescence signal is programmable.

According to one aspect, the present disclosure provides a method for detecting one or more target analytes in a sample including (A) contacting the sample with one or more probe sets wherein each probe set comprises one or more primary probes each having a linker, and wherein each probe set is specific to a target analyte, wherein the one or more primary probes having a linker bind the target analyte; (B) contacting the sample with one or more hybridization chain reaction (HCR) initiators which bind to the linker, (C) contacting the sample with two or more metastable HCR monomers, wherein the one or more initiators contact the two or more metastable HCR monomers and initiates hybridization chain reaction to produce self-assembled and tethered nucleic acid amplification polymer products, and (D) attaching one or more detectable labels to the tethered nucleic acid amplification products, and optionally detecting the one or more detectable labels. In one embodiment, the probe is removable from the target analyte, the initiator is removable from the linker, the nucleic acid amplification polymer product is removable from the initiator or the one or more detectable labels are removable from the nucleic acid amplification polymer product. In another embodiment, the probe is removable from the target analyte, the initiator is removable from the linker, and the nucleic acid amplification polymer product is removable from the initiator. In one embodiment, the probe is removable from the target analyte. In another embodiment, the initiator is removable from the linker. In one embodiment, the nucleic acid amplification polymer product is removable from the initiator. In another embodiment, the one or more detectable labels are removable from the nucleic acid amplification polymer product. In another embodiment, the probe is removable from the target analyte, the initiator is removable from the linker, the nucleic acid amplification polymer product is removable from the initiator and the one or more detectable labels are removable from the nucleic acid amplification polymer product.

According to another aspect, the present disclosure provides for a method for detecting one or more target analytes in a sample including (A) contacting the sample with one or more probe sets wherein each probe set comprises one or more primary probes each having a linker, and wherein each probe set is specific to a target analyte, wherein the one or more primary probes having a linker bind the target analyte; (B) contacting the sample with one or more hybridization chain reaction (HCR) initiators which bind to the linker, (C) contacting the sample with two or more metastable HCR monomers including a detectable label, wherein the one or more initiators contact the two or more metastable HCR monomers and initiate hybridization chain reaction to produce self-assembled and tethered nucleic acid amplification polymer products, and (D) optionally detecting the one or more detectable labels. In one embodiment, the probe is removable from the target analyte. In another embodiment, the initiator is removable from the linker. In yet another embodiment, the nucleic acid amplification polymer product is removable from the initiator.

According to one aspect, the present disclosure provides a method for identifying a target analyte in a sample, including (a) contacting the sample with one or more probes, wherein a given probe of said one or more probes is coupled to a linker, and wherein said given probe has a sequence that is complementarity to a sequence of said target analyte, wherein upon contacting said sample with said one or more probes, said given probe binds to said target analyte; (b) contacting the sample with one or more hybridization chain reaction (HCR) initiators under conditions sufficient to permit a given HCR initiator of said one or more HCR initiators to bind to the linker, wherein said given HCR initiator is separate from said given probe, and wherein upon contacting said sample with said one or more HCR initiators, said linker couples said probe with said given HCR initiator; (c) contacting the sample with one or more HCR amplifiers to trigger a hybridization chain reaction, wherein a given HCR amplifier of said one or more HCR amplifiers comprises at least one HCR monomer that comprises a detectable label, thereby generating an amplification product comprising said HCR monomer, which amplification product is coupled to said given probe; and (d) detecting said amplification product, thereby identifying said target analyte. In one embodiment, the method further includes contacting the sample with a plurality of probe sets each specific to a target analyte, the plurality of probe sets configured to allow for programmable and temporally ordered hybridization chain reactions. In another embodiment, the detectable label is fluorescent label and said detecting comprises detecting fluorescent signals, wherein a totality of the temporally generated fluorescent signals provides a unique set of information comprising a molecular identity, molecular quality, or molecular configuration for each target analyte. In one embodiment, the one or more HCR amplifiers comprise two metastable DNA hairpins. In another embodiment, the detectable label of the one or more HCR amplifiers comprises spectrally distinct fluorescence signals for multiplexed detection. In one embodiment, the detectable label of the HCR monomer comprises a sequencing template for fluorescent sequencing by hybridization, fluorescent sequencing by ligation, or fluorescent sequencing by synthesis. In another embodiment, the target analyte comprises nucleic acid polymers including RNA, DNA, RNA analogs, DNA analogs, proteins, and chemical modifications thereof. In yet another embodiment, the target analyte comprises lipids, metabolites, biomolecules, and other small molecules. In one embodiment, the method further includes serially labeling target analytes. In one embodiment, said serially labeling comprises associating each analyte with a plurality of HCR initiators. In another embodiment, the given HCR amplifier comprises two or more metastable HCR monomers. In one embodiment, said binding of said given to the target analyte is repeated two or more times. In one embodiment, the linker can be a bond or comprise a sequence portion that is complementary to a sequence portion of an oligonucleotide comprising an initiator sequence and hybridizes to the oligonucleotide comprising the initiator sequence. In certain embodiments, the method further includes disrupting or reversing the coupling between the given probe and the linker, the coupling between the linker and the HCR initiator, or the coupling between said given probe and the HCR initiator. In one embodiment, the linker comprises an initiator sequence cognate to a protecting group, which prevents the HCR initiator from triggering the HCR. In another embodiment, the protecting group is a protecting oligonucleotide. In another embodiment, the method further includes disrupting the protecting group from the linker, thereby allowing the HCR initiator to trigger the HCR. In one embodiment, said disrupting comprises introducing a deprotecting oligonucleotide to the sample to remove the protecting group by a toehold strand displacement. In another embodiment, the method further includes degrading or disassembling the amplification product after said detecting. In one embodiment, the method further includes disrupting or reversing a coupling between the amplification product and the detecting label after said detecting. In another embodiment, the method further includes disrupting or reversing the binding of said given probe to said target analyte. In yet another embodiment, the method further includes conducting a plurality of rounds of hybridization chain reactions comprising a plurality of detection cycles. In one embodiment, the plurality of rounds of hybridization chain reactions comprise reusing the one or more HCR initiators or the one or more HCR amplifiers. In another embodiment, the method further includes programming a functional linkage between the given HCR initiator to the given probe, wherein said programming comprises a) use of nucleic acid hybridization to add the HCR initiator to a linker probe bearing a complementary nucleic acid molecule using sequencing by hybridization, b) use of an enzyme to add the HCR initiator to a linker probe, c) use of heat or denaturant to disrupt nucleic acid hybridization to remove the HCR initiator hybridized to a linker probe, d) use of toehold strand displacement to remove a protecting strand from the HCR initiator that is localized to a target molecule via a linker probe, or e) incorporation of chemical, enzymatic, or photo-labile group between the HCR initiator and a linker probe, such that the HCR initiator can be removed by chemical, enzymatic, or light treatments that disrupt the chemical linkage between the initiator and the linker probe. In one embodiment, the enzyme that adds the HCR initiator to the linker probe is a DNA ligase that catalyzes a splint ligation reaction. In another embodiment, the method further includes reversing or arresting the hybridization chain reaction. In one embodiment, reversing or arresting the hybridization chain reaction comprises a) using modified HCR monomers comprising one or more additional sequences for a toehold strand displacement, such that addition of one or more complementary DNA strands will cause the amplification product to disassemble, or b) using modified HCR monomers comprising one or more enzymatic or chemical sensitive groups, or photo-labile groups in a DNA backbone of the HCR monomers, such that the amplification product is fragmented or disrupted by chemical, enzymatic, or light treatments. In another embodiment, the method further includes programming generation of fluorescent signals from the amplification product by a) using modified HCR monomers comprising additional sequences capable of being probed using sequencing by synthesis (SBS), sequencing by ligation (SBL), or sequencing by hybridization (SBH) to introduce fluorescent moieties to the amplification product, b) using modified HCR monomers comprising enzymatic, chemical, or photo-labile groups between a DNA backbone of the HCR monomer and the detectable label comprising fluorescent moieties, such that the fluorescent moieties can be removed by chemical, enzymatic, or light treatments, c) using modified fluorescent probes capable of labeling the amplification product by sequencing by synthesis (SBS), sequencing by ligation (SBL), or sequencing by hybridization (SBH), wherein the fluorescent probes comprise additional sequences for toehold strand displacement such that the fluorescent probes can be removed from the amplification product by disrupting hybridization between the fluorescent probes and the amplification product, or d) using modified fluorescent probes capable of labeling the amplification product such as by SBS, SBL, or SBH, wherein the fluorescent probes comprise enzymatic, chemical, or photo-labile groups between a backbone of the amplification product and detectable label comprising fluorescent moieties, such that the fluorescent moieties can be removed by chemical, enzymatic, or light treatments. In one embodiment, the given probe is removable from the target analyte, the HCR initiator is removable from the linker, the amplification product is removable from the HCR initiator, or the detectable label is removable from the amplification product.

According to another aspect, the present disclosure provides a cyclic hybridization chain reaction (HCR) system comprising one or more probes, wherein a given probe of said one or more probes is coupled to a linker, wherein said given probe has a sequence that is complementary to a sequence of a target analyte, one or more HCR initiators, wherein a given HCR initiator of said one or more HCR initiators is separate from said given probe, and wherein said given HCR initiator is configured to bind to the linker and couple said probe with said give HCR initiator, and one or more HCR amplifiers, wherein a given HCR amplifier of said one or more HCR amplifiers comprises at least one HCR monomer that comprises a detectable label, wherein said given HCR initiator is configured to couple to the HCR monomer and trigger a hybridization chain reaction to generate an amplification product comprising said HCR monomer, which amplification product is coupled to said given probe. In one embodiment, the system further includes a plurality of probe sets each specific to a target analyte, wherein the plurality of probe sets are designed for programmable and temporally ordered hybridization chain reactions. In one embodiment, the plurality of probe sets are configured to provide temporally generated fluorescent signals, and wherein a totality of the temporally generated fluorescent signals provide a unique set of information for each target analyte including molecular identity, molecular quality, or molecular configuration. In another embodiment, each of the HCR amplifiers comprise two or more metastable HCR monomers each of which are DNA hairpins. In another embodiment, the one or more HCR amplifiers comprise two or more metastable HCR monomers comprising detectable labels, the detectable labels comprising spectrally distinct fluorescent signals for multiplexed detection. In one embodiment, said HCR monomer is a non-fluorescent HCR monomer. In another embodiment, the non-fluorescent HCR monomer is configured to be fluorescently labeled during or after the generation of the amplification product. In one embodiment, the amplification product formed from the non-fluorescent monomers are fluorescently labeled after generation of the amplification product by: fluorescent sequencing by hybridization, fluorescent sequencing by ligation, or fluorescent sequencing by synthesis, by enzymatic reaction, or by chemical reaction. In another embodiment, the one or more probes, the linker, one or more HCR initiators, or one or more HCR amplifiers are configured to be re-used. In one embodiment, the linker is a nucleic acid sequence that is complementary to an oligonucleotide comprising the HCR initiator. In another embodiment, the linker comprises a functional group for programmable disassociation from the initiator. In one embodiment, detection of the detectable label can be programmatically generated and reset. In another embodiment, the HCR monomer contains functional groups for programmable disassembly or degradation of the amplification product. In one embodiment, the functional groups comprise toehold strand displacement sequences. In another embodiment, the functional groups comprise chemically labile, enzymatically labile, or photolabile chemical groups. In one embodiment, the binding of the given probe to the target analyte is configured to be disrupted or reversed during the hybridization chain reaction. In another embodiment, the given probe binding to the target analyte is disrupted or reversed by chemical treatment, enzymatic treatment, DNase treatment of RNA in situ hybridization (ISH) probes, exonuclease treatment of 5' phos ISH probes, nuclease treatment of nucleic acid probes, proteinase treatment of peptide probes, use of heat or denaturant to disrupt nucleic acid hybridization, use of heat or denaturant to disrupt aptamer binding, or use of heat or denaturant to disrupt bonding between antibody and protein.

According to one aspect, the present disclosure provides a method for identifying a target analyte in a sample, including (a) contacting said sample with a primary probe that comprises a sequence that is complementary to a sequence of said target analyte; (b) contacting said sample with a secondary probe configured to couple to said primary probe, wherein coupling of said primary probe with said secondary probe facilitates a hybridization chain reaction (HCR) in the presence of at least one HCR amplifier comprising a detectable label, to generate an amplification product comprising said detectable label, wherein said secondary probe is separate from the HCR amplifier and said primary probe; and (c) detecting said detectable label, thereby identifying said target analyte. In one embodiment, said HCR is not polymerase chain reaction. In another embodiment, said amplification product is coupled to said primary probe. In one embodiment, said HCR amplifier has a sequence that is complementary to a sequence of said secondary probe. In another embodiment, said primary probe is coupled to a linker that permits said primary probe to couple to said secondary probe. In one embodiment, the primary probe comprises an HCR initiator that initiates said HCR. In another embodiment, the primary probe comprises a protecting group which prevents the HCR initiator from initiating said HCR prior to said contacting said sample with the secondary probe. In one embodiment, said protecting group comprises a protecting oligonucleotide. In another embodiment, the secondary probe comprises an HCR initiator that initiates said HCR. In one embodiment, said secondary probe does not include a detectable label. In another embodiment, said HCR amplifier comprises two or more metastable HCR monomers. In one embodiment, each of said two or more metastable HCR monomers comprise a metastable DNA hairpin.

According to another aspect, the present disclosure provides a system for identifying a target analyte in a sample, including a detector for detecting a detectable label; and a controller operatively coupled to said detector, wherein said controller comprises one or more computer processors that are individually or collectively programed to direct: (i) contacting said sample with a primary probe that comprises a sequence that is complementary to a sequence of said target analyte; (ii) contacting said sample with a secondary probe configured to couple to said primary probe, wherein coupling of said primary probe with said secondary probe facilitates a hybridization chain reaction (HCR) in the presence of at least one HCR amplifier comprising a detectable label, to generate an amplification product comprising said detectable label, wherein said secondary probe is separate from the HCR amplifier and said primary probe; and (iii) using said detector to detect said detectable label, thereby identifying said target analyte.

According to another aspect, the present invention provides a kit for identifying a target analyte in a sample, including a hybridization chain reaction (HCR) amplifier comprising a detectable label, which HCR amplifier is configured to facilitate HCR; a primary probe that comprises a sequence that is complementary to a sequence of said target analyte; and a secondary probe configured to couple to said primary probe, wherein said secondary probe does not include a detectable label, wherein said secondary probe is separate from said HCR amplifier and said primary probe. In one embodiment, the kit further includes instructions for using said HCR amplifier, primary probe and said secondary probe to conduct said HCR. In another embodiment, the kit further includes a cleaving agent, said cleaving agent configured to cleave the linker between the primary probe and the secondary probe, thereby disrupting the one or more HCR initiators from triggering the chain reaction with the one or more HCR amplifiers. In another embodiment, said HCR amplifier has a sequence that is complementary to a sequence of said secondary probe. In one embodiment, said primary probe is coupled to a linker that permits said primary probe to couple to said secondary probe. In another embodiment, the primary probe comprises an HCR initiator that initiates said HCR. In one embodiment, the primary probe comprises a protecting group which prevents the HCR initiator from initiating said HCR prior to coupling of said primary probe with the secondary probe. In another embodiment, said protecting group comprises a protecting oligonucleotide. In one embodiment, the secondary probe comprises an HCR initiator that initiates said HCR. In another embodiment, said HCR amplifier comprises two or more metastable HCR monomers.

According to an additional aspect, the present disclosure provides a method for disrupting production of a hybridization chain reaction (HCR) amplification product, including (a) providing a sample comprising a primary probe coupled to a secondary probe, wherein the primary probe comprises a sequence that is complementary to a sequence of a target analyte, and wherein said primary probe is hybridized to said target analyte under conditions sufficient to facilitate hybridization chain reaction (HCR) to generate an amplification product; and (b) contacting said sample with a cleaving agent to decouple said primary probe from said secondary without decoupling said primary probe from said target analyte, thereby preventing said HCR and disrupting generation of said amplification product.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 1A depicts an HCR mechanism. Metastable fluorescent hairpins self-assemble into fluorescent amplification polymers upon detection of a cognate initiator. Initiator I1, comprised of single-stranded segments "b*-a*", nucleates with hairpin H1 via base-pairing to single-stranded toehold "a" of H1, mediating a branch migration that opens the hairpin H1 to form complex I1-H1 containing single-stranded segment "c*-b*". This complex nucleates with hairpin H2 by means of base-pairing to single-stranded toehold "c", mediating a branch migration that opens the hairpin to form complex I1-H1-H2 containing single-stranded segment "b*-a*". Thus, the initiator sequence is regenerated, providing the basis for a chain reaction of alternating H1 and H2 polymerization steps. Red stars denote fluorophores. FIG. 1B depicts an in situ hybridization protocol. Detection stage: DNA probe sets, with each probe containing initiators I1 and I2 and a region complementary to an mRNA target, are hybridized to mRNA targets; unbound probes are washed from the sample. Amplification stage: initiators trigger self-assembly of tethered fluorescent amplification polymers; un-polymerized hairpins are washed from the sample. FIG. 1C depicts an experimental timeline. The same two-stage protocol is used independent of the number of target mRNAs. For multiplexed experiments (three-color example depicted), probe sets for different target mRNAs (five probes depicted per set) carry orthogonal initiators that trigger orthogonal HCR amplification cascades labeled by spectrally distinct fluorophores.

FIGS. 5A-C depicts schematics of specific mechanisms of programming primary probe binding via Step A of the Cyclic HCR method. FIG. 5A depicts a target analyte bound in Step 1 with a nucleic acid or nucleic acid analog aptamer, called "Probe Alpha," cognate to an HCR initiator and subsequently detected via amplified fluorescence HCR signal, via a linker, such as a chemical bond or molecular interaction, but understood to be any kind of programmable or non-programmable linker as described by Step B of Cyclic HCR, referred to as "Linker Alpha". In this schematic, the Linker represents all downstream information transfer via Steps B-D of Cyclic HCR. In Step 2, binding between the aptamer and the target molecule is disrupted, as by treatment with a denaturant such as formamide, which destabilizes the interactions such as hydrogen bonding and hydrophobic interactions between the aptamer and the target molecule. Probe Alpha is then washed from the sample. At Step 3, the same primary probe, aptamer Probe Alpha is re-introduced to the sample, again binding the target molecule, but cognate to a different linker, "Linker Beta," which represents the downstream Steps B-D of Cyclic HCR reaction. For example, Linker Beta may differ from Linker Alpha in that Linker Beta is associated with a spectrally distinct HCR fluorescence signal than that of Linker Alpha. FIG. 5B depicts a target analyte bound in Step 1 by an antibody as the primary probe, "Probe Alpha", cognate to an HCR initiator and subsequently detected via amplified fluorescence HCR signal, via a linker, such as a chemical bond or molecular interaction, referred to as "Linker Alpha". At Step 2, binding between the antibody and the target molecule is disrupted as in FIG. 5A Step 2. In Step 3, a different antibody, "Probe Beta", is introduced to bind the same target analyte, cognate to an HCR initiator and subsequently detected via amplified fluorescence HCR signal, via a linker, such as a chemical bond or molecular interaction, referred to as "Linker Beta", which is distinct from "Linker Alpha" from Step 1 as in FIG. 5A. FIG. 5C depicts the same reversibility of Step A as in FIG. 5A, except with an RNA or DNA target molecule, which is bound by a nucleic acid or nucleic acid analog ISH probe referred to as "Probe Alpha". In this example, the reversal of Cyclic HCR Step A is mediated in Step 2 of FIG. 5C, as by activation of a photolabile group incorporated into Probe Alpha, which disrupts nucleic acid annealing upon induction by UV light; or by treatment with DNase enzyme to digest a DNA ISH Probe Alpha bound to a target RNA molecule.

In FIG. 7A, an analyte has been bound by "Probe Alpha", which contains a linkage to an HCR initiator sequence "i1". The linkage between these may be covalent, as in direct conjugation of the HCR initiator sequence oligonucleotide onto an antibody Probe Alpha for detection of a protein target analyte. However, the linkage is not a functional one because the initiator sequence is unable to initiate an HCR polymerization reaction due to it being protected by a protecting oligo, shown in purple, which also contains additional sequence "a." At Step 1, a de-protecting oligo referred to as the Step B Probe is introduced to the sample and removes the protecting strand by means of toehold strand displacement. The displaced protecting strands are washed from the sample.

Subsequently, HCR hairpins are added, which generates an amplified fluorescence HCR signal which is detected. At Step 2, the initiator "i1" is again rendered unable to initiate the HCR polymerization reaction by means of capping it with a complementary protecting strand "i1'". In FIG. 7B, a target analyte is bound by primary Step A Probe "Beta", which does not contain an HCR initiator sequence, but instead contains additional binding moiety "b", such as an DNA oligonucleotide sequence, referred to as "Linker Beta". At Step 1, an oligonucleotide probe called Step B Probe "b'-i1" is added to the sample and hybridized to Linker Beta, introducing the HCR initiator sequence "i1". Subsequently, HCR hairpins are added, which generates an amplified fluorescence HCR signal which is detected. At Step 2, the linkage between the region of Step B Probe "b'-i1" complementary to motif "b" and the region containing the initiator sequence "i1" is cleaved, such as by silver nitrate cleavage of a bridging phosphorothioate bond in the backbone of the oligonucleotide "b'-i1", where the cleavable group is represented by the small yellow circle of "b'-i1", returning the Primary Step A Probe to a state where it is unable to initiate an HCR polymerization reaction. FIG. 7C depicts the same Step B reaction as in FIG. 7B, except in FIG. 7C the mechanism of creating the functional linkage between the Primary Probe and the HCR initiator is by a sequencing by ligation reaction to conjugate an oligonucleotide containing sequence complementary to Linker motif a "$a^{2'}$" and a separate sequence containing HCR initiator sequence "i1" onto the Primary Probe. The sequencing by ligation reaction is primed by oligo "$a^1$+". At Step 2, the initiator "i1" is again rendered unable to initiate the HCR polymerization reaction by means of capping it with a complementary protecting strand "i1'".

FIGS. 10A-10C depict a schematic representation of materials and methods for programming Step C of Cyclic HCR. FIG. 10A depicts a target analyte bound by Primary Probe "Alpha", functionally linked to the initiator sequence "i1" via a linker represented as "L", but understood to be any kind of programmable or non-programmable linker as described in Step B of Cyclic HCR. At Step 1, cleavable fluorescent HCR hairpins are added to the sample. The blue stars represent fluorescent moieties; while the blue squares represent cleavable moieties, such as 5' or 3' bridging phosphorothioate linkages in the backbone of the HCR hairpins. The hairpins contact the initiator sequence "i1" and form an amplified fluorescent HCR polymer at the target analyte, which is detected. At Step 2, a reagent catalyzing cleavage of the cleavable moiety, such as silver nitrate for the example of a bridging phosphorothioate linkage, is added to the sample, which causes the HCR hairpins to be cleaved at the site of the modified backbone represented by the blue square. The HCR polymer is thereby fragmented, and the fragments are washed from the sample. In this depiction, a fragment complementary to sequence "i1" is left bound to the initiator sequence, effectively capping the initiator, which represents a concerted reversal of Cyclic HCR Steps B and C. FIG. 10B depicts a target analyte bound by Primary Probe "Alpha", functionally linked to the initiator sequence "i1" via a linker represented as "L", but understood to be any kind of programmable or non-programmable linker as described in Step B of Cyclic HCR. At Step 1, cleavable fluorescent HCR hairpins are added to the sample. The blue stars represent fluorescent moieties, and the HCR hairpins contain an additional sequence motif handle, represented as the purple segment of the hairpin. The hairpins contact the initiator sequence "i1" and form an amplified fluorescent HCR polymer at the target analyte, which is detected. The HCR polymer also contains the additional handle motifs as single-stranded sequences. At Step 2, toehold displacement strands (generically referred to herein as Step C probes) are added to the sample, which bind to the additional handle sequence of the HCR polymers and induce a toehold strand displacement reaction, which causes the HCR polymer to be disassembled into double-stranded fragments, which are washed from the sample. FIG. 10C depicts a target analyte bound by Primary Probe "Alpha", functionally linked to the initiator sequence "i1" via a linker represented as "L", but understood to be any kind of programmable or non-programmable linker as described in Step B of Cyclic HCR. At Step 1, cleavable fluorescent HCR hairpins are added to the sample. The blue stars represent fluorescent moieties, and the HCR hairpins contain an additional modification represented by the red triangle, which is recognized by an exonuclease, such as a 5' monophosphate recognized by Terminator Exonuclease. The hairpins contact the initiator sequence "i1" and form an amplified fluorescent HCR polymer at the target analyte, which is detected. At Step 2, an exonuclease targeted to the modified hairpins are added to the sample, which recognize the modified HCR polymers and digest the constituent oligonucleotides into single nucleotides, which are washed from the sample. In each of FIGS. 10A-C, the sample is left in a state where no HCR polymers or the associated fluorescence signals are present.

FIG. 14A depicts a target analyte represented by the blue circle labeled with a number of primary probes, represented by orange triangles, functionally linked to HCR initiators, which have generated HCR amplicons, being fluorescently labeled programmatically, such as by sequencing by hybridization (e.g. hybridizing a fluorescent probe to a particular sequence contained in the HCR amplicon), or sequencing by synthesis or ligation. Here, the signal is additive between the two cycles, e.g. using only the programmability of the association of fluorescence with the polymer, and not dissociation of fluorescence with the polymer. FIG. 14B depicts a Step D probe being conjugated to an HCR polymer, such as by sequencing by hybridization or sequencing by ligation reaction, carrying a fluorophore. After imaging, the fluorescent moiety is chemically cleaved from the HCR amplicon, as by silver cleavage of a bridging sulfur atom phosphorothioate linkage in the DNA strand, leaving double-stranded overhangs on the HCR polymer, but resetting the sample to a dark state.

FIGS. 15A-15D depict a schematic of an implementation of detection of a combinatorial signal over multiple cycles of HCR constituting a barcode in an exponential labeling space as the detected message. In FIG. 15A, two targets are each labeled with four independent Primary Probes, depicted as orange triangles, each of which generates a temporally ordered fluorescence signal during the cyclic HCR experiment. Each temporally ordered fluorescence signal is referred to as a "Label," with n total labels. Each unique label corresponds to a unique combination of fluorescence spectral signal and timepoint within a cyclic HCR reaction. For example, a CY3 signal in the first round of Cyclic HCR may be understood as "Label a", whereas a CY3 signal in the second round of Cyclic HCR may be understood as "Label f". Notice that both target analytes share "Label a", but over the set of all ordered fluorescence signals, each target analyte has a unique set of ordered labels, [a, d, h, m] for Target 1, and [a, f, g, n] for Target 2, e.g. the primary probes in this example may be four ISH probes for each mRNA Target 1 and 2. Cyclic HCR is conducted, and ordered fluorescence signals are detected. After the totality of HCR cycles and detection events, a combinatorial label is generated for each target analyte, and the combinatorial label is mapped to certain original information, such the molecular species of the target analyte. In FIG. 15B, each Target 1 and 2 is bound with a single Primary Probe, shown as the orange triangle, which contains a number of independent Labels, where each unique label is understood to a unique combination of fluorescence spectral signal and time point within a cyclic HCR reaction. In this example, the Primary Probes could be antibodies bound to protein targets 1 and 2; the Labels can be understood to be distinct DNA linker motifs, which are hybridized by Step B Probes serially or in parallel in a Cyclic HCR experiment. Cyclic HCR is conducted, and ordered fluorescence signals are detected. After the totality of HCR cycles and detection events, a combinatorial label is generated for each target analyte, and the combinatorial label is mapped to some original information, such the molecular species of the target analyte. FIG. 15C depicts a look-up table mapping the labels from FIG. 15A onto a set of temporally ordered, spectrally distinct HCR signals. The left column contains the label index. The column "HCR Cycle" refers to the cycle number or time point of detection within a Cyclic HCR reaction. In this example, n labels are detected by k orthogonal and spectrally distinct HCR systems in ceil(n/k) cycles. The column "HCR Index" refers to which of the k orthogonal and spectrally distinct HCR systems corresponds to each Label during each cycle of HCR. FIG. 15D depicts a look-up table mapping a detected message, understood to be the ordered set of HCR signals generated by the targets depicted in FIG. 15A, constituting the barcode, to the identity of the analytes being detected. The Barcode is constructed of ternary values, i.e. of the set [1, 2, 3], which each correspond to an HCR index in FIG. 15C. In this example, the HCR indices may refer to three orthogonal HCR systems, each labeled with a spectrally distinct fluorescent moiety. The order of the values in the barcode corresponds to the order of the HCR cycles in FIG. 15C.

In FIG. 17A, the Primary probes are each modified with additional sequence on the 3' and 5' ends of the oligonucleotides to contain the four sequences assigned to the quaternary values of each barcode position within the chunk of four assigned to each probe, for the barcode assigned to the target molecule. The target RNA or DNA molecule is hybridized with the plurality of primary probes. In FIG. 17B, during each cycle of Cyclic HCR, a pool of four Step B Probes are added to the sample, corresponding to the quaternary values [0, 1, 2, 3] at each position "bx" for each position of the barcode. The four Step B Probes corresponding to the quaternary values each contain additional sequence functioning as an HCR initiator for one of the four orthogonal, spectrally resolvable HCR systems, referred to as initiator $i_q$. In FIG. 17B, a set of four Step B Probes containing sequence "$b_n$" are annealed and excess are washed away. Each Step B Probe contains one of the four "$b_n$" sequences corresponding to quaternary value q=[0, 1, 2, 3]; therefore the Step B Probes can be uniquely referred to as "$b_{n,q}$", where n refers to the cycle of HCR and the barcode position being detected in that cycle, and q refers to the quaternary value [0, 1, 2, 3]. In Step 1 of FIG. 17B, HCR hairpins are added to the sample, contact the initiator, and HCR polymer q is generated at initiator $i_q$, generating an amplified fluorescence signal which is detected. In Step 2 of 17B, The HCR amplicon has been degraded using the methods and materials for programming Cyclic HCR Step C, and the linker Step B Probe has also been removed from the sample using the methods and materials for programming Step B. Steps B and C of cyclic HCR are cycled a total of 12 times using this approach to detect each position of the 12-value barcode, with each value corresponding to one of four spectrally distinct amplified HCR fluorescence signals. Only four orthogonal, independent, spectrally distinct HCR systems are used to generate over 16 million unique barcodes using N=12 cycles of Cyclic HCR, with each cycle reading out four possible quaternary values, (barcode space $4^{12}$) via 4N orthogonal linker domains.

FIGS. 18A-18D depict a diagram of an example of exponential barcoding probe design. One design of the probe set, where each probe contains a region for targeted hybridization (shown in blue) against a target RNA or DNA molecule (shown in green), and an information-bearing label sequence containing the combined pairwise information about the cycle of HCR (N) and HCR probe set (k). Here the region for targeted hybridization of the primary probe against the target nucleic acid is 25-42 bases long, and the label sequence portion of the primary probe is 25 bases long. The set of all probes are designed for 5 cycles of HCR using 4 orthogonal HCR probe sets, each encoding a quaternary signal value in the target barcode and detected using a spectrally resolvable fluorescence signal of the set [FAM, CY3, Texas Red, and Cy5], requiring 20 orthogonal information-bearing probe sets and giving 1024 possible barcodes ($4^5$). FIG. 18A depicts the design of the primary probes and the order of the procedure as including the steps of hybridizing the primary probe set and then conducting Cyclic HCR. FIG. 18B contains a table including the partial map of the label sequence, of the set 0-19, to the cycle, orthogonal HCR system, and fluorescence signal as part of the experimental design. FIG. 18C depicts the first cycle of HCR, wherein four Step B probes are hybridized to the sample, one of which anneals to a primary probe on each of the target molecules. Excess Step B probes are washed away, and HCR hairpins are added to the sample, where they contact the initiators and polymerize into a fluorescently labeled HCR polymer. Fluorescence signal is detected and understood to be one of the quaternary values in the first position of the barcode. In this panel, the target molecule has value 2 at the first position of the barcode, corresponding to HCR system number 2, which has a CY3 fluorescence signal. After detection of the signal, the HCR polymer is removed from the sample using methods described as Cyclic HCR Step C, and Step B is also reversed, such that the Primary Probe no longer contains or is linked to a functional HCR initiator. FIG. 18D depicts the second cycle of HCR, wherein four Step B probes are hybridized to the sample, one of which anneals to a primary probe on each of the target molecules. Excess Step B probes are washed away, and HCR hairpins are added to the sample, where they contact the initiators and polymerize into a fluorescently labeled HCR polymer. Fluorescence signal is detected and understood to be one of the quaternary values in the first position of the barcode. In this panel, the target molecule has value 1 at the first position of the barcode, corresponding to HCR system number 1, which has a FAM fluorescence signal. After detection of the signal, the HCR polymer is removed from the sample using methods described as Cyclic HCR Step C, and Step B is also reversed, such that the Primary Probe no longer contains or is linked to a functional HCR initiator. After three additional cycles of HCR, not depicted, each target molecule is identified using the unique combination of the five amplified fluorescence signals generated during Cyclic HCR, and constituting a unique combinatorial barcode.

FIGS. 25A-25C depict certain implementations of the Cyclic HCR technology. FIG. 25A depicts HCR fluorescent amplification on beads. Streptavidin-coupled magnetic beads (Dynabeads) were conjugated to a biotin-modified DNA oligonucleotide by hybridizing the beads with the DNA oligo for 30 minutes in PBS buffer, followed by washing several times using a magnet to prevent the beads from being removed with the supernatant. One pool of beads, referred to as "+ Step B Probe" was then annealed with a secondary probe comprising an HCR initiator, which is complementary to the primary biotinylated probe, by incubating in 2× SSC for 10 minutes. The "– Step B Probe" was incubated in SSC only with no secondary oligo. Both sets of beads were washed 5 times for 5 minutes each in 0.2× SSC. Beads were then added to positively charged glass. CY3-labeled HCR amplifier monomers were snap cooled according to the protocol (Molecular Instruments), and 30 pmol each were added to 500 uL volume of 5× SSC to the beads, and incubated at room temperature for 4 hours. Both beads were washed 5 times for 5 minutes each in 0.2× SSC. Beads were imaged in both widefield and CY3 channels, demonstrating selective amplification of the beads with the Step B Probe. In this manner, the labeling cascade from the primary probe to the detection of HCR fluorescence signal have been decoupled. In FIG. 25B, *Drosophila melanogaster* embryos were harvested and were permeabilized according to standard protocols, and then incubated with LabelX reagent to modify RNA with an acrydite moiety. The embryos were then embedded within an acrylamide hydrogel matrix, linking the RNA molecules to the hydrogel. The sample was then treated extensively with proteinase to clarify the sample and reduce autofluorescence. The sample was used for in situ hybridization against RNA POLII mRNA, using the sequences in Table 1, by overnight incubation in a hybridization buffer containing SSC and a crowding agent dextran sulfate. The embryos The Step B probe with Label ID 0 from Table 2 was then hybridized to the primary probes. HCR resulted in generation of amplified fluorescence puncta within the *Drosophila* embryos. FIG. 25C depicts two cycles of HCR from massively multiplex Cyclic HCR ISH targeting a pool of 500 mRNAs in primary human fibroblast cells. Human fibroblasts were cultured on glass, fixed, and permeabilized. A pool of DNA ISH probes targeting a set of 500 mRNAs was added to the sample and hybridized for 48 hours in a hybridization buffer containing SSC and a crowding agent dextran sulfate. A certain subset of Step B linker probes were hybridized to the primary probes, and HCR was used to generate two populations of non-fluorescent, orthogonal tethered HCR polymers, each having an additional handle for hybridization of a fluorescent Step D probe. In Cycle 1, a certain Step D probe were hybridized to one subset of the polymers and used to generate amplified fluorescence signal, which was detected. The sample was then treated with silver nitrate to cleave the fluorophores from the Step D probes. In Cycle 2, the other Step D probe was hybridized to the other subset of polymers to generate an amplified fluorescence signal using the same fluorescent moiety as in Cycle 1, which was detected.

DETAILED DESCRIPTION

The disclosure provides for a method for detecting one or more target analytes in a sample including the steps of: (A) contacting the sample with one or more probe sets wherein each probe set comprises one or more primary probes each having a linker, and wherein each probe set is specific to a target analyte, wherein the one or more primary probes having a linker bind the target analyte, (B) contacting the sample with one or more hybridization chain reaction (HCR) initiators which bind to the linker, (C) contacting the sample with two or more metastable HCR monomers, wherein the one or more initiators contact the two or more metastable HCR monomers and initiates hybridization chain reaction to produce self-assembled and tethered nucleic acid amplification polymer products, and (D) attaching one or more detectable labels to the tethered nucleic acid amplification products, and optionally detecting the one or more detectable labels. The disclosure provides that the probe is removable from the target analyte, the initiator is removable from the linker, the nucleic acid amplification polymer product is removable from the initiator or the one or more detectable labels are removable from the nucleic acid amplification polymer product. The disclosure provides that the probe is removable from the target analyte, the initiator is removable from the linker, the nucleic acid amplification polymer product is removable from the initiator and the one or more detectable labels are removable from the nucleic acid amplification polymer product.

The disclosure provides a method for detecting one or more target analytes in a sample including the steps of: (A) contacting the sample with one or more probe sets wherein each probe set comprises one or more primary probes each having a linker, and wherein each probe set is specific to a target analyte, wherein the one or more primary probes having a linker bind the target analyte, (B) contacting the sample with one or more hybridization chain reaction (HCR) initiators which bind to the linker, (C) contacting the sample with two or more metastable HCR monomers including a detectable label, wherein the one or more initiators contact the two or more metastable HCR monomers and initiate hybridization chain reaction to produce self-assembled and tethered nucleic acid amplification polymer products, and (D) optionally detecting the one or more detectable labels. The disclosure provides that the probe is removable from the target analyte. The disclosure provides that the initiator is removable from the linker. The disclosure provides that the nucleic acid amplification polymer product is removable from the initiator.

Figure 1A:
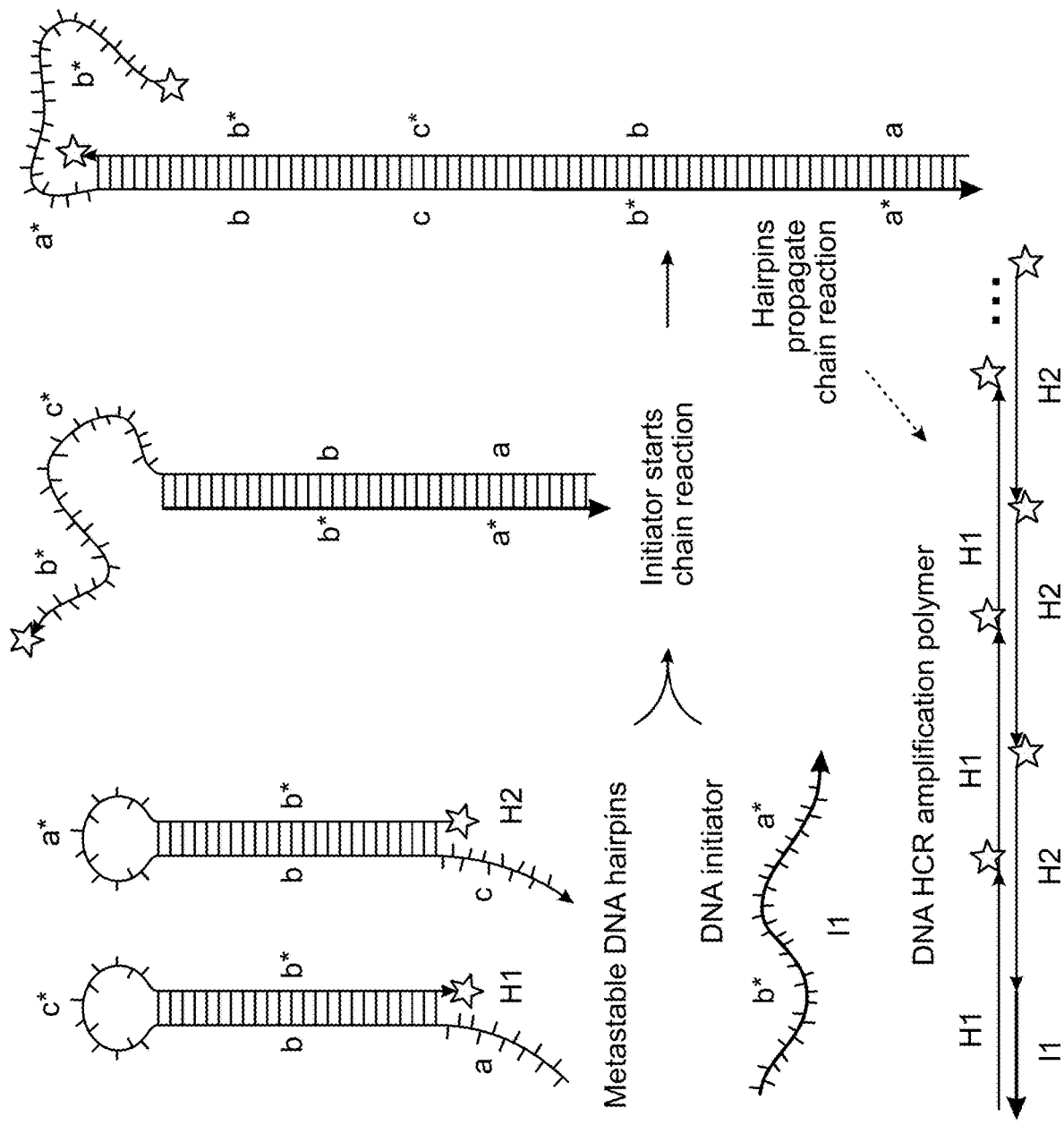
FIGS. 1A-1C depict an in situ amplification via hybridization chain reaction (HCR).
Figure 1B:
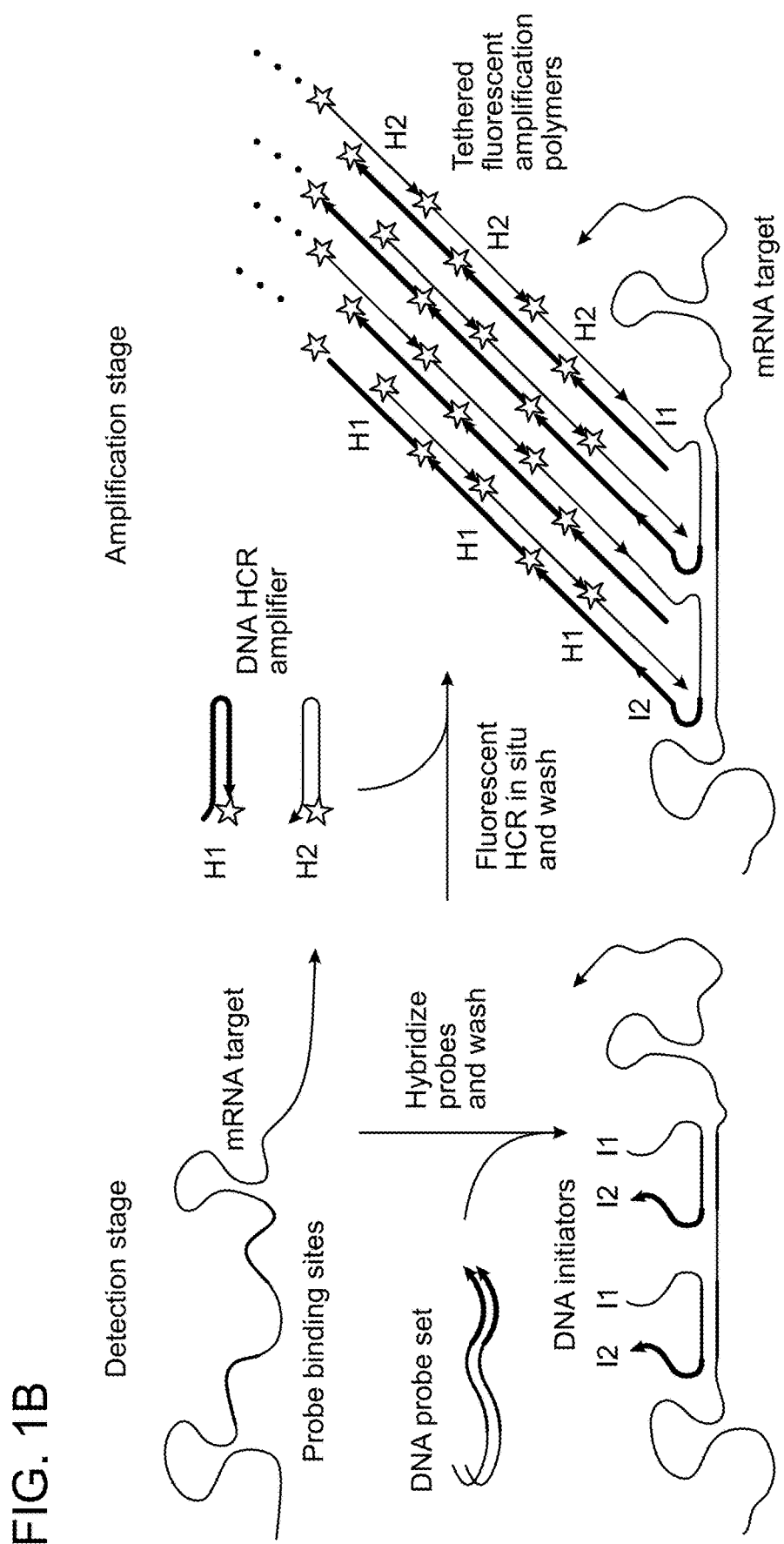
Figure 1C:
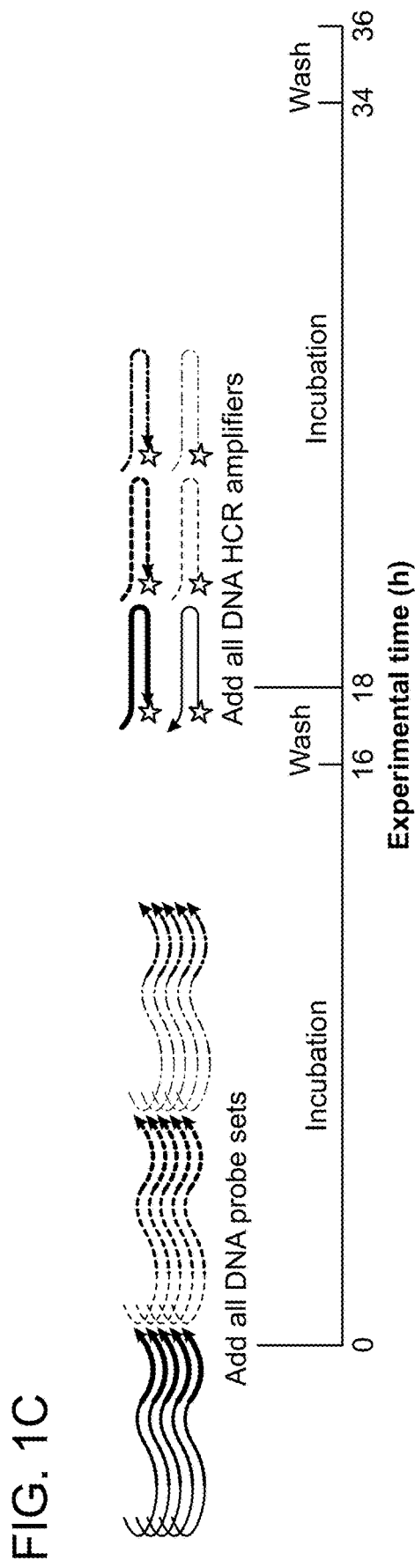
Figure 2A:
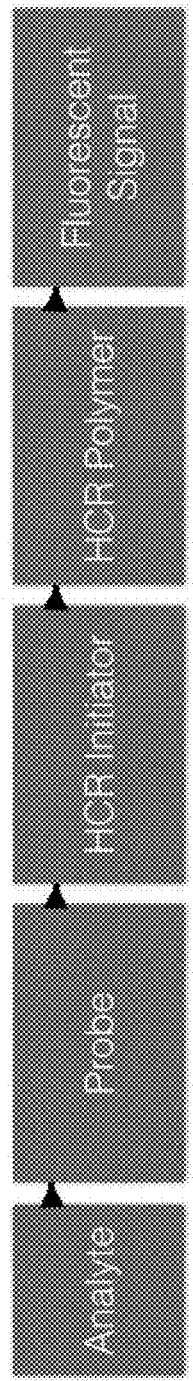
FIGS. 2A-2B depict a schematic of the information transfer steps A-D of the cyclic HCR technology. The original information as depicted in FIG. 2A is a property of the analyte being detected, such as the molecular species, a molecular quality, or a molecular configuration being interrogated. In Step A, the analyte is targeted by a probe, which specifically binds the target analyte, such that the original information of the analyte is represented by the presence of the bound probe. In Step B, the analyte information or some fraction thereof, conveyed by the probe, is transferred via a linker to the HCR initiator. The HCR initiator is associated with the probe which is associated with the analyte. The linker connects the probe to the initiator. In Step C, the analyte information or some fraction thereof, conveyed to the presence and localization of the HCR initiator, is converted into a DNA polymer by means of initiation of a hybridization chain reaction of one or more metastable HCR monomers, such as hairpins, known as an HCR polymer. Metastable HCR monomers are added to the sample and the initiator initially binds to a metastable HCR monomer and then a chain reaction of one or more remaining HCR monomers results to form the HCR polymer. In Step D, the analyte information or some fraction thereof, conveyed to the presence and localization of an HCR polymer, is converted into an amplified fluorescence signal that can be measured using a photon detector such as a microscope equipped with a digital camera. The HCR polymer is associated with one or more or a plurality of detectable moieties. These steps A-D describe the general method and the chain of information transfer in an analyte detection experiment using HCR, such as the HCR-amplified mRNA fluorescent in situ hybridization experiment depicted in FIG. 1B. Cyclic HCR is enabled specifically by methods and materials to achieve programmability of each information transfer step. "Programmability" refers to the materials and methods enabling each step of the information transfer to be either able to be gated, i.e. executed according to a pre-determined, discontinuous schedule, where the information transfer is dependent upon multiple inputs; or each step is able to be specifically reversed, i.e. where the information passed to a subsequent step in the process is selectively destroyed or removed or rendered undetectable after being detected; or each step is able to be both gated and reversible. The detectable moieties may be removable or removed from the HCR polymer, the HCR polymer may be removable or removed from the initiator, the initiator may be removable or removed from the probe and the probe may be removable or removed from the analyte. This is in contrast to the HCR reaction in FIG. 1B, in which the information transfer is continuous and non-reversible, e.g. the probe (region of sequence complementary to mRNA sequence, which binds the mRNA) is irreversibly linked with the HCR initiator and will initiate generation of an HCR polymer upon introduction of the complementary HCR hairpins. Programmability of Step C, for example, is intended to indicate that the reaction between the initiator and the HCR hairpins is gated in some way, such as by requiring another input signal other than the necessary HCR hairpins, in order for the reaction to proceed, and that formation of the HCR polymer can be reversed, such as by targeted degradation of the polymer. Programmability between information transfer steps is represented by the connector lines in FIG. 2B bearing arrows on each end.
Figure 2B:
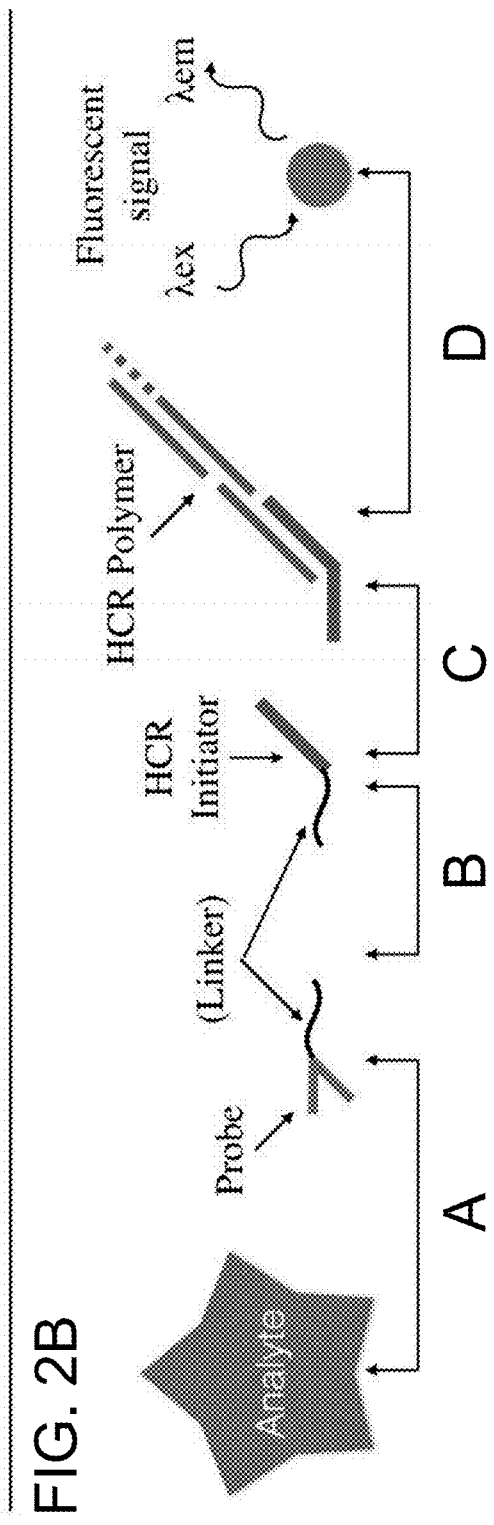

Aspects of the present disclosure are directed to generating a programmable association between target analytes and fluorescent signals generated by N orthogonal, independent, and spectrally resolvable HCR systems over a number of cycles of sequential HCR reactions to label more than N analytes, wherein the information-transferring linkages between the components of the HCR technology are made modular, i.e., shown as separate steps or activities, as shown in FIGS. 2A-2B. In FIGS. 2A-2B, the information in the analyte is broadly considered to refer to what is conveyed or represented by the particular spatial and/or temporal arrangement of atoms, molecules, compounds, or molecular complexes, which is desired to be measured, such as the molecular species, molecular quality, or molecular configuration being interrogated. During detection, this information or some fraction thereof is transferred from the target analyte to a human or computer system via labeling and detection. "Transferred" in this context refers to the information, or some fraction thereof, or some representation thereof, being conveyed via physical or electromagnetic interactions, such as by a molecular contact or photon.

The original information is a property of the analyte being detected, such as the molecular species, a molecular quality, or a molecular configuration being interrogated. The information is transferred via the analyte being contacted by a probe, which specifically binds the target analyte, such that the original information of the analyte is represented by the presence of the bound probe. The analyte information or some fraction thereof, conveyed by the probe, is transferred via a linker to the HCR initiator. The analyte information or some fraction thereof, conveyed to the presence and localization of the HCR initiator, is transferred into a DNA polymer by means of initiation of a hybridization chain reaction of one or more metastable hairpins, known as an HCR polymer. The analyte information or some fraction thereof, conveyed to the presence and localization of an HCR polymer, is transferred into an amplified fluorescence signal that can be measured using a photon detector such as a microscope equipped with a digital camera. These steps describe the chain of information transfer in an analyte detection experiment using HCR, as depicted in FIGS. 1A-1C and FIGS. 2A-2B. In the context of the present disclosure, the "chain of information transfer" may refer to the individual methods steps of associating, such as reversibly associating, a probe with a target analyte, associating, such as reversibly associating, an initiator strand with the probe, associating, such as reversibly associating, the initiator strand with metastable HCR monomers to produce an HCR polymer and associating, such as reversibly associating, the HCR polymer with one or more or a plurality of detectable labels or moieties. Each step in the process may be reversible to return to the prior step and ultimately to the original target analyte. Each step in the process may be reversed and repeated or cycled a plurality of times.

Figure 3:
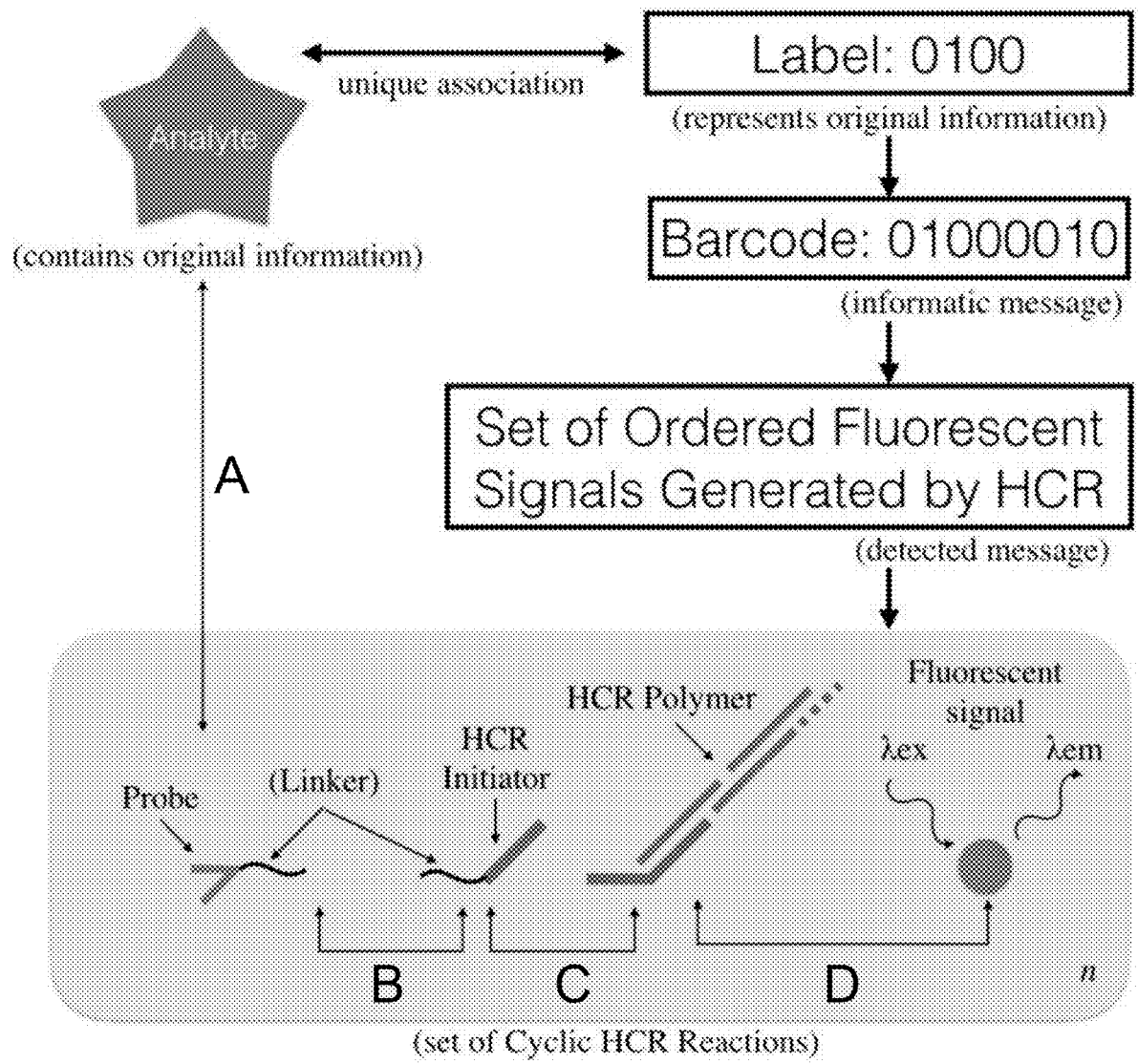
FIG. 3 depicts a schematic of the informatic and physical representations of the original information of the analyte throughout an analyte detection experiment using cyclic HCR. The original information is a property of the analyte being detected, such as the molecular species, a molecular quality, or a molecular configuration being interrogated. The original information is uniquely associated with an informatic label, referred to as the "label". The label is represented here as a binary string, but is meant to convey any symbolic representation of the original information, such as an alphanumeric value corresponding to the analyte or its original information, e.g. a gene name, or reference thereto. The informatic label is uniquely represented by an informatic message, which is conveyed via spatiotemporally organized fluorescence signals comprising the detected message. The informatic label and message may be the same, or the message may contain additional information beyond that which is strictly necessary to refer to the label, as in additional information used for the purpose of error detection or error correction. In this example, the "message" is constructed as the bit string of the label followed by the reversed bit string of the label. In detecting this message, each bit of the label will be detected twice, allowing for certain errors to be detected (e.g., if the first bit of the label is detected as "0" in the first bit of the message and then "1" as the last bit of the message, it is clear an error has occurred during transmission or detection of the message, as during probing, HCR, imaging, or image processing). The message is converted into a unique set of temporally ordered fluorescent HCR signals, which is the detected message. The temporal ordering of HCR signals is enabled by the programmability of the cyclic HCR methods and materials, designed as a set of experimental protocols and materials, e.g. Primary (Step A) Probes, Step B Probes, Step C Probes, and/or Step D probes, a microscope, other reagents, etc., and implemented experimentally.

The original information of the analyte has both informatic and physical representations throughout an analyte detection experiment using cyclic HCR, as is shown in FIG. 3. The original information is uniquely associated with an informatic label, referred to as the "label". The label can be represented as a binary string, but is meant to convey any symbolic representation of the original information, such as an alphanumeric value corresponding to the analyte or its original information, e.g. a gene name, or reference thereto. The informatic label is uniquely represented by an informatic message, which is conveyed via spatiotemporally organized fluorescence signals comprising the detected message. The informatic label and message may be the same, or the message may contain additional information beyond that which is strictly necessary to refer to the label, as in additional information used for the purpose of error detection or error correction. For example, the "message" may be constructed as the bit string of the label followed by the reversed bit string of the label. In detecting this message, each bit of the label will be detected twice, allowing for certain errors to be detected (e.g., if the first bit of the label is detected as "0" in the first bit of the message and then "1" as the last bit of the message, it is clear an error has occurred during transmission or detection of the message, as during probing, HCR, imaging, or image processing). Other methods for constructing the message including extra information for error detection and correction include repetition codes, use of parity bits, use of checksums, Reed-Solomon codes, Golay codes, and Hamming codes. The message is converted into a unique set of temporally ordered fluorescent HCR signals, which is the detected message. The temporal ordering of HCR signals is enabled by the programmability of the cyclic HCR methods and materials, designed as a set of experimental protocols and materials, e.g. Primary (Step A) Probes, Step B Probes, Step C Probes, and/or Step D probes, a microscope, other reagents, etc., and implemented experimentally.

Cyclic HCR is enabled specifically by methods and materials to achieve programmability of each information transfer step. "Programmability" refers to the materials and methods enabling each step of the information transfer to be either able to be gated, i.e. executed according to a predetermined, discontinuous schedule, where the information transfer is dependent upon multiple inputs; or each step is able to be specifically reversed, i.e. where the information passed to a subsequent step in the process is selectively destroyed or rendered undetectable, after being detected; or each step is able to be both gated and reversible.

In this context, the analyte is being interrogated using the HCR method described herein. In Step A, the analyte is targeted by a probe, which specifically binds the target analyte, such that the original information of the analyte is represented by the presence of the bound probe. In Step B, the analyte information, conveyed by the probe, or some fraction thereof is transferred via a linker to the HCR initiator. In Step C, the analyte information or some fraction thereof, conveyed to the presence and localization of the HCR initiator, is converted into a DNA polymer by means of initiation of a hybridization chain reaction of one or more metastable HCR monomers or hairpins, known as an HCR polymer. In Step D, the analyte information or some fraction thereof, conveyed to the presence and localization of an HCR polymer, is converted into an amplified fluorescence signal that can be measured using a photon detector such as a microscope equipped with a digital camera. This flow of information, also referred to as the labeling cascade, is depicted in FIGS. 2A-2B.

At each step of the flow chart from A to B to C to D, or for any subset of these steps, the process is cycled a desired number of times as further described herein. Therefore cyclic HCR is enabled by methods and materials to achieve programmability of the information transfer steps in order to cycle them a number of times. Each step can be cycled, i.e. repeated, a number of times. In preferred implementations of cyclic HCR, one or more information-transfer steps A-D (i.e., the primary probe is attached to the analyte, primary probe is functionally linked to an HCR initiator sequence, the initiator is contacted with hairpin structures, the hybridization chain reaction takes place, and the resulting polymer generates a detectable signal, which is detected, such as a fluorescent signal) are made reversible in order to allow those steps to be repeated one or more times.

"Reverse", "reversed" or "reversable" as referred to throughout the specification may refer to the removal or separation of molecules that have been joined or otherwise connected, or removal of a fluorescent moiety from the sample, or otherwise returning the sample to a state where there is no detectable moiety or activated moiety to be detected. The detectable moiety can be removed using methods described herein or as known to those of skill in the art. This allows the entire space of spectrally distinct signals to be used each round. Alternatively, the signals may be additive, in which case each round of HCR adds new signals to the existing ones. In that case, the existing signal may be subtracted computationally in order to infer the new signal. "Reverse", "reversed" or reversible" may refer to returning the sample to an earlier state, such as the sample being in state D and being modified to place the sample in step A, B, or C.

Cyclic hybridization chain reaction (CHCR) can be used for detecting one or more analytes or target molecules by designing of one or more or a plurality of HCR reactions, conducted in serial, or as sets of parallel reactions conducted in serial, for serial or combinatorial labeling of a plurality of target molecules, molecular identities, molecular qualities, or molecular compositions, such that each target is associated with a unique HCR signal or set of HCR signals over the totality of HCR reactions. Target molecules include nucleic acid polymers, such as RNA, DNA, and their analogs, amino acid polymers, including proteins, chemical modifications of any of the above, lipids, metabolites, biomolecules, and other small molecules, and molecular compositions including one or more of any of the above.

Cyclic HCR achieves multiplex analyte detection by enabling the fluorescence signals from each cycle of HCR to be combined into a composite label, or barcode, of greater information content than is contained in any individual fluorescence signal. Information is acquired, as by digital microscopy, upon the detection of fluorescence signals present within a sample. The detection timepoints of a CHCR experiment may be determined by any combination of cycling CHCR steps A-D. For example, some subset of the detection timepoints may occur during cycling Step D, i.e. cycles of associating fluorescence signal with HCR polymers tethered to target analytes via the Primary Probe and the linker, understood to be any of the non-programmable or programmable CHCR Step B methods described herein, which contains an functional HCR initiator. Another subset of detection timepoints within the same experiment may occur during cyclic of Steps B-D, i.e. by functionally linking an HCR initiator to a Primary Probe, generating a tethered HCR polymer, and detecting the amplified fluorescence signal. These subsets of timepoints may be either sequential or interleaved. The detection timepoints are determined by the design of the CHCR experiment. In any case, each distinct detection event is understood to be the acquisition of image data. Between detection events the association between the fluorescence signals generated by HCR and the target analytes is changed in some way. The association between fluorescence signals and the target analytes may be additive, in which case new fluorescence signals are added in each cycle. Alternatively, the association between fluorescence signals and the target analytes may be exchanged, such that the previous signals are abolished and new signals are established.

Composite labels constructed from time-ordered signals can vary in multiplexity, or theoretical information content. Assume in each cycle of HCR, N spectrally resolved orthogonal HCR systems are used to generate fluorescence signals. These N spectrally resolved signals may be fluorescent moieties whose emission spectra is able to be distinguished from one using techniques known to those familiar with the art, such as by using band pass filters to detect light from specific wavelengths in any particular image. Alternatively, the N spectrally resolved signals may comprise "colorimetric" combinations of fluorescent moieties. Composite labels, or barcodes, are used to label target analytes by combining the information from more than one detection event within a cyclic HCR experiment.

Exponential or combinatorial barcoding is enabled by the detection of more than one fluorescence signal per target molecule over the course of a Cyclic HCR experiment. The term "combinatorial" is used to refer specifically to the mathematical notion of permutation, which relates to the act of arranging all members of a set into some sequence or order, including partial permutations, which are ordered arrangements of k distinct elements selected from a set (when k is equal to the size of the set, these are the permutations of a set). In Cyclic HCR technology, the sequence or order is understood as the temporal ordering of fluorescence detection events over the course of a cyclic HCR experiment, such as by cycling one or more of CHCR Steps A-D. The members of the set are understood to be the set of all spectrally resolvable fluorescence signals generated by the totality of HCR systems within any single timepoint of CHCR. If each distinct HCR signal within a single timepoint is generated by one of N spectrally distinct dyes, the signals are members of this set, of size N. If all single-colors and combinations are used, there are $2^N-1$ members of the set of spectrally resolvable fluorescent signals (e.g. if we have single colors red and blue, we consider the set of distinct signals to contain the three signals red, blue, and the combined signal of red AND blue simultaneously).

The term "exponential" is used to refer specifically to the case where the barcode space grows exponentially with the number of cycles, i.e. the number of ordered detection events. For example, if a set of N distinct signals is used at each timepoint, and k timepoints are used for detection during cyclic HCR (as by cycling one or more of CHCR Steps A-D), the barcode length is understood to be k, and the space of potential barcodes is $N^k$, defining the upper limit of distinct labels able to identified, i.e. the number of target analytes able to be detected within the CHCR experiment. In this example, each target analyte is associated with a fluorescence signal at each timepoint.

In each cycle of CHCR, between 0 and 1 distinct signals are associated with each target analyte. In the case where each target analyte generates a distinct signal in exactly one timepoint during cyclic HCR, the barcoding is understood to be linear. E.g. the number of target analytes able to be labeled grows linearly by at most N distinct signals with each additional cycle. Therefore using k cycles, with N distinct signals is used at each timepoint, it is possible to detect at most N×k target analytes.

Mathematically, the upper bound of the number of target analytes able to be distinctly labeled with a composite barcode of length $\alpha$, within a Cyclic HCR experiment comprising k cycles with N distinct signals is used at each timepoint, is equal to $k/\alpha \times N^\alpha$. Using this formula, we can easily arrive at the earlier values. In the earlier case where each target analyte has a fluorescence signal at each of k timepoints, the length of the composite barcode a=k, and the formula reduces the known $N^k$. In the case where each target analyte has a fluorescence signal at exactly one timepoint in Cyclic HCR experiment with k detection timepoints, the formula reduces to k×N. It is possible to construct a Cyclic HCR experiment where each target analyte is associated with a composite label of length $\alpha$, given $1 \leq \alpha \leq k$.

This formula describes only the upper bound of the number of target analytes able to be distinctly labeled within a Cyclic HCR experiment. As described, the detected informatic message, which has length α, may contain some information beyond that which is necessary for identification of the unique target analyte label, such as information used for error detection or error correction.

In order to build a composite label, or barcode, with length greater than 1, i.e. in any case where exponential barcoding is used, it is necessary to connect the signals from the target analyte between cycles or timepoints, in order to assemble the time-ordered composite label. This is typically accomplished by fixing the target analytes in space, such as by chemical fixation of a biological sample, or by cross-linking the target analytes to a 3D matrix such as a hydrogel, to preserve the spatial organization of the target molecules between cycles of HCR. However, it is also possible to connect the signals from a target analyte by tracking the position of the target analyte over time, such that the HCR signals can be mapped to a single target analyte. For example, a tracking moiety may be affixed to a target analyte, which is detected continuously or at time intervals sufficient to track the position of the target analyte over time. At each HCR detection event, the HCR signal can then be associated with a specific target molecule. Any method that allows the HCR signals from each time point to be mapped to a particular target molecule will enable the assembly of a composite label from individual fluorescence signals.

For unique labels generated using cyclic HCR with a length equal to one, i.e. for a cyclic HCR labeling method wherein each target analyte generates exactly one amplified fluorescence signal over the totality of HCR cycles, it is not necessary to track the target analyte over time, as the single detection event conveys all of the original information and is sufficient to identify the target analyte.

When assembling composite labels under certain implementations, it may be important to detect signals associated with single target molecules. For example, if two target molecules are located spatially within a diffraction-limited distance, the fluorescence signal that they generate will be super-imposed using diffraction-limited microscopy. Therefore the composite labels for these two target molecules, if they are of a different label, will be convolved, and it may not be possible to identify the underlying composite labels from the convolved composite label. However, any number of strategies are compatible with Cyclic HCR to avoid this problem. For example, any number of existing super-resolution microscopy techniques may be used to spatially resolve the signals. These include any of the stochastic super-resolution methods, such as DNA PAINT, STORM, PALM, SOFI, and others, where objects blink stochastically, and are then localized with sub-diffraction-limited precision, as well as deterministic super-resolution microscopy methods, such as STED, SIM, and others. Aspects of the Cyclic HCR invention may enable novel methods of stochastic or deterministic super-resolution detection, as by detecting only a subset of composite labels at any one time in a Cyclic HCR experiment, then later detecting another subset, and so on, such that the concentration of target analytes in each subset is sufficiently low that all individual target molecules are spatially resolvable within each detection event (i.e. partitioning). In certain implementations, the target analytes may be physically linked to a swellable 3D matrix, such as the expanding matrix in (Science 347(6221):543-548), which physically separate target analytes such that they can be individually resolved. In other implementations, the primary probe or primary probes, linker, Step B Probe, HCR initiator, HCR polymer, or detectable label, or any physical object comprising or representing the original information being detected may be linked to the expanding matrix. Any method that enables resolving individual target molecules during detection, such that composite labels can be assembled for individual target molecules, or that enables informatic deconvolution of detected convolved composite labels, such that composite labels corresponding to individual target molecules can be recovered, are enabling for the detection of composite labels using Cyclic HCR.

Step A) Cyclic Labeling of a Plurality of Target Molecules by One or More Primary Probes.

According to methods described herein, a plurality of target molecules within a sample are each individually detected in series or, preferably, in parallel including the step of attaching one or more, or a plurality of primary probe to a target molecule. The primary probe is also referred to as the "Primary Probe", "Primary Step A Probe", or "Step A Probe." At some later time, a hybridization chain reaction of nucleic acid hairpin molecules including a detectable moiety or detectable label thereby associates a plurality of detectable moieties or detectable labels with the probe, and thereby to the target molecules. The detectable moieties or detectable labels are detected. Programmability of Step A is enabled by methods and materials to reverse the association between the target analyte and the primary probe. See FIG. 4 and FIGS. 5A-5C.

The probe(s) are responsible for the specificity of analyte detection. Each probe must form chemical bonds or molecular interactions (e.g. hydrophobicity, charge, etc.), such as affinity or reactivity associations, with target analytes. Under certain conditions, each probe has certain specificity to the target analyte, which may be degenerate. The primary probe determines the original information being detected and transmitted by virtue of the binding or reactivity profile of the probe itself, under the experimental conditions and in the context of the sample. For example, a primary probe binding to a particular protein species is considered to transfer or detect the information of the presence and identity of the protein species, and thereby can be used to measure presence, identity, number, abundance, and distribution in space or over time of that protein species. A primary probe may bind specifically to a modification or a molecular species modified in a certain way, thereby transferring information about both the presence and identity and modification state of the molecular species. A primary probe may bind specifically to a molecular species in a certain conformation, or in a certain context (e.g. local environment, sample pre-treatment). A primary probe may bind to a class of, or set of related proteins or nucleic acid molecules, thereby transferring information about the presence of one of a set of potential molecular species. A primary probe may bind with a certain kinetic on and off rate to one or more, or a plurality of spatial configurations of atoms, molecules, or molecular complexes, where the information transferred is of a probabilistic nature, where the probability of the bound molecular species being of any particular species is related to the binding and binding kinetic properties of the primary probe, the concentration and accessibility of potential targets to binding by the primary probe, and other conditions of the experiment, all or part of which may be either known, inferred, or measured in the process of analyzing the data.

Examples of primary probes include, but are not limited to DNA and RNA in situ hybridization (ISH) oligonucleotides, which contain nucleic acid sequences complementary to target nucleic acids; Nucleic acid analog probes, which bind to target nucleic acids; Immunological proteins, immune-derived proteins, or peptide fragments, such as antibodies, nanobodies, single chain variable fragments, phage-display particles, etc., which bind to target analytes including proteins, modified proteins, and other types of biomolecules; Aptamers including nucleic acid and nucleic acid analog polymer ligands which bind to target analytes; Proteins, such as lectins, which bind certain carbohydrate analytes; Other types of ligands, which exhibit any non-random binding pattern for other molecules under any conditions.

Figure 4:
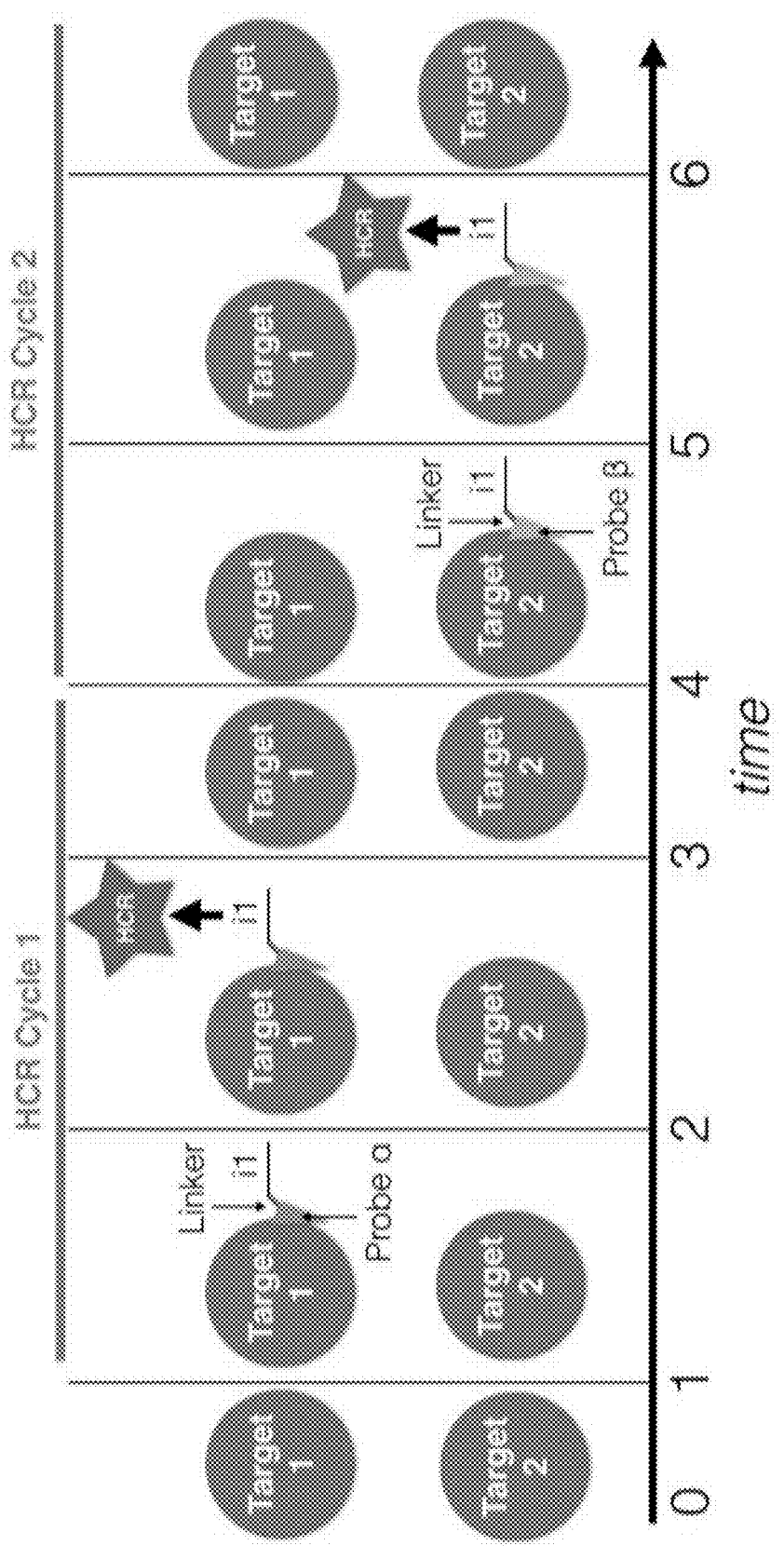
FIG. 4 depicts a schematic of programming probe binding to a target molecule over two rounds of Cyclic HCR for serial detection of two target analytes. At Time=0, two target molecules are present in a sample. At Time=1, a Primary (Step A) Probe, such as an antibody, aptamer, or DNA/RNA ISH probe, referred to as "Probe Alpha", represented as an orange triangle, cognate to the HCR initiator "i1" via a certain linker, represented as the short red line, such as a chemical bond or molecular interaction, but understood to be any kind of programmable or non-programmable linker as described by Step B of Cyclic HCR, is added to the sample and binds to Target 1. At Time=2, HCR hairpins are introduced to the sample, contact the initiator, and subsequently generate an amplified fluorescent HCR signal. At Time=3, Probe Alpha has been stripped from the sample, and the HCR polymer has also been removed using any methods described in Step C of Cyclic HCR. At Time=4, a new probe, "Probe Beta", cognate to the same HCR initiator "i1" via a certain linker, such as a chemical bond or molecular interaction, but understood to be any kind of programmable or non-programmable linker as described by Step B of Cyclic HCR, has been added to the sample and bound Target 2; At Time=5, HCR hairpins are added to the sample, contact the initiator, and subsequently generate an amplified fluorescent HCR signal. At Time=6, Probe Beta has been stripped from the sample, and the HCR polymer has also been removed using any methods described in Step C of Cyclic HCR. In this example, the same HCR fluorescence signal amplification hairpins and initiator are re-used over the two cycles of HCR to detect two target molecules in series. The first cycle of HCR is represented at Time=1 through 3, whereas the second cycle of HCR is represented at Time=4 through 6. Where detection of HCR fluorescence is represented as a binary 1, and lack of HCR fluorescence is represented as a binary 0, the detected message corresponding to Target 1 is "10", whereas the detected message corresponding to Target 2 is "01". Therefore although detection of these two molecules utilizes the same HCR fluorescence signal amplification hairpins and initiator, the ordered set of fluorescence signals constituting the detected message are unique for each target molecule.

FIG. 4 is directed to programming the interaction between the primary probes and the target analytes. FIG. 5A is directed to an example of an aptamer as the primary probe. FIG. 5B is directed to an example of an antibody as the primary probe. FIG. 5C is directed to an example of an oligonucleotide ISH primary probe.

The methods of reversibility of Step A are inherently linked to the nature of the probe. Reversibility of Step A may be accomplished by any means of reversing the chemical bonds or molecular interactions between the target analyte and the probe. For example, temperature, salt concentration, and/or denaturants such as guanidine HCl, urea, and formamide can be used to disrupt nucleic acid annealing, removing bound DNA or RNA ISH probes from a target nucleic acid molecule. Temperature, salt, and/or denaturants such as guanidine HCl, urea, and formamide can also be used to disrupt the interactions between peptide ligands such as antibodies and lectins, reversing the binding of the ligand to the target analyte. Enzymatic treatments can reverse probe binding by specifically degrading the probe, as by DNase digestion of DNA ISH probes targeting mRNA or RNA molecules, which digest the DNA probe but not the target molecule. Oligonucleotide or nucleic acid analog probes, as well as peptide probes, may be synthesized to contain chemical groups sensitive to photo-, chemical, or enzymatic treatment rendering the probe labile, as in degraded or displaced from the target molecule. For example, an antibody probe may contain non-natural amino acid residues with cleavable groups in the backbone of the amino acid polymer, causing the antibody to be specifically degraded. A nucleic acid or nucleic acid analog primary probe may contain modified bases or a modified sugar backbone, such as a 3' or 5' bridging phosphorothioate linkage, which is cleaved by Ag ion, or a photocleavable group, which is cleaved by UV light, or a photolabile group, which changes atomic conformation upon treatment by UV light altering the conformation of the oligonucleotide to disrupt nucleic acid annealing. Introduction of azobenzene-containing guanidinium derivatives (Bergen et al 2016 ACS Nano Letters.) can function as a photosensitive intercalator for photoreversible nucleic acid annealing, disrupting the probe binding from a target nucleic acid.

After reversing the chemical bonds or molecular interactions between the target analyte and the probe, in which case the probe is either unbound or specifically degraded, the probe or probe fragments are removed from the sample, such as by washing. At least some portion of target analytes, however, remain intact and able to be probed in subsequent cycles of Cyclic HCR.

For example, by specific degradation of DNA ISH probes using DNase, the target mRNA molecules remain intact and able to be re-probed using the same or a new set of primary probes. In another example, protein targets are probed in one cycle of HCR; later, the protein target probes are removed from the proteins by treatment with a denaturant such as urea, and the primary probes are washed away. The target proteins can then be re-probed using the same or a new set of primary probes. Alternatively, subsequent cycles of Cyclic HCR may target other types of molecules such as nucleic acids, which are not affected by the probing or removal of protein probes, i.e. the forward and reverse mechanisms of Step A programmability.

The labeling of the analyte of interest in each cycle of HCR may be reversed or undone or the primary probe may be otherwise separated from the target molecule, e.g. by stripping a hybridized nucleic acid probe from the target nucleic acid, such as by heating or by using a denaturant (e.g. urea, or formamide), or by enzymatic digestion of the hybridized nucleic acid probe as by DNase I digestion of DNA probes bound to RNA molecules, which are not degraded by the DNase enzyme. A bound antibody may be stripped by heat or chemical treatment (e.g. formamide). Note, however, that reversing the labeling of the target analyte does not necessarily remove the HCR polymer and associated fluorescent signal; therefore these methods may be combined with methods for reversing steps C and D. For example, disruption of the annealing between a nucleic acid ISH probe and target nucleic acid by triggering a conformation change of the primary probe containing one or more photolabile groups will not necessarily remove the HCR polymer itself, which may not contain the photolabile groups and therefore will remain polymerized, although now disconnected from the target molecule. Therefore this reversal of Step A could be combined with a reversal of Steps B, C, and/or D to facilitate removal of the HCR initiator, HCR polymer, or fluorescence signal associated with the HCR polymer, such that the sample is returned to a state suitable for subsequent rounds of detection using Cyclic HCR.

Any number of orthogonal cycling systems for Step A may be combined to programmatically render a subset of the Primary Probes bound or unbound within a cycle. For example, a subset of Primary Probes may be cycled using photo-labile groups, while others are cycled simultaneously or in series by use of chemically-labile groups to remove the Primary Probe.

A Cyclic HCR reaction may not utilize Step A programmability, as in the case where all of the desired plurality of target molecules are probed with a primary probe simultaneously and exactly once, and Cyclic HCR reactions using programmability of any of Steps B-D are conducted. In this case, the probe is never removed from the target molecule.

Step B) Programmable Functional Linkage of the Primary Probe to an HCR Initiator According to methods described herein, a plurality of target molecules within a sample are detected including the steps of attaching a probe or set of probes to each of a plurality of target molecules, such that all of the desired plurality of target molecules, or some desired subset thereof, have a probe or set of probes attached thereto, wherein each probe is capable of transferring information via Cyclic HCR Steps B-D, namely functional linkage to an HCR initiator, initiation of an HCR polymerization reaction, and generation of an amplified fluorescence signal by the HCR polymer. Functional linkage between the primary probe and the HCR initiator is intended to describe both the physical linkage, comprised of chemical bonds and molecular interactions, between the primary probe and the HCR initiator, and the state of the HCR initiator as gated or ungated, e.g. able to initiate HCR under appropriate conditions and in the presence of the complementary HCR monomers such as hairpin(s). Functional linkage between the primary probe and the HCR initiator may be programmed by either controlling the physical linkage between the primary probe and the HCR initiator, such that a physical linkage may be established and/or specifically dissolved; or by gating the HCR initiator such that the initiator may be specifically rendered capable of initiating HCR under appropriate conditions and in the presence of the complementary hairpin(s) and/or specifically rendered incapable of initiating HCR under appropriate conditions and in the presence of the complementary hairpin(s); or both.

A programmable functional linkage between the primary probe and the HCR initiator is enabled by use of a secondary probe to physically link the HCR initiator to the primary probe, referred to as the "Step B Probe". A Step B Probe including an initiator molecule bound to a nucleic acid sequence complementary to an attachment moiety (if it is a nucleic acid sequence) or binding pair of the attachment moiety of the Step A Probe is added to the sample and the Step B probe binds to the Step A probe bound to the target molecule. Corresponding hairpin molecules are then added and a hybridization chain reaction is carried out as described herein. In this manner, each target molecule within the sample is bound to a Primary Step A Probe having a secondary binding site for a Step B Probe. A Step B probe, which contains the HCR initiator motif, is used to bind or associate the same or one of a common set of initiator sequence(s) to each of the target molecules over the course of a Cyclic HCR experiment. In this manner, the same or common initiator sequence and hairpin sequences can be used during each detection step, or for detection of each target molecule in the plurality of target molecules. The detectable moieties or detectable labels are detected. The Step B probe, which contains the HCR initiator motif, may later be stripped, removed, or otherwise disassociated from the Primary Step A Probe, such that the Step A Probe is no longer physically linked to an HCR initiator and therefore is considered "reversed" or "reset" or unable to initiate an HCR polymerization reaction. In this manner, the function of the system to detect a target molecule is reversed, i.e. returned to an earlier state, so that a second analyte or subset of target analytes can be detected. The process is then repeated for a second and subsequent target molecule or subset of target molecules, using one or more Step B Probe(s) specific for the binding moiety of the Step A probes of the next target molecule or set of target molecules, but where the Step B Probes have the same HCR initiator sequence(s) and the same detectable moiety or detectable label that was used with the first target molecule or set of target molecules. In this manner, the same initiator and hairpin molecules can be used, i.e., "re-used" for each target molecule.

According to certain aspects, methods and materials are provided for forming a chemical bond (ionic, covalent, or hydrogen) between the Primary Step A Probe (i.e., the primary probe responsible for binding the target analyte, but also with the secondary attachment site for attachment to the Step B Probe, which contains the HCR initiator sequence) and the Step B probe with the HCR initiator. These methods include Sequencing by hybridization, e.g. annealing a nucleic acid Step B probe to a complementary sequence on the Primary Step A Probe, as in FIG. 7B; Sequencing by ligation, as in FIG. 7C, to form a stable duplex nucleic acid or nucleic acid analog linking the HCR initiator sequence in a Step B Probe to a Step A Probe; or Use of a ligand conjugated to an HCR initiator sequence as a Step B probe, as by an antibody, aptamer, or protein ligand, which specifically binds an epitope present on the Step A probe, e.g. a streptavidin-modified HCR initiator sequence which binds to a biotinylated Primary Probe.

Further methods and materials are provided for disrupting a chemical bond (ionic, covalent, or hydrogen) between the Primary Step A probe and the Step B probe, or for in any way severing the physical linkage or association between the Primary Probe and the HCR initiator sequence. These methods include Methods for disrupting the bond between annealed nucleic acids or nucleic acid analogs by means of temperature, salt concentrations, denaturants (urea, formamide, guanidine HCl); or Step B Probe materials and methods for introducing a photo-labile, chemically-labile, or enzymatically-labile group anywhere in the portion of Step B Probe that binds the Step A Probe, such that the binding is disrupted upon induction, as by light treatment or introduction of a chemical or enzymatic agent, e.g. a photolabile group, which changes conformation upon treatment by UV light altering the conformation of the oligonucleotide to disrupt nucleic acid annealing between the Step A Probe and the Step B probe; Step A Probe materials and methods for introducing a photo-labile, chemically-labile, or enzymatically-labile group anywhere in the portion of Step A Probe that binds the Step B Probe, such that the binding is disrupted upon induction, as by light treatment or introduction of a chemical or enzymatic agent, e.g. a photolabile group, which changes conformation upon treatment by UV light altering the conformation of the oligonucleotide to disrupt nucleic acid annealing between the Step A Probe and the Step B probe; Step B Probe materials and methods for introducing a photo-labile, chemically-labile, or enzymatically-labile group anywhere between the portion of Step B Probe that binds the Step A probe and the HCR initiator, such that the physical linkage is broken and the HCR initiator sequence(s) can be washed away or removed; e.g. introduction of a 3' or 5' bridging phosphorothioate linkage in the backbone of a DNA oligonucleotide between the region complementary to the Step A Probe and the HCR initiator sequence; Step A Probe materials and methods for introducing a photo-labile, chemically-labile, or enzymatically-labile group anywhere between the portion of Step A Probe that binds the target analyte and the portion that binds the Step B Probe, such that the physical linkage is broken and the HCR initiator sequence(s) can be washed away or removed; e.g. introduction of a 3' or 5' bridging phosphorothioate linkage in the backbone of a DNA oligonucleotide between the region complementary to the Step B Probe and the region of the Step A Primary probe that contacts the target analyte; Step B Probe materials and methods for specifically degrading the Step B probe or the portion thereof either containing the HCR initiator or responsible for binding to the Step A Probe; e.g. DNase digestion of a DNA Step B probe, where the Step A probe is protected from the DNase activity by means of a modified base, such that the Step B probe is specifically degraded; Materials and methods for specifically degrading at least the portion of the Step A probe containing the binding moiety responsible for binding to the Step B Probe; e.g. DNase digestion of a DNA conjugated to a peptide Step A Probe.

According to one aspect, methods include cycling step B by simultaneously labeling a number of target analytes, such that each analyte is associated with one or more primary probes, but none of the primary probes are inherently HCR initiators. Systematically, subsets of the primary probes are associated with HCR initiators, as by sequencing by hybridization or sequencing by ligation. In the former case, nucleic acid probes complementary to a sequence contained in the primary Step A probe and also bearing an HCR initiator sequence are hybridized to the sample. In the latter case, DNA ligase is used to covalently extend a second-strand of DNA partially complementary to a Primary probe sequence but also bearing an HCR initiator sequence.

The association of the Primary probe with the HCR initiator may be reversed, i.e. the Step A probe and the HCR initiator may be separated, e.g. by stripping the hybridized nucleic acid probe bearing the initiator sequence, referred to as the Step B Probe, from the Step A probe. The HCR polymer may be displaced and the nucleic acid bearing the HCR initiator domain capped, such as by toehold strand displacement. See *Nature Chemistry* 3:103-113 (2011) hereby incorporated by reference. The nucleic acid bearing the HCR initiator domain may be chemically cleaved, such as by silver nitrate reaction with a bridging sulfur phosphorothioate linkage located between the chemical bonds between the linking probe and the HCR initiator sequence. A DNA strand bearing the HCR initiator domain may be enzymatically or chemically degraded, as by lambda exonuclease digestion of a 5'-phosphate bearing DNA strand, ds-specific DNase, or as by USER system (UDG/EndoVIII) or EndoV digestion of DNA containing dU and dI nucleobases, respectively. Alternatively, an endonuclease may cut the initiator sequence. Reversing the association between the HCR initiator and target may not necessarily remove the HCR polymer and associated fluorescent signal; therefore these methods may be combined with methods for reversing steps C and D.

Figure 7A:
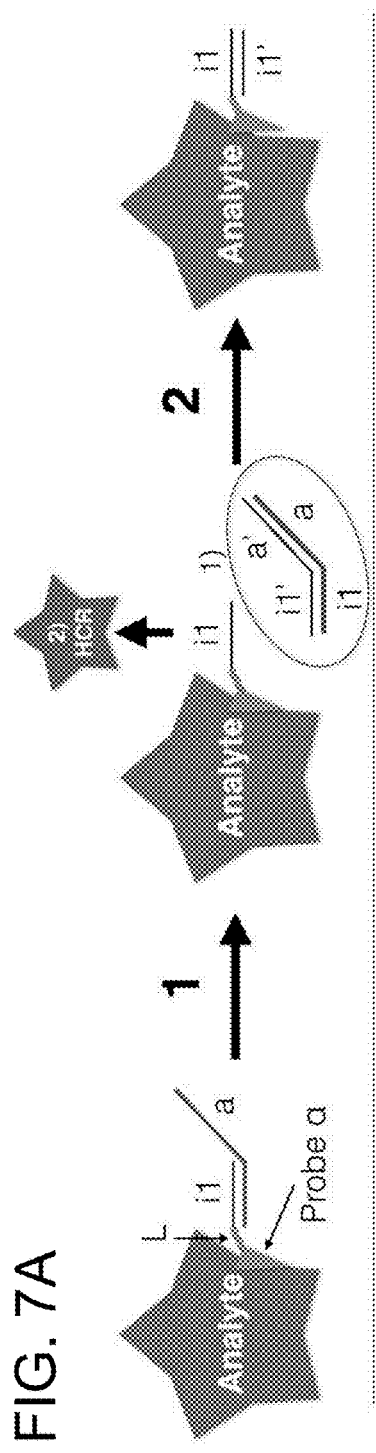
FIGS. 7A-7C depicts a schematic representation of methods of programming Step B of Cyclic HCR.
Figure 7B:
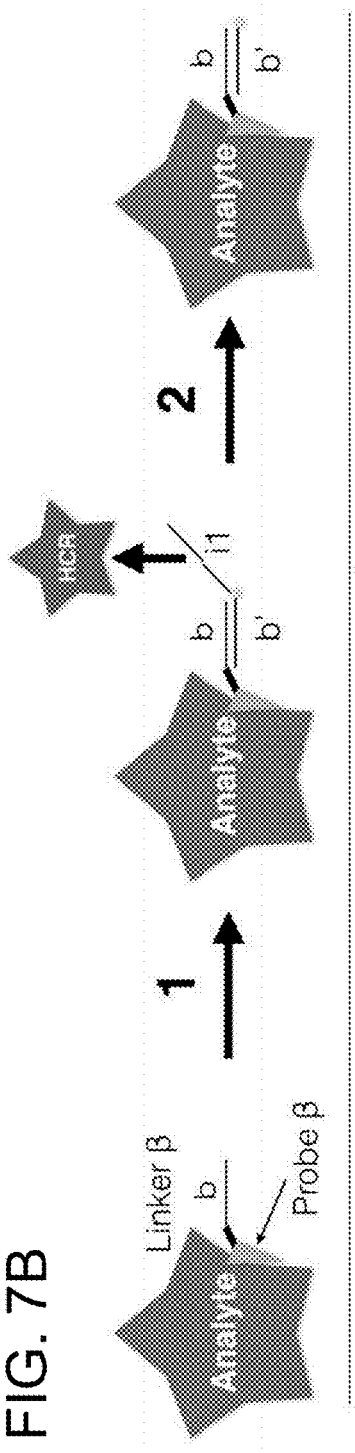

Furthermore, a programmable functional linkage between the primary probe and the HCR initiator is enabled by only methods and materials to specifically dissolve the linkage between the Primary Probe and the HCR initiator, or for in any way severing the physical linkage or association between the Primary Probe and the HCR initiator sequence. In one implementation, the Primary Probe contains a functionally active HCR initiator. Corresponding hairpin molecules are then added and a hybridization chain reaction is carried out as described herein. At a later time, the HCR initiator on the Primary Probe is physically separated from the Primary Probe, or otherwise degraded. FIG. 7B Step 2 is directed towards the removal of the functional initator from the Primary Probe, independent of use of FIG. 7B Step 1. New Primary Probes may be added to the sample, introducing the same HCR initiator sequences. In this manner, each target molecule may be associated with the same or one of a common set of initiator sequence(s) over the course of a Cyclic HCR experiment. In this manner, the same or common initiator sequence and hairpin sequences can be used during each detection step, or for detection of each target molecule in the plurality of target molecules. The detectable moieties or detectable labels are detected. Methods and materials for specifically dissolving the linkage between the Primary Probe and the HCR initiator include all those listed above. Where the linkage between the Primary Probe and the HCR initiator include any of the linkage methods described in Step A, these are also understood to be included in Step B; e.g. use of any ligand to bind a Step B Probe to a Step A probe, and any method of dissolving that linkage.

Furthermore, a programmable functional linkage between the primary probe and the HCR initiator is enabled by methods and materials for gating an HCR initiator physically linked to the Primary Probe. Step B may be programmed by gating the HCR initiator such that the ability of the Primary Probe to initiate HCR is modulated by some external input. Step B may be programming by materials and methods to gate an HCR initiator such that it is dependent on another input, such as any kind of physical or electromagnetic signal or use of an atomic or molecular activator, to initiate HCR; or by methods and materials to gate an HCR initiator such that an input, such as any kind of physical or electromagnetic signal or use of an atomic or molecular activator, inactivates the HCR initiator such that it can no longer initiate an HCR polymerization reaction; or both. A Primary Probe including a gated HCR initiator molecule is added to the sample and bound to the target molecule. At a later time, the HCR initiator may be activated, HCR monomers such as hairpins are added to sample and contact the active initiator, generate an HCR polymer, and a detectable moiety, such as a fluorescent moiety, is detected. At a later time, the HCR initiator may be inactivated, such that hairpins are added to the sample, but either cannot contact the initiator or otherwise contact the inactive initiator but do not cause a polymerization reaction.

In one implementation, the Primary Probe contains a functionally active HCR initiator. Corresponding hairpin molecules are then added and a hybridization chain reaction is carried out as described herein. At a later time, the HCR initiator on the Primary Probe is gated, or rendered unable to initiate an HCR polymerization reaction. New Primary Probes may be added to the sample, introducing the same HCR initiator sequences, or existing Primary Probes already present in the sample, but whose HCR initiator sequences are gated and unable to initiate HCR may be then ungated and rendered able to initiate an HCR polymerization reaction. In this manner, each target molecule may be associated with the same or one of a common set of initiator sequence(s) over the course of a Cyclic HCR experiment. In this manner, the same or common initiator sequence and hairpin sequences can be used during each detection step, or for detection of each target molecule in the plurality of target molecules. The detectable moieties or detectable labels are detected.

In another implementation, the Primary Probe contains an inactive or gated HCR initiator sequence, incapable of initiating an HCR polymerization reaction. All or some subset of the HCR initiator sequences on the Primary Probes are ungated, Corresponding hairpin molecules are then added and a hybridization chain reaction is carried out as described herein. According to one aspect, subsequent cycles of HCR, other subsets of the HCR initiator sequences are ungated, creating an additive HCR signal at each cycle. According to another aspect, the HCR initiator on the Primary Probe is either physically separated from the Primary Probe, or otherwise degraded, or gated, or rendered unable to initiate an HCR polymerization reaction, such that subsequent HCR cycles create new signals in the absence of previous signals. In this manner, new Primary Probes may be added to the sample, introducing the same HCR initiator sequences, or existing Primary Probes already present in the sample, but whose HCR initiator sequences are gated and unable to initiate HCR may be then ungated and rendered able to initiate an HCR polymerization reaction. In this manner, each target molecule may be associated with the same or one of a common set of initiator sequence(s) over the course of a Cyclic HCR experiment. In this manner, the same or common initiator sequence and hairpin sequences can be used during each detection step, or for detection of each target molecule in the plurality of target molecules. The detectable moieties or detectable labels are detected.

Methods of gating the HCR initiator include Methods of introducing a protecting moiety on the HCR initiator, such that it is unable to initiate an HCR polymerization reaction; Methods of protecting the HCR initiator with a complementary strand, such that it is inaccessible to initiate the HCR polymerization reaction, as in FIG. 7A; Where the protecting strand contains additional sequence, such that a complementary strand can be introduced (also referred to as Step B Probe, as it is responsible for programming the functional linkage between the Primary Probe and the HCR initiator), such that toehold strand displacement occurs, causing the HCR initiator sequence(s) to be single-stranded and/or made available to initiate an HCR polymerization reaction; Methods and materials for introducing and/or removing a photolabile, chemically-labile, or enzymatically-labile protecting moiety on the HCR initiator, such that it is unable to initiate an HCR polymerization reaction; Methods for specifically activating an HCR initiator, or for specifically deactivating an HCR initiator, such as by the addition or removal of a binding moiety, such as a ssDNA binding protein, which blocks the ssDNA initiator sequence from contacting the HCR hairpins; Methods and materials for a chemically-, photo-, or enzymatically-labile HCR initiator sequence and use thereof, such that the atomic conformation of the HCR initiator is able to be modulated to allow the HCR initiator to either contact or be prevented from contacting the HCR hairpins; Methods are provided to cycle step B by protecting and/or de-protecting the initiator sequence, as by double stranding the initiator sequence with a complementary protecting strand. The complementary protecting strand may be displaced as by DNA toehold strand displacement. The protecting strand may be chemically cleaved, such as by silver nitrate reaction with bridging sulfur phosphorothioate linkages along the backbone of the protecting strand. The protecting strand may be enzymatically or chemically degraded, as by lambda exonuclease digestion of a 5'-phosphate bearing DNA strand, ds-specific DNase, or as by USER system (UDG/EndoVIII) or EndoV digestion of DNA containing dU and dI nucleobases, respectively. The protecting strand may be forced to un-hybridize by incorporating photolabile bases that change atomic configuration upon exposure to different wavelengths of light.

Broadly, the functional linkage between the Primary Probe, or region thereof, that is responsible for contacting and binding the target analyte, and the HCR initiator sequence(s), are described as "the linker," "linker," "functional linker", "Step B Linker," or "programmable linker". In the case of Cyclic HCR using Step B programmability, any of the aforementioned methods and materials constitute the linker, e.g. the combined binding moities of the Step A Probe and the Step B Probe, which establish a physical linkage between the Primary Probe and the HCR initiator, or the Step A Probe containing a gated or gate-able HCR initiator.

A Cyclic HCR reaction may not utilize Step B programmability, as in the case where all primary probes are directly cognate to an ungated HCR initiator, e.g. an HCR initiator that will initiate an HCR polymerization reaction in the presence of the complementary hairpin(s) and in a suitable environment (e.g. aqueous buffer, temperature, etc.). In this case, the functional linkage of the primary probe to an HCR initiator may be by direct chemical linkage, e.g. a DNA HCR initiator conjugated directly to an antibody primary probe (e.g. Solulink); or as by the phosphodiester bond in the backbone of a nucleic acid between the region of a nucleic acid or nucleic acid analog primary probe complementary to a target nucleic acid molecule and the region containing the HCR initiator motif; or as by a non-reactive spacer sequence, e.g. poly-T, poly-A, or poly-[TA] repeat between the region of a nucleic acid or nucleic acid analog primary probe complementary to a target nucleic acid molecule and the region containing the HCR initiator motif. In these examples, the physical linkage between the probe and the ungated HCR initiator is direct and the functional linkage, which refers to both the physical linkage and the state of the HCR initiator as being gated or not, is also direct, and not designed in any way to be capable of being physically separated or gated; therefore Step B is not programmable. These are also referred to "the linker". Cyclic HCR reactions may still utilize programmability of any of Steps A, C, and D.

Any number of orthogonal Step B strategies may be combined to programmatically render a subset of the initiator domains accessible and functional within a cycle. For example, a subset of Primary Probes may be present within a cycle with HCR initiators gated by a protecting strand, while a distinct subset of Primary Probes do not contain an HCR initiator, but rather a sequence complementary to a Step B probe containing the HCR initiator.

Figure 6:
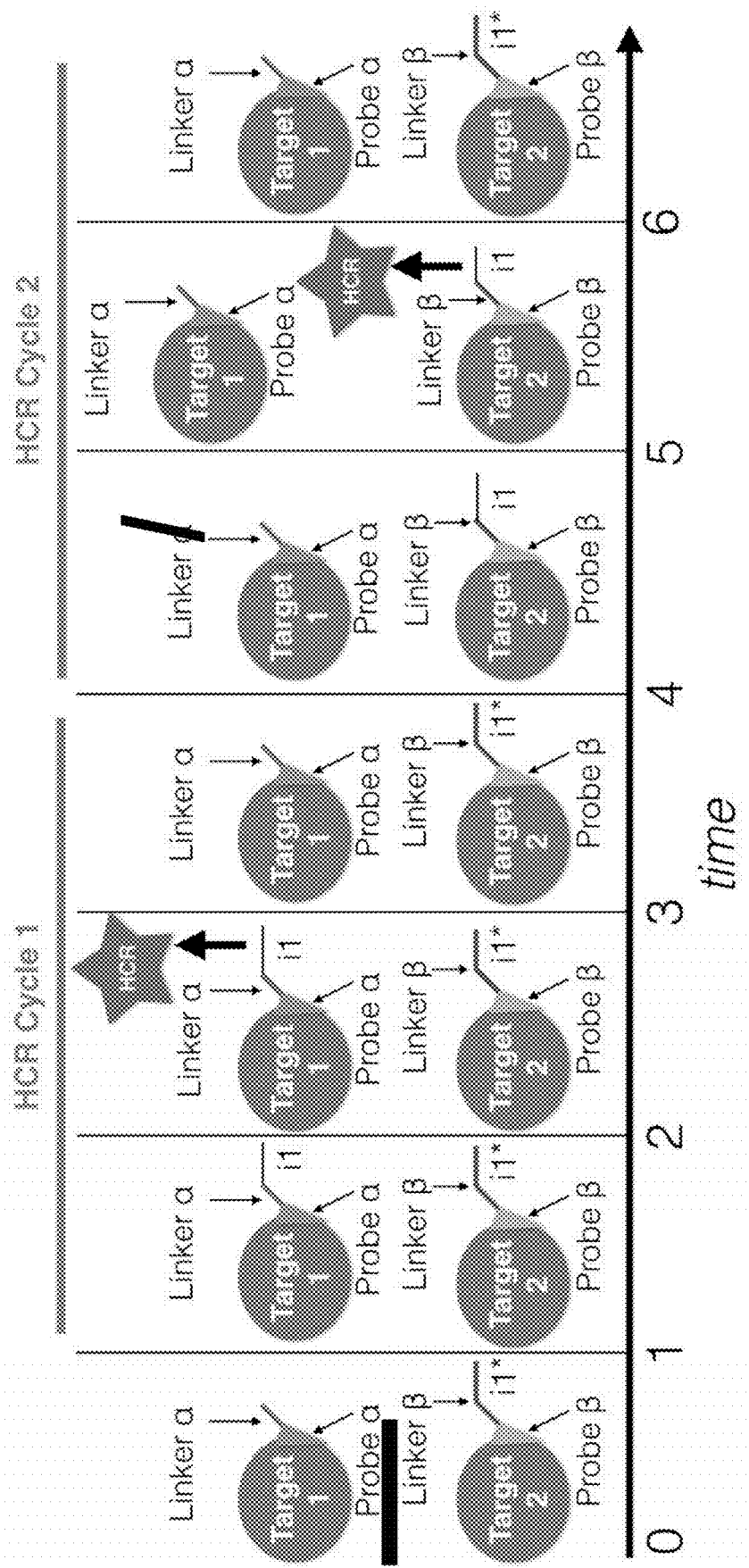
FIG. 6 depicts a schematic of programming the functional linkage between the primary probe and the HCR initiator sequence "i1" for serial detection of two target analytes over two serial rounds of Cyclic HCR, utilizing both methods of Step B, i.e. programming the physical association of the HCR initiator to the Primary Probe by means of a Step B Probe, and programming the state of a gated HCR initiator. At Time=0, two target analytes are present and have been bound by primary probes, which also contain a linker motif but not a functional HCR initiator sequence. Target 1 has been bound by "Probe Alpha", which also contains a binding moiety referred to as "Linker Alpha." Target 2 has been bound by "Probe Beta", which is attached to a gated inactive HCR initiator "i1*", referred to as "Linker Beta." At Time=1, a Step B Probe containing complementary binding moiety to the binding moiety of Linker Alpha, such as a complementary nucleic acid sequence, is bound to Linker Alpha, and also contains the HCR initiator sequence "i1"; At Time=2, HCR hairpins are added, which generates an amplified fluorescence HCR signal which is detected. At Time=3, the HCR fluorescence signal from Time=1 has been removed using methods and materials described in Step C herein, and the Step B Probe has been removed or separated from Primary Probe Alpha, by methods described herein, and washed from the sample. At Time=4, the gated HCR initiator sequence contained in Linker Beta of Primary Probe Beta is activated, such as by use of an input signal. At Time=5, HCR hairpins are added, which generates an amplified fluorescence HCR signal which is detected. At Time=6, the HCR fluorescence signal from Time=1 has been removed using methods and materials described in Step C herein, and the HCR initiator present in Linker Beta has been inactivated. In this way the HCR system corresponding to initiator sequence "i1" has been used in series for detection of two target analytes. The first cycle of HCR is represented at Time=1 through 3, whereas the second cycle of HCR is represented at Time=4 through 6.
Figure 7C:
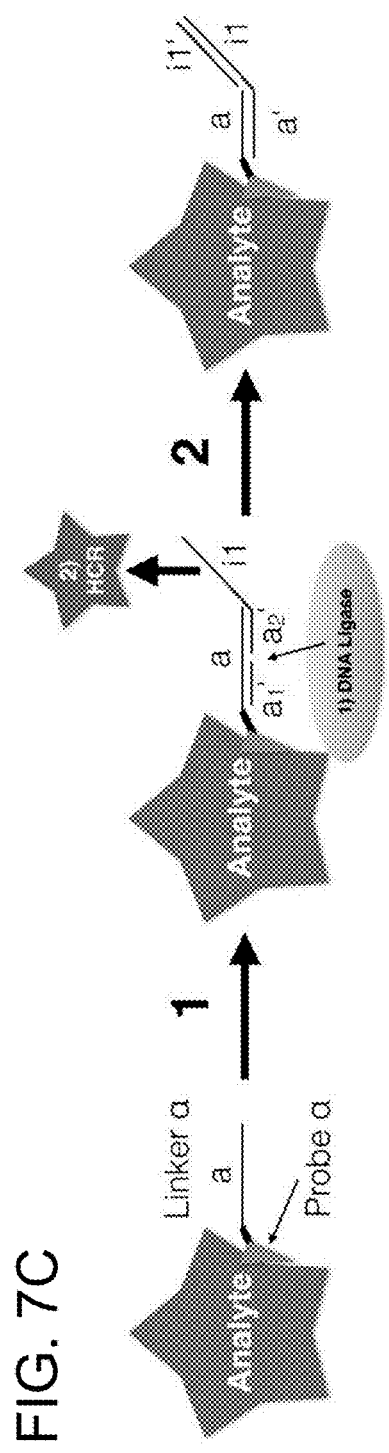

FIG. 6 is directed to the use of both methods of Step B, i.e. programming the physical association of the HCR initiator to the Primary Probe by means of a Step B Probe, and programming the state of a gated HCR initiator, for detection of two target analytes using two cycles of HCR. FIGS. 7A-7C are directed to mechanisms of programming the functional linkage between the Primary Probe and the HCR initiator, wherein FIG. 7A is exemplary of use of a gated HCR initiator, and FIGS. 7B and 7C are exemplary of programming a physical linkage between the Primary Probe and the HCR initiator, using Sequencing by Hybridization (7B) and Sequencing by Ligation (7C) reactions.

Step C) Cyclic HCR Polymerization

According to methods described herein, a plurality of target molecules within a sample are detected including the steps of attaching one or more, or a plurality of Primary probe(s) to each of a plurality of target molecules, such that at some predetermined time during the Cyclic HCR method, each of the desired plurality of target molecules has a Primary probe or set of Primary probes attached thereto, wherein each Primary probe is functionally linked at some predetermined time to an HCR initiator. Metastable HCR monomers, such as Hairpin molecules, which correspond and bind to, and which may be unique to, an initiator are added and a hybridization chain reaction is carried out as described herein, generating a tethered HCR polymer at the site of the initiator. The HCR polymer is "tethered" to the extent that the initial HCR monomer is hybridized or bound to the initiator and remaining HNR monomers are extended in series to make the HCR polymer. At some predetermined time, the tethered HCR polymer is labeled by one or more, or a plurality of fluorescent or detectable moieties. In this manner, each target molecule within the sample is bound to a probe having an HCR initiator and HCR monomers such as hairpin molecules are added to detect the target molecule. This process can be conducted in series or in parallel for each target molecule in the sample over time. Each target molecule may be bound to a probe having an HCR initiator, where HCR monomers such as hairpin molecules are subsequently added to detect the target molecule, one or more times over the course of a Cyclic HCR method. Over the entire course of a Cyclic HCR method, each analyte, or each unique aspect of original information being interrogated, such as a molecular species, molecular quality, or molecular configuration, generates a unique pattern of ordered amplified fluorescence signals via Cyclic HCR. For Cyclic HCR, the HCR hairpin molecules and associated or cognate initiator sequence may be degenerate to each target molecule. Within an ordered set of HCR polymerization reactions, the same or a common set of HCR polymers may be used repeatedly, with the HCR polymers being functionally reversed between HCR polymerization reactions, as by reversal of the polymerization or otherwise by degradation or detachment of the HCR polymer. In this manner a single HCR system, or a set of orthogonal HCR systems, can be used to detect all of the plurality of target molecules in the sample. The ability to form and degrade or detach an HCR polymer is enabled by materials and methods described herein, which functionally reset the sample between each HCR polymerization reaction, allowing the HCR system(s) to be re-used between cycles of Cyclic HCR.

Figure 9:
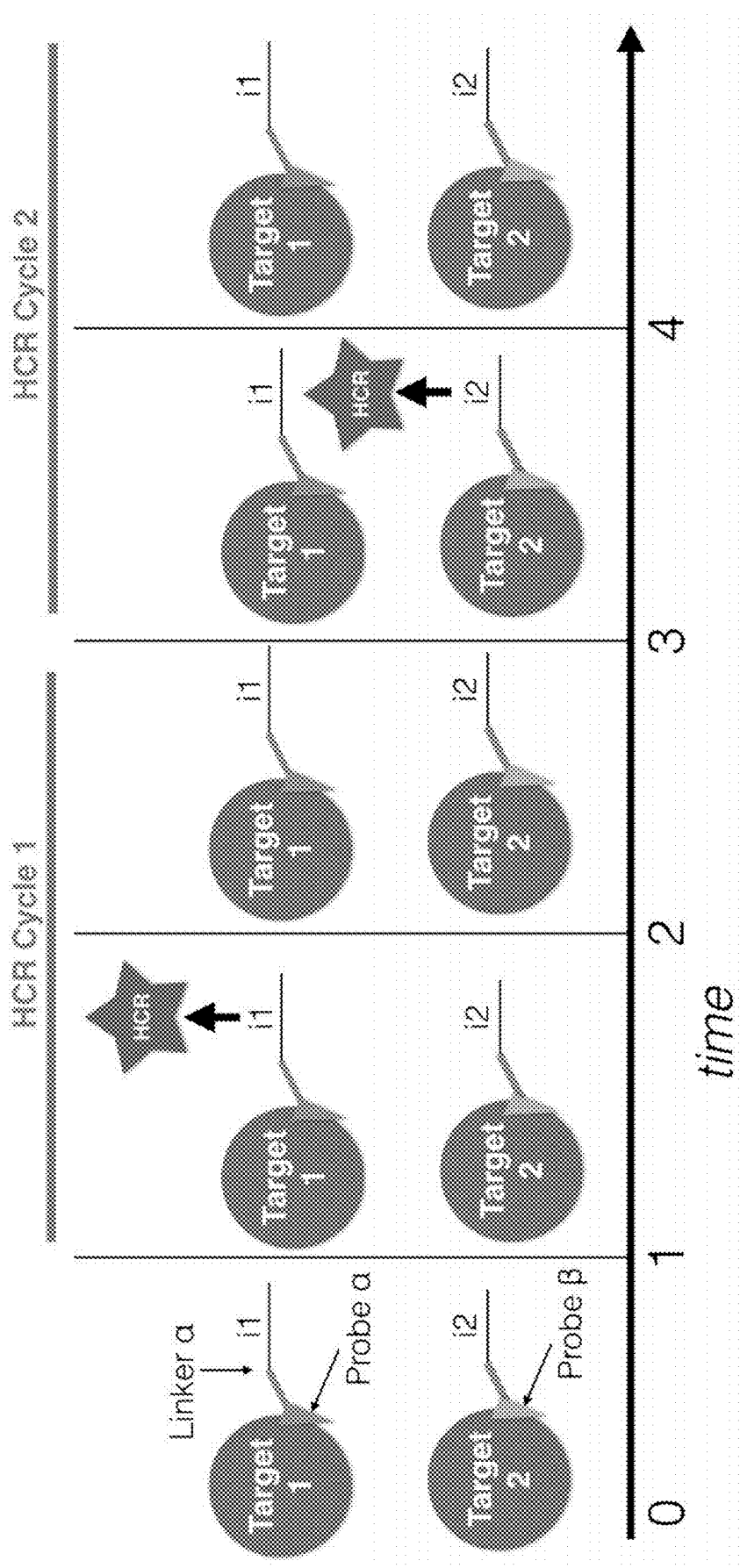
FIG. 9 depicts a schematic of programming Step C, the HCR polymerization reaction. At Time=0, two target molecules are present. Target 1 has been bound with Primary Probe "Alpha," which is functionally linked to HCR initiator sequence "i1" via "Linker Alpha". Target 2 has been bound with Primary Probe "Beta," which is functionally linked to HCR initiator sequence "i2", understood to be via a linker. The linker may be a covalent linkage or a programmable linkage using the methods described herein as Step B programmability. At Time=1, HCR hairpins cognate to initiator "i1" are added to the sample, and "i1" is contacted by the cognate HCR hairpins forming an HCR polymer, represented by the red star indicating a red fluorescence signal, which is detected. The HCR polymer is subsequently degraded or disassembled at Time=2, thereby returning the sample to a prior state without HCR polymers. At Time=3, HCR hairpins cognate to initiator "i2" are added to the sample, and "i2" is contacted by the cognate HCR hairpins forming an HCR polymer, represented by the red star indicating the same red fluorescence signal, which is detected. The HCR polymer is subsequently degraded or disassembled at Time=4, thereby returning the sample to a prior state without HCR polymers. The first cycle of HCR is represented at Time=1 through 2, whereas the second cycle of HCR is represented at Time=3 through 4.
Figure 11:
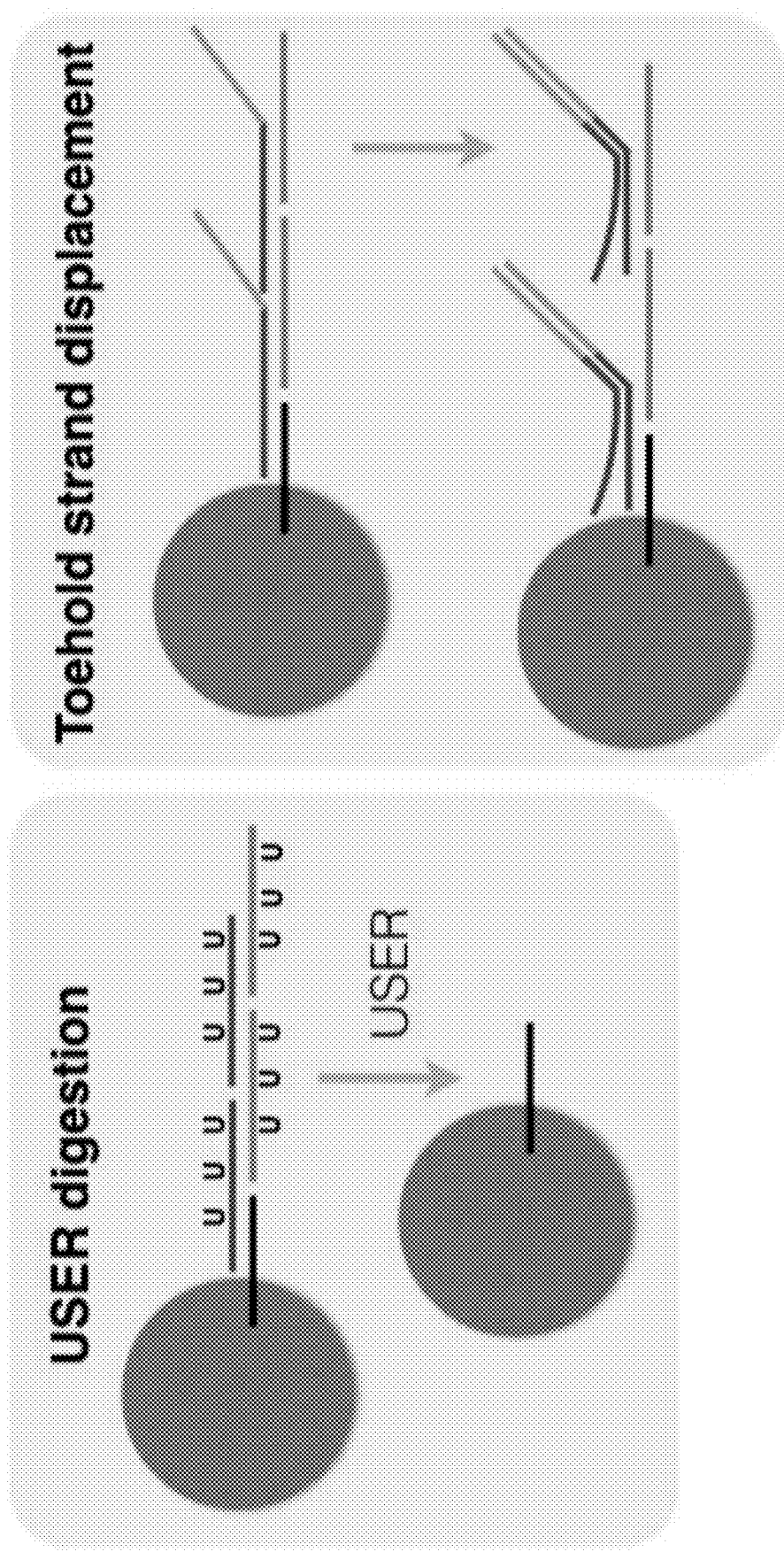
FIG. 11 further depicts a diagram of a reversible HCR polymerization example. Left) An HCR polymer, where the constituent monomer strands bear dU nucleobases, is enzymatically degraded by USER enzyme reaction, which combine UDG and EndoVIII enzymes to nick dsDNA at dU sites. Right) An HCR polymer bearing additional 3' or 5' toehold displacement domain sequences is disassembled by the introduction of a new DNA strand bearing the full complementary sequence. The dsDNA monomers are washed away.

FIG. 9 is directed to a two cycles of HCR for detection of two target analytes using two orthogonal HCR systems, but only a single spectrally resolvable fluorescence signal. Target 1 is bound by Primary Probe "Alpha", which contains an initiator sequence "i1", and Target 2 is bound by Primary Probe "Beta", which contains an initiator sequence "i2". At Time=1, HCR hairpins cognate to initiator "i1" are added to the sample, and "i1" is contacted by the cognate HCR hairpins forming an HCR polymer, represented by the red star indicating a red fluorescence signal, which is detected. The HCR polymer is subsequently degraded or disassembled or detached at Time=2, thereby returning the sample to a prior state without HCR polymers. At Time=3, HCR hairpins cognate to initiator "i2" are added to the sample, and "i2" is contacted by the cognate HCR hairpins forming an HCR polymer, represented by the red star indicating the same red fluorescence signal, which is detected. The HCR polymer is subsequently degraded or disassembled or detached at Time=4, thereby returning the sample to a prior state without HCR polymers.

According to certain aspects, methods are provided for an HCR polymerization reaction that occurs only at initiator sequences for which the corresponding HCR hairpins are present. FIG. 9 is directed to this, as HCR polymerization at Times 1 and 3 each occur at only one of the two initiator sequences, "i1" and "i2", as in each time point only one set of HCR hairpins cognate to "i1" or "i2" are added. According to certain aspects, an HCR polymerization reaction proceeds in the presence of the initiator sequence, although the initiator sequence may need to be rendered accessible or activated as by Step B. According to certain aspects, the detectable moiety may be added, activated, removed or "reversed" as described herein as in Step D. According to certain aspects, the HCR polymer itself is subject to targeted degradation or disassembly or detachment, constituting programmability of Step C.

Step C may be reversed by targeted degradation or disassembly or detachment of the HCR polymer, i.e. the HCR polymer may be degraded or disassembled or detached. One or more strands of an HCR polymer may be displaced as by DNA toehold strand displacement, as is depicted in FIG. 10B. One or more strands of the HCR polymer may be chemically cleaved, such as by silver nitrate reaction with bridging sulfur phosphorothioate linkages along the DNA backbone, as is depicted in FIG. 10A. One or more strands of the HCR polymer may be enzymatically or chemically degraded, as by lambda exonuclease digestion of a 5'-phosphate bearing DNA strand, ds-specific DNase, or as by USER system (UDG/EndoVIII) or EndoV digestion of DNA containing dU and dI nucleobases, respectively, as is depicted in FIG. 10C. Other enzymes include cas9, zinc finger nucleases, and other targeted endo- and exo-nucleases. The HCR strands may be forced to un-hybridize by incorporating photolabile bases that change atomic configuration upon exposure to certain wavelengths of light. These exemplary methods may or may not remove the initiator itself. To prevent additive signal over rounds of cyclic HCR, methods described above for reversing steps A and B may be used.

Any number of orthogonal Step C strategies may be combined to programmatically render a subset of the HCR polymers as polymerized within a cycle. For example, some polymers may be degraded using chemical methods, while others are simultaneously or serially disassembled using toehold strand displacement.

A Cyclic HCR reaction may not utilize Step C programmability, as in the case where HCR polymers remain intact in a sample after being formed through the HCR polymerization reaction, i.e., the HCR polymer is not removable. Cyclic HCR reactions may still utilize programmability of any of Steps A, B, and D. For example, HCR polymers may be formed in an additive manner over time, but only a subset rendered fluorescent at any one time by use of Step D programmability. Alternatively, the HCR polymers may be formed exactly once, but only a subset rendered fluorescent at any one time by use of Step D programmability.

Step D) Programmable Fluorescent Labeling of HCR Polymer

According to methods described herein, a plurality of target molecules within a sample are detected including the steps of attaching a Primary probe or set of Primary probes to each of a plurality of target molecules, such that at some predetermined time during the Cyclic HCR method, each of the desired plurality of target molecules has a Primary probe or set of Primary probes attached thereto, wherein each Primary probe is functionally linked at some predetermined time to an HCR initiator. HCR monomers, such as hairpin molecules, associated with or unique to an initiator are added and a hybridization chain reaction is carried out as described herein, generating a tethered HCR polymer at the site of the initiator. At some predetermined time, the tether HCR polymer is labeled by one or more, or a plurality of fluorescent or detectable moieties. In this manner, each target molecule within the sample is bound to a probe having an HCR initiator and HCR monomers, such as hairpin molecules are added to detect the target molecule. This process can be conducted in series or in parallel for each target molecule in the sample over time. Each target molecule may be bound to a probe having an HCR initiator, where HCR monomers, such as hairpin molecules are subsequently added to detect the target molecule, one or more times over the course of a Cyclic HCR method. Over the entire course of a Cyclic HCR method, each analyte, or each unique aspect of original information being interrogated, such as a molecular species, molecular quality, or molecular configuration, generates a unique pattern of ordered amplified fluorescence signals via Cyclic HCR. For Cyclic HCR, the fluorescence signal may be degenerate to each target molecule during any cycle of HCR. Programmability of Step D is enabled by methods of programming the HCR polymer with the fluorescence signal, such that fluorescent moieties can be specifically coupled to the HCR polymers and/or specifically removed from the HCR polymers. In this way, within an ordered set of HCR polymerization reactions, the same or a common set of detectable moieties may be used repeatedly.

Programmability of Step D of Cyclic HCR is enabled by materials and methods to specifically associate an HCR polymer with a detectable moiety, such as a fluorescence moiety; materials and methods to specifically remove detectable moieties, such as fluorescence moieties, from an HCR polymer; or both.

Use of a secondary probe, referred to as the Step D Probe, which bears the detectable moiety such as a fluorescent moiety, allows the detectable moiety to be introduced to the HCR polymer, and/or removed from the polymer. This process can be conducted in series or in parallel for each target molecule in the sample wherein the detectable moiety can be the same within and across all set of HCR polymer molecules generated at the target molecules. In this manner a single detectable moiety can be used to detect all of the plurality of target molecules in the sample. The detectable moieties or detectable labels are detected. According to certain aspects, the detectable moieties or detectable labels are removed from the HCR polymer after detection, i.e. the detectable labels are removable. In this manner, the function of the system to detect a target molecule is reversed. According to certain aspects, the constituent HCR monomers, such as hairpins that form the HCR polymer contain a detectable moiety, such as fluorescence moiety, such that the HCR polymer contains a plurality of detectable moieties, such as fluorescence moieties; the HCR polymer is thereby detected; and the detectable moieties or detectable labels are removed from the HCR polymer after detection. In this manner, the function of the system to detect a target molecule is reversed.

Figure 12:
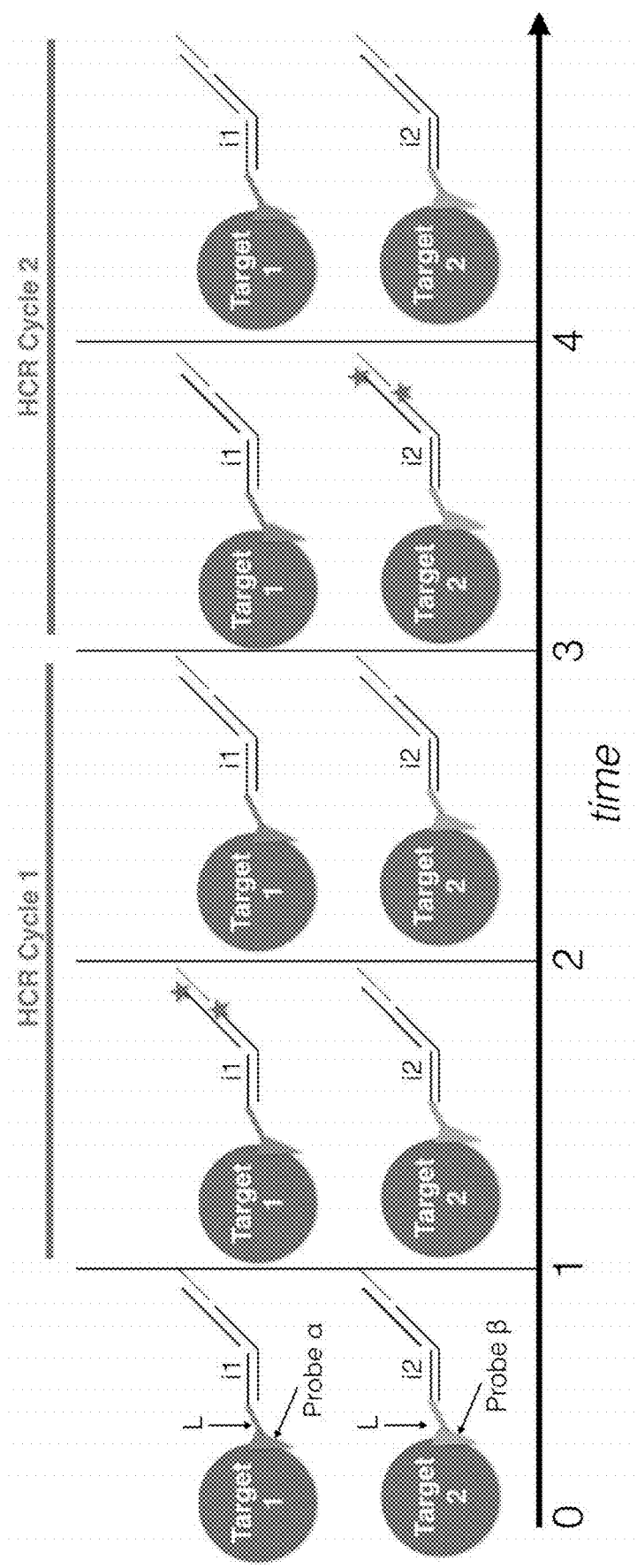
FIG. 12 depicts a schematic of programming Step D, association of a fluorescent moiety to the HCR polymer. At Time=0, two target analytes 1 and 2 are bound by Primary Step A probes "Alpha" and "Beta", respectively, functionally linked to the initiator sequences "i1" and "i2", respectively, via linkers represented as "L", but understood to be any kind of programmable or non-programmable linker as described in Step B of Cyclic HCR. HCR hairpins corresponding to the orthogonal HCR systems initiated by initiators "i1" and "i2" have been added to the sample, and have contacted the initiator sequences "i1" and "i2", which are linked to Primary probes Alpha and Beta, respectively, and formed HCR polymers at the target analytes. At Time=1, the HCR polymer generated by initiator "i1" linked to Probe Alpha has been conjugated to a fluorescent moiety and the fluorescence is detected, thereby detecting target analyte 1. At Time=2, the fluorescent moieties are removed from the HCR polymer. At Time=3, the HCR polymer generated by initiator "i2" linked to Probe Beta has been conjugated to a fluorescent moiety and the fluorescence is detected, thereby detecting target analyte 2. At Time=4, the fluorescent moieties are removed from the HCR polymer. In this example, only a single fluorescent moiety is re-used in serial to label two target analytes. The first cycle of HCR is represented at Time=1 through 2, whereas the second cycle of HCR is represented at Time=3 through 4.

FIG. 12 is directed to two cycles of HCR using Cyclic HCR Step D programmability. Two target analytes are bound by Primary Step A probes "Alpha" and "Beta", respectively, functionally linked to the initiator sequences "i1" and "i2", respectively, via linkers represented as "L", but understood to be any kind of programmable or non-programmable linker as described by Step B of Cyclic HCR. HCR monomer hairpins corresponding to the orthogonal HCR systems initiated by initiators "i1" and "i2" have been added to the sample, and have contacted the initiator sequences "i1" and "i2", which are linked to Primary probes Alpha and Beta, respectively, and formed HCR polymers at the target analyte. In series, each HCR polymer associated with or cognate to initiators "i1" and "i2" are conjugated to a detecting fluorescence moiety, represented by the blue stars. After detection, the fluorescent moiety is removed from the HCR polymer, although the HCR polymer remains intact, thereby returning the sample to a state of no detectable fluorescence signal between cycles of HCR.

Methods and materials enabling the programmable labeling an HCR Polymer include HCR monomer or hairpin molecules having a nucleic acid handle moiety for binding a probe, referred to as the Step D Probe, including a detectable moiety. One or more complementary oligonucleotide Step D probes including one or more detectable moiety or moieties is added to bind to the handles of the HCR polymer; HCR monomer or hairpin molecules having an epitope, which is bound by a ligand referred to as the Step D probe, including one or more detectable moiety. One or more ligand Step D probes including one or more detectable moiety is added to bind to the epitopes of the HCR polymer. HCR monomer or hairpin molecules having a chemical group or handle, for which a chemical or enzymatic reaction can specifically conjugate a detectable moiety onto the HCR polymer; e.g. an accessible 3' OH for addition of a fluorescent dNTP by a terminal transferase; or an accessible 5' phosphate for addition of a fluorescent oligo by a DNA ligase; or bearing a primary amine, for reaction with a fluorophore conjugated to an NHS-ester.

Methods and materials enabling the programmable removal of a detecting moiety, e.g. reversal of the fluorescence labeling of the HCR polymer, include Methods for disrupting the bond between annealed nucleic acids or nucleic acid analogs by means of temperature, salt concentrations, denaturants (urea, formamide, guanidine HCl) to remove a fluorescent Step D probe from the HCR polymer; Step D Probe materials and methods for introducing a photo-labile, chemically-labile, or enzymatically-labile group anywhere in the portion of Step D Probe that binds the HCR polymer, such that the binding is disrupted upon induction, as by light treatment or introduction of a chemical or enzymatic agent, e.g. a photolabile group, which changes conformation upon treatment by UV light altering the conformation of the oligonucleotide to disrupt nucleic acid annealing between the Step D Probe and the HCR polymer; HCR monomer or hairpin materials and methods for introducing a photo-labile, chemically-labile, or enzymatically-labile group anywhere in the portion of the HCR hairpin that binds the Step D Probe, such that the binding is disrupted upon induction, as by light treatment or introduction of a chemical or enzymatic agent, e.g. a photolabile group, which changes conformation upon treatment by UV light altering the conformation of the oligonucleotide to disrupt nucleic acid annealing between the Step D Probe and the HCR polymer; Step D Probe materials and methods for introducing a photo-labile, chemically-labile, or enzymatically-labile group anywhere between the portion of Step D Probe that binds the HCR polymer and the fluorescence or detecting moiety, such that the physical linkage is broken and the fluorescent or detecting moiety can be washed away or removed; e.g. introduction of a 3' or 5' bridging phosphorothioate linkage in the backbone of a DNA oligonucleotide between the region of the Step D probe physically linked to the HCR polymer and the fluorescent or detecting moiety; HCR monomer or hairpin materials and methods for introducing a photo-labile, chemically-labile, or enzymatically-labile group anywhere between the portion of HCR hairpin involved in formation of the HCR polymer and the binding partner of the Step D Probe including the fluorescence or detecting moiety, such that the physical linkage between the polymer and the fluorescence moiety is broken and the fluorescent or detecting moiety can be washed away or removed; e.g. introduction of a 3' or 5' bridging phosphorothioate linkage in the backbone of a DNA oligonucleotide between the region of the HCR hairpin annealed to another HCR hairpin within the HCR polymer and the region containing the binding partner to the Step D Probe containing the fluorescent or detecting moiety; Step D Probe materials and methods for specifically degrading the Step D probe or the portion thereof either containing the fluorescent moiety or responsible for binding to the HCR polymer; e.g. DNase digestion of a DNA Step D probe, where the HCR polymer is protected from the DNase activity by means of a modified base, such that the Step D probe is specifically degraded; HCR monomer or hairpin materials and methods for specifically degrading the binding partner of the Step D Probe, such as enzymatic or chemical digestion of an epitope, cleavage or fragmentation of a nucleic acid handle, such that the binding partner of the Step D Probe is removed from the HCR polymer, thereby allowing the Step D Probe containing the detecting or fluorescence moiety to be removed from the HCR hairpin as by diffusion or washing; Step D probe materials and methods for quenching the fluorescence or detecting moiety, such as photobleaching of a fluorescent moiety to permanently eliminate the fluorescence excitation/emission quality of the detecting moiety; or such as introduction of a secondary Step D probe, which binds to a portion of the primary Step D probe and bears a quenching group.

Figure 13:
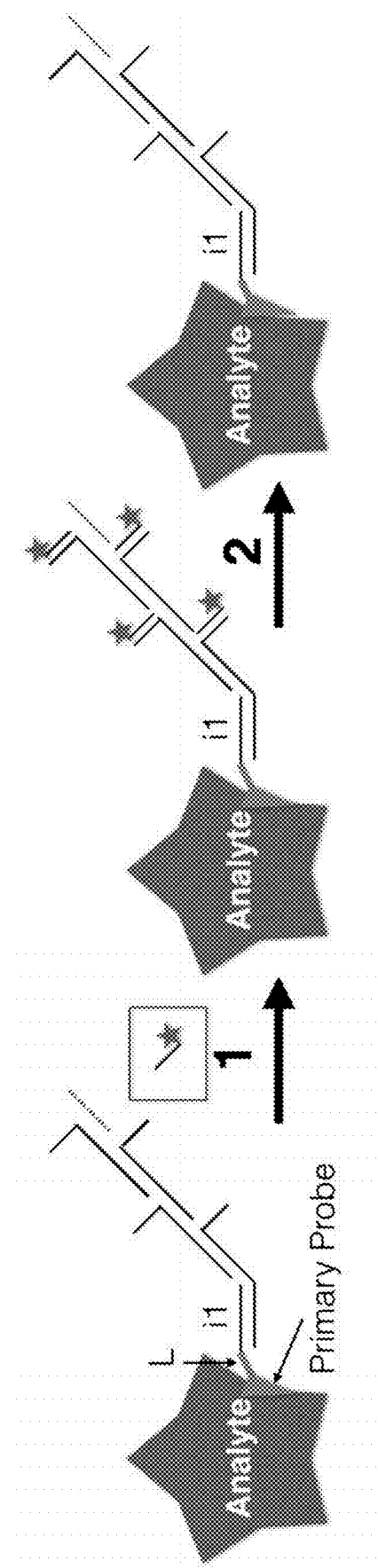
FIG. 13 depicts a schematic of programming Step D of Cyclic HCR. An analyte is bound by a Primary Step A probe, functionally linked to the initiator sequence "i1" via a linker represented as "L", but understood to be any kind of programmable or non-programmable linker as described in Step B of Cyclic HCR. HCR hairpins containing additional handle sequences have been added to the sample, and have contacted the initiator sequence "i1" and formed an HCR polymer at the target analyte. The HCR polymer also contains the additional handles. In Step 1, a fluorescent Step D Probe, which is complementary to the handles of the HCR hairpin, is added to the sample and hybridizes to the handle sequences of the HCR polymer, associating an amplified fluorescence signal to the polymer and by extension to the target analyte, which is detected. In Step 2, the fluorescent Step D Probe is stripped from the HCR polymer or otherwise specifically degraded as described in Step D methods and materials, such that the HCR polymer is no longer fluorescently labeled.
Figure 14A:
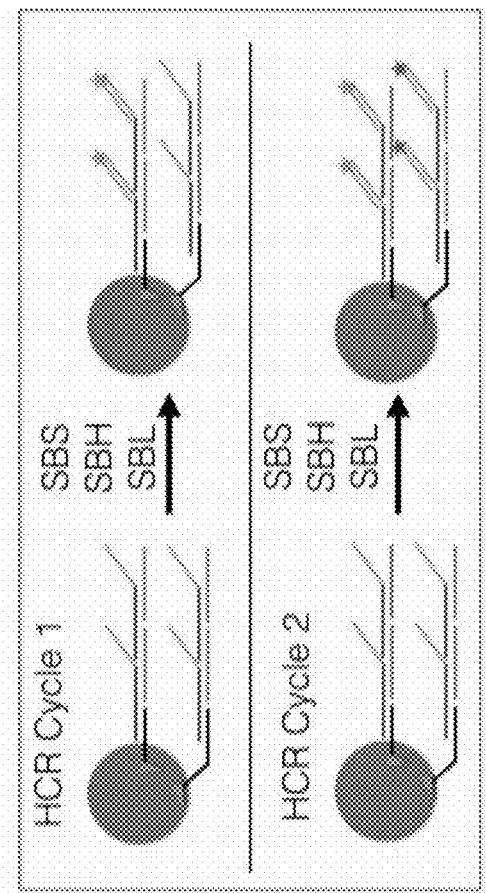
FIGS. 14A-14B depict diagrams of a cyclic fluorescent labeling of HCR polymer using Step D methods and materials.
Figure 14B:
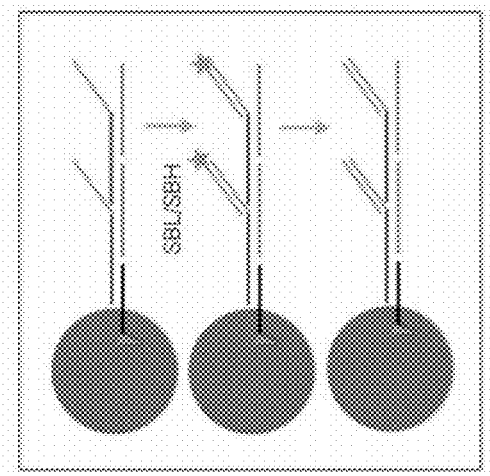
Figure 16:
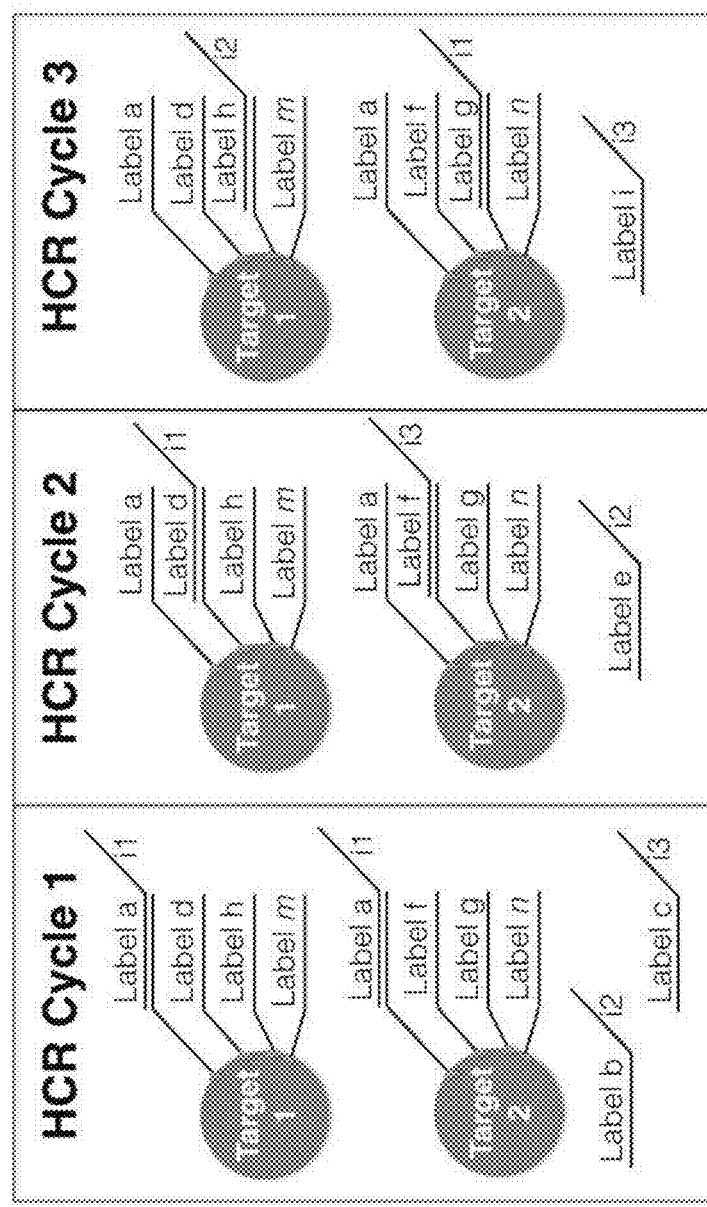
FIG. 16 depicts a diagram of cycles of HCR experiments conducted to the sample depicted in FIGS. 15A, 15C, and 15D. In each round of HCR within the cyclic HCR experiment, the Primary Probe, depicted as an orange triangle, is conjugated to a linker referred to as "Label x", which uniquely refers to the combination of HCR cycle number and HCR system or spectrally distinct fluorescence signal. Step B is programmed by introduction of Step B probes which functionally link the Primary Probe to an HCR initiator sequence, one of the set "i1", "i2", or "i3", as by DNA hybridization. In this example, in each HCR cycle a set of three Step B Probes hybridize to the Primary Probe linkers, adding an initiator sequence. HCR hairpins corresponding to the 3 orthogonal HCR systems are added and contact the initiator, forming an HCR hairpin and amplified fluorescence signal is detected. In this example, each of the three HCR systems can be understood to have a spectrally distinct fluorescence signal. Between subsequent rounds of HCR, Step B is reversed, such that the initiator from the previous cycle is removed from the sample. For each subsequent cycle, new Step B Probes are added to functionally link a distinct set of Primary Probes to one of the three HCR initiators. The three orthogonal HCR systems are re-used in each cycle of HCR. The signals from each cycle are combined into a barcode, which is mapped to a target analyte using Table 5D.

The disclosure provides that an HCR polymer may generate fluorescent signal by fluorescent sequencing by hybridization, sequencing by synthesis, or sequencing by ligation reactions. The fluorescent label may be dissociated or "reversed" by enzymatic or chemical cleavage of the fluorescent moiety from the HCR polymer, or by DNA toehold strand displacement. FIG. 13 is directed to the programming of fluorescence to an HCR polymer by hybridization of a Cyclic HCR Step D Probe to an HCR polymer via an additional handle sequence present on the HCR polymer, and then later stripping the fluorescent Step D Probe from the HCR hairpin after detection of the fluorescence signal. FIG. 14A is directed to additive programming of Cyclic HCR Step D, e.g. only the association of fluorescence with the HCR polymer is programmed, and not the dissociation of fluorescence from the HCR polymer, such that each cycle of Step D adds additional fluorescence signals to the sample. FIG. 14B is directed to programmability of both association and dissociation of fluorescence signal with/from the HCR polymer.

The disclosure provides methods to fluorescently label an HCR polymer by modifying the HCR polymer with additional 5' or 3' handle sequences where a fluorophore-laden oligo, referred to as a Step D Probe, can be hybridized. Alternatively, the handle may serve as a template site for enzymatic sequencing reaction such as sequencing by ligation or sequencing by synthesis using a DNA polymerase to incorporate a fluorescent moiety into a subset of HCR amplicons. For example, in the first cycle, a complementary DNA strand Step D Probe is hybridized to a subset of HCR probe handle sequences, serving as a sequencing primer. A polymerase can be used to incorporate a fluorescent base on that subset of HCR polymers. In subsequent cycles, orthogonal sequencing primers are used to fluorescently label other subsets of the HCR polymer space. In a separate example, a complementary DNA strand Step D Probe is hybridized to a subset of HCR probe handle sequences, serving as a sequencing primer. A polymerase can be used to incorporate a fluorescent base on that subset of HCR polymers. In subsequent cycles, each of the four bases of DNA are used to fluorescently label other subsets of the HCR polymer space, where templated incorporation of each base is directed to a subset of the HCR polymer space. In this example, each fluorescently labeled nucleotide incorporated in series during the sequencing reactions may use a common color of fluorescence.

To dissociate or "reverse" the fluorescent signal, the fluorophore-bearing strand Step D Probe may be displaced as by DNA toehold strand displacement. The fluorescent moiety may be chemically cleaved, such as by silver nitrate reaction with bridging sulfur phosphorothioate linkages along the DNA backbone. The DNA bearing the fluorescent moiety may be enzymatically or chemically degraded, as by lambda exonuclease digestion of a 5'-phosphate bearing DNA strand, ds-specific DNase, or as by USER system (UDG/EndoVIII) or EndoV digestion of DNA containing dU and dI nucleobases, respectively, releasing the fluorophore into solution. Alternatively, the HCR polymer itself may bear functional groups responsible for cycling Step D, as where a chemically-, photo-, or enzymatically-labile group is synthesized into the HCR hairpin between the regions responsible for forming the HCR polymer and the handle or binding moiety for the Step D probe, which contains one or more fluorescent moieties.

In the case where the number N of orthogonal, independent HCR systems is greater than the number of spectrally distinct fluorescent signals f, it is possible to use Step D of Cyclic HCR invention to virtually increase the number of distinct signals by using the temporal domain over k serial cycles of HCR to separate spectrally indistinguishable fluorescent signals. The combined space of k×f is limited only by N. In this implementation, N analytes are labeled with N probes bearing N initiator sequences, and subsequently N HCR hairpin(s) are added to the sample resulting in amplification of N species of HCR polymers, each bearing a unique sequence serving as a handle for hybridization of a fluorescent Step D probe. f Step D probes are introduced in each round of cyclic HCR, each bearing a spectrally distinct fluorophore. The fluorescence signal is detected, and optionally the Step D probe is removed from the HCR polymer or the fluorescence signal is otherwise reversed as described herein. In subsequent cycles of Step D, f Step D probes are introduced, targeting a distinct subset of the N HCR polymers. This method can be used, independently of the other mechanisms described here, to ensure that the number of temporo-spectrally distinct fluorescent signals will always equal N, the number of orthogonal, independent HCR systems. This method can be used for exponential barcoding.

Any number of orthogonal Step D strategies may be combined to programmatically render a subset of the HCR polymers as fluorescently labeled within a cycle. For example, one subset of HCR polymers may be fluorescently labeled by hybridizing a complementary oligonucleotide containing a fluorescent moiety onto a handle feature of the HCR polymer, while another subset of HCR polymers may be fluorescently labeled by binding of a fluorescent moiety conjugated to a streptavidin moiety onto a biotin group attached to the HCR polymer.

A Cyclic HCR reaction may not utilize Step D programmability, as in the case where HCR monomers or hairpins directly contain the fluorescent or detecting moiety, such as by chemical linkage or the fluorophore being directly coupled to the hairpin, or the hairpin containing a fluorescent nucleic acid analog, and are not removable. Cyclic HCR reactions may still utilize programmability of any of Steps A, B, and C. For example, HCR polymers may be directly fluorescent, but still fluorescence is effectively cycled by reversal of HCR polymerization and removal by washing of the fluorescent HCR fragments using methods and materials described herein.

Relationship Between Steps A-D of Cyclic HCR Method

The Steps A-D of the Cyclic HCR method described herein as they relate to the transmission of information throughout the labeling and detection cascade from the original information of the target analyte captured by the binding of a primary probe through to the detection and analysis of fluorescence signals, are conceptually modular, i.e. able to be separated as discrete steps, but may be functionally either modular or coordinated in the actual design and implementation and use of a particular Cyclic HCR method. The performance or reversal of any one step may be coordinated with the performance and/or reversal of one or more other steps of a Cyclic HCR method.

In certain aspects of the invention, reversal of one step of Cyclic HCR effectively reverses other steps. For example, degradation of the HCR polymer into fragments, i.e. reversal of Step C, which are washed from the sample, may effectively remove the associated fluorescence from the sample, effectively reversing Step D as well. As another example, DNase digestion of DNA ISH probes targeting RNA targets may reverse Step A as well as Steps B-C by simultaneous digestion of the HCR initiator and HCR polymer.

Figure 8:
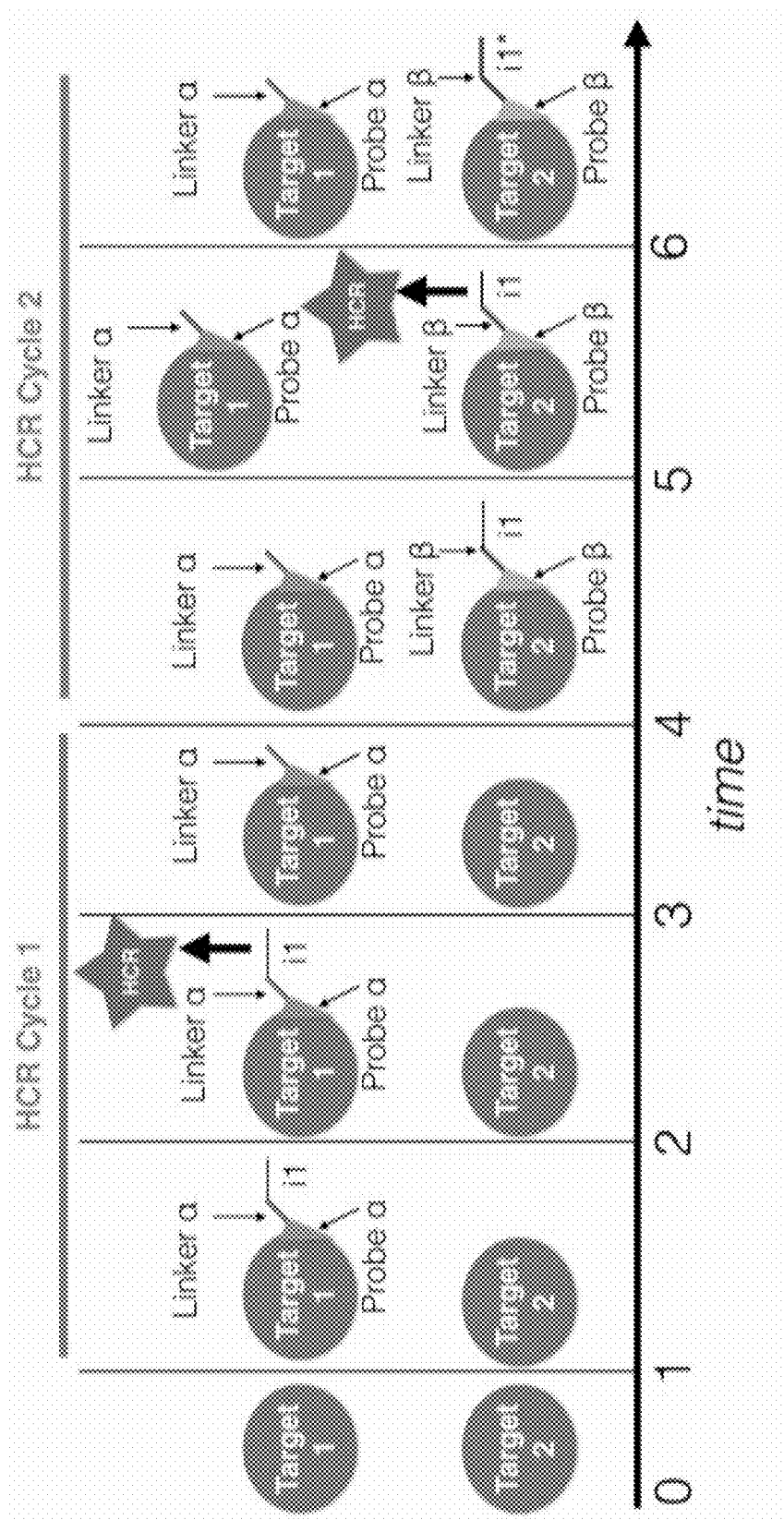
FIG. 8 depicts a Cyclic HCR implementation using Steps A and B. At Time=0, two target analytes are present in the sample. In the first cycle of HCR, depicted as during Times 1 through 3, the first analyte is detected. At Time=1, Target 1 is bound with a Primary Probe "Alpha", which is functionally linked to HCR initiator sequence "i1" via "Linker Alpha", understood to be a covalent linkage or a programmable linkage using the methods described herein in Step B programmability. At Time=2, HCR hairpins cognate to HCR initiator "i1" are added to the sample, and contact initiator "i1"; an HCR polymer is formed and the amplified fluorescence signal is detected. At Time=3, Step B is reversed for Target 1, such as by cleaving the initiator "i1" from the Linker. At this time, Steps C and D are also understood to have been reversed, such that the fluorescence signal detected at Time=2 is no longer present. At Time=4, Step A is iterated to the next cycle by introduction of Primary Probe "Beta", which binds Target analyte 2, and which is functionally linked to HCR initiator sequence "i1" via "Linker Alpha", understood to be a covalent linkage or a programmable linkage using the methods described herein as Step B programmability. At Time=5 HCR hairpins cognate to HCR initiator "i1" are added to the sample, and contact initiator "i1"; an HCR polymer is formed and the amplified fluorescence signal is detected. At Time=6, Step B is reversed for Target 2, as by gating the HCR initiator to an inactive state, "i1*". In this way, Steps A and B are cycled in a coordinated manner for detection of two target analytes.
Figure 19:
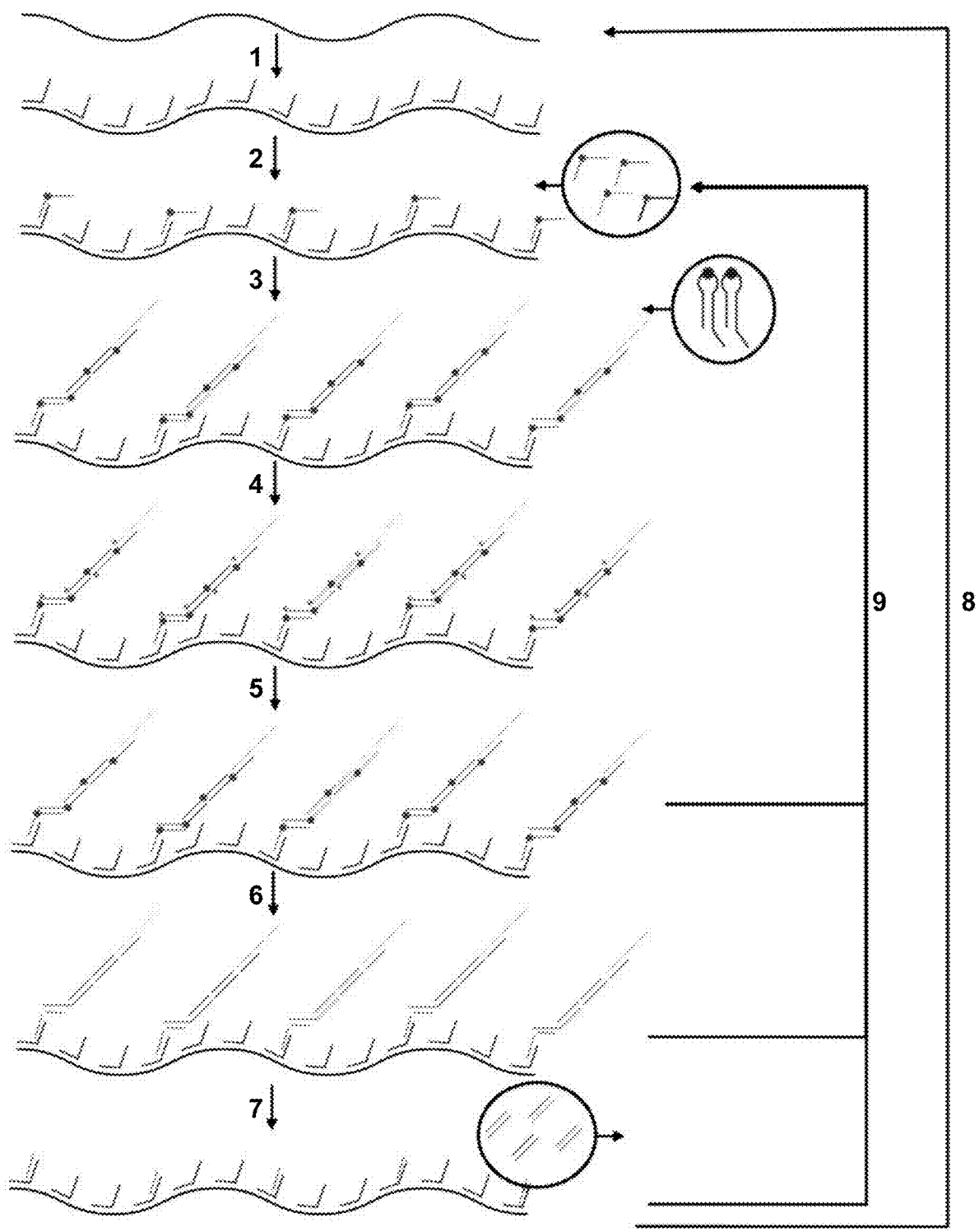
FIG. 19 depicts a schematic of a Cyclic HCR experiment using Steps A-D to detect a target nucleic acid molecule. Step 1 is directed to the introduction and binding of a set of primary ISH probes to the target analyte. Step 2 is directed to establishing a functional link between the HCR initiator and the primary probe, as by introducing and binding Cyclic HCR Step B probes containing sequence complementary to the primary probe and also the HCR initiator. In this diagram, the Cyclic HCR Step B probes contain a cleavable group, represented by the green circles. Step 3 is directed towards introducing HCR hairpins, which contact the initiator and polymerize into tethered nucleic acid polymers known as HCR polymers. In this diagram, the HCR hairpins are modified with a cleavable group, represented by the green circle. Step 4 is directed towards fluorescent labeling of the HCR polymers, with fluorescent moieties represented as orange dots on the polymers. Step 5 is directed towards programming Cyclic HCR Step D by reversing the fluorescent labeling of the HCR polymer. Step 6 is directed to programming Cyclic HCR Steps B and C by cleaving the HCR polymers, as by introduction of a chemical agent that reacts with the cleavable moiety, which also cleaves the HCR initiator from the Primary Probe. Step 7 is directed to washing the HCR polymer fragments from the sample. Step 8 is directed to programming Cyclic HCR Step A by stripping the primary probe from the target analyte, as by digestion of a DNA ISH probe using DNase, which does not digest the RNA target. Step 9 is directed to programming Cyclic HCR Step B, by introducing new sets of Cyclic HCR Step B probes as a precursor to generating new HCR polymers.

In certain aspects of the invention, Cyclic HCR is performed by cycling multiple steps. FIG. 8 is directed to an example of Cyclic HCR using Steps A and B. FIG. 8 depicts two cycles of Step A, using programmable addition of Primary Probes, coordinated with two cycles of Step B, using programmable inactivation or physical separation of the HCR initiator from the Primary Probe. FIG. 19 is directed to an example of Cyclic HCR using the programmability of all four steps of CHCR A-D.

EXAMPLES

The following examples are set forth as being representative of the present disclosure. These examples are not to be construed as limiting the scope of the present disclosure as these and other equivalent embodiments will be apparent in view of the present disclosure, figures and accompanying claims.

Example of Exponential Cyclic HCR Barcoding of RNA: Twenty orthogonal, independent HCR systems exist. The 20 HCR systems are divided into pairs and labeled with one of two spectrally distinct fluorescent colors, such that each pair has both fluorophores, as signals 0 and 1 encoding 10 ordered bits (e.g. the first pair encodes the first bit). A set of 40 smRNA fish probes are designed for each of 1024 genes (e.g. using Biosearch Technologies, Inc. Stellaris RNA FISH probe designer tool). Each gene is assigned a unique 10 bit binary barcode (e.g. 0111010010). Each smRNA fish probe is labeled, according to the gene barcode, on the 5' or 3' end with 3 of the 10 initiator sequences defining the gene barcode. The initiators are distributed equally among the probes for a given gene, such that of the 120 sites per gene (3 sites per probe, 40 probes per gene), each of the 10 values of the barcode is present 12 times. This provides redundancy, such that each value of the barcode can be detected, even if only a fraction of the primary probes are hybridized to the target RNA. All probes are simultaneously hybridized according to standard procedure to a biological sample. The signal is amplified in 10 rounds of CHCR, each cycle detecting two of the 20 labels. After each HCR amplification and imaging, the sample is treated with silver nitrate, chemically cleaving the backbone of the HCR polymers, which are modified with bridging sulfur phosphorothioate modifications, fragmenting the HCR polymers, and fragments are washed from the sample, such that between cycles of CHCR no fluorescence signal is present.

Example of Exponential RNA Barcoding using Eight Cycles of HCR with One Color: A set of 40 smRNA fish probes are designed for each of 100 genes (e.g. using Biosearch Technologies, Inc. Stellaris RNA FISH probe designer tool). Each gene is assigned a unique 8 bit binary barcode (e.g. 01110010). The smRNA fish probes are labeled, according to the gene barode, on the 5' or 3' end with either HCR initiator sequence I1 (=0) or I2 (=1) (Choi et al. *ACS Nano* 8.5: 4284-4294, 2014), corresponding to one of the bits of the barcode. A total of eight pools of probes are synthesized, corresponding to eight cycles of HCR, with the set of probes targeting each gene within each pool containing initiator sequence corresponding to that bit of the barcode, 1-8. The probes are serially hybridized according to standard procedure to a biological sample in 8 cycles, and the signal amplified by DNA HCR sets H1 and H2, which are each modified with an additional handle. After each HCR amplification, in serial, a fluorescent CHCR Step D probe complementary to the handle for each of the two HCR polymer species is hybridized to the sample and imaged, detecting both signals "I1" HCR polymer and "I2" HCR polymer (barcode values 0 and 1, respectively), using only a single fluorescent moiety. The signal is additive between cycles, but the signal from polymer "I1" is computationally subtracted form the signal detected during the second step to generate a new virtual signal corresponding to the "I2" HCR polymer. After detection, the sample is treated with a DNase cocktail to remove the bound ISH probe, HCR initiator sequence, and HCR polymers, which are removed from the sample. The 100 barcodes are assigned within the 255-barcode space ($2^8$-1) to maximize Hamming distance between barcodes, serving as a form of error-detection.

Example of Linear Protein Barcoding: Eight primary antibodies, four each from two host organisms, are purchased, e.g. from Sigma, targeting eight protein targets. Two secondary antibodies capable of recognizing the immunoglobulin of the two primary antibody species, but not cross-reactive, are purchased already conjugated to biotin, such that two streptavidin-modified DNA oligonucleotide containing HCR initiator sequences I1 and I2 can be conjugated to the secondary antibodies, respectively. The primary and secondary antibody staining is done in pairs each containing one of each primary organism, and the signal amplified by the two orthogonal, independent, and spectrally distinct DNA HCR sets H1 and H2. After each HCR amplification and imaging, the sample is treated with formamide, which disrupts the interaction between the antibody and epitope, such that the antibodies and initiators are washed away between each round. (After four cycles, all 8 antibodies have been used.)

Example Protocols of Implementations of Cyclic HCR Experiments

RNA In Situ Hybridization with Cyclic HCR Readout
1. Prepare a biological sample for RNA in situ hybridization
   a. Plate fibroblasts at 30-80% confluence on glass bottom (MATTEK) dish
   b. Grow cells for at least 12 h for attachment
   c. Add 4° C. 4% PFA in PBS+1× RNase Inhibitor, e.g. 2 mM vanadyl ribonucleoside complex (VRC)
   d. Incubate at 37° C. for 10 minutes
   e. To quench fixation add 100 mM glycine in PBS+RNase Inhibitor, e.g. 2 mM VRC
   f. Incubate at 24° C. for 5 minutes
   g. Wash 1× for 1 minute with RNase-free 1× PBS with RNase Inhibitor, e.g. 2 mM VRC
   h. Permeabilize cells with 0.1% Triton-X in RNase-free 1× PBS+RNase Inhibitor, e.g. 2 mM VRC for 30 minutes
   i. Wash twice for 1 minute each with RNase-free 1× PBS with RNase Inhibitor, e.g. 2 mM VRC
   j. Add pre-hybridization buffer 2× Dennhardt's solution+1× RNase-free PBS+RNase Inhibitor, e.g. 2 mM VRC
   k. Incubate for 5 minutes
   l. Add 2 nmol RNA ISH probe pool in 200 uL of hybridization buffer (recipe for 1 mL):
      i. 100 uL 20× SSC
      ii. 300 uL Formamide
      iii. 10 uL RNase Inhibitor, e.g. VRC
      iv. 40 uL 50× Dennhardt's Solution (final 2×)
      v. 200 uL 50% Polyacrylic acid (sodium salt) MW 1000
      vi. 350 uL $H_2O$
   m. Hybridize for 36 hours at 37° C.
2. Prepare sample and HCR reagents for cyclic HCR
   a. Wash sample five times for five minutes each in 2× Sodium Acetate Sodium Citrate buffer with 0.1% Tween-20 (SASCT)
   b. Prepare 30 pmol of each hairpin, modified with dU base incorporations, per cycle of HCR by snap cooling in 10 uL of 5× SASC (heat at 95° C. for 90 seconds and cool to room temperature on benchtop for 30 minutes).

c. Prepare hairpin solution by adding all snap-cooled hairpins to a volume of 5× SASCT of 200 uL per cycle of HCR.
3. Cyclic HCR by mechanisms for Forward Step B and Reverse Steps B & C, for each cycle of HCR:
  a. Hybridize the cycle-subset of linker strands, modified with bridging phosphorothioate, by adding 2.5 uM concentration each linker strand in 2× SSC+30% Formamide+2 mM VRC at 37° C. for 30 minutes
  b. Wash 5× in 2× SSCT for 5 minutes each.
  c. Add hairpin solution to sample and incubate at room temperature for 30 minutes to 16 hours.
  d. Wash 5× in 2× SSCT for 5 minutes each.
  e. Image sample
  f. Add USER reaction as per NEB specification and incubate at 37° C. for 30 minutes to degrade HCR polymer
  g. Add to silver nitrate to final concentration of 50 mM to cleave initiator from the linker probe
  h. Wash 3× in 2× SSCT for 5 minutes each.
  i. Repeat 3 until all subset of linker strands have been used.

Figure 17A:
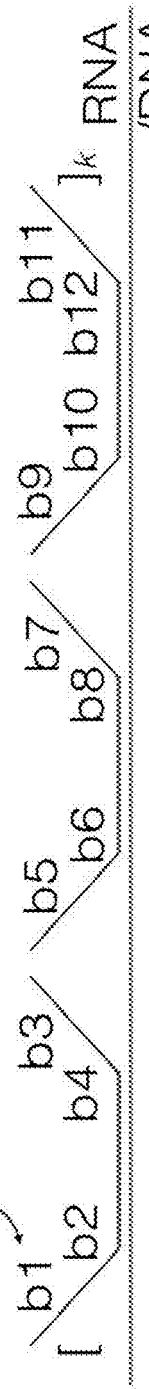
FIGS. 17A-17B depict a diagram of an example of exponential barcoding of a nucleic acid target molecule using Cyclic HCR. A RNA or DNA molecule, shown in green, is targeted and assigned a unique informatic label composed of 24 ordered bits ($2^{24}$). The informatic label is converted into a unique barcode composed of 12 ordered quaternary numerical values, i.e. 12 ordered integers chosen from the set [0, 1, 2, 3]. The barcode is broken into 3 "chunks" of four values, "b1-b4", "b5-b8", and "b9-b12". Each individual quaternary value of, i.e. [0, 1, 2, 3] corresponds with an unique, orthogonal, spectrally resolvable HCR system including initiator sequence and hairpins. At each position in the quaternary barcode string, i.e. "b1" through "b12," four unique sequences are assigned to each possible quaternary value, i.e. [0, 1, 2, 3], for a total of 48 unique sequences referred to as "linkers". The linker sequences are designed to be orthogonal to hybridization under certain reaction conditions, such that a probe complementary to one of the 48 will hybridize specifically with its binding partner and not bind non-specifically with any of the other 47 linker motifs. For the target RNA or DNA, a plurality of primary probes, equal in number to 3k, are designed, containing sequence complementary to the target RNA or DNA sequence (shown in blue). Each primary probe is assigned one of the three chunks of the barcode, such that over the entire pool of primary probes, each label is present k times.
Figure 17B:
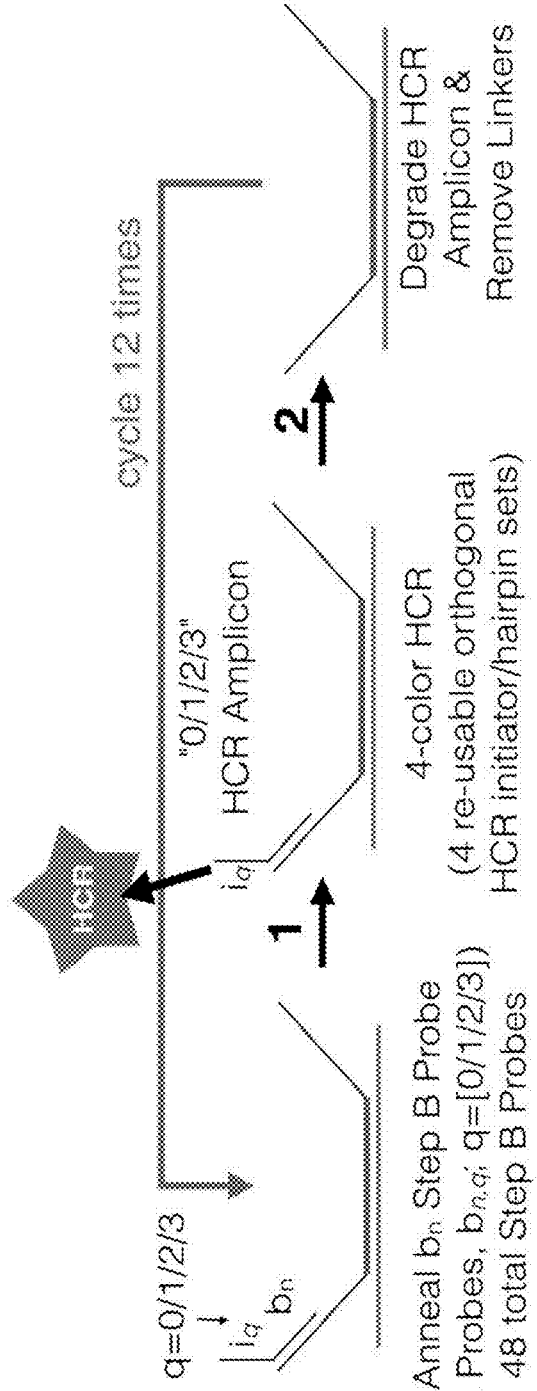

DNA In Situ Hybridization with Cyclic HCR Readout
1. Prepare a biological sample for RNA in situ hybridization
  a. Plate fibroblasts at 30-80% confluence on glass bottom (MATTEK) dish
  b. Grow cells for at least 12 h for attachment
  c. Add 4° C. 4% PFA in 1× DNase-free PBS
  d. Incubate at 37° C. for 10 minutes
  e. To quench fixation add 100 mM glycine in 1× DNase-free PBS
  f. Incubate at 24° C. for 5 minutes
  g. Wash 1× for 1 minute with DNase-free 1× PBS
  h. Permeabilize cells with 0.1% Triton-X in DNase-free 1× PBS
  i. Wash twice for 1 minute each with DNase-free 1×PBS
  j. Wash twice with 2× SSCT+50% formamide
  k. Prepare a hybridization master mix as per Oligopaints (Beliveau, Brian J., Nicholas Apostolopoulos, and Chao-ting Wu. "Visualizing Genomes with Oligopaint FISH probes." *Current Protocols in Molecular Biology* (2014): 14-23 hereby incorporated by reference herein), with Oligopaint design such that each genomic loci is barcoded using 5 HCR signals from a set of 20 orthogonal and independent HCR systems, to be detected with four spectrally distinct fluorescent colors, designed for five cyclic read-outs of 4 HCR polymer sets each. The five HCR initiator sequences constituting the locus barcode are added to the 3' and 5' non-genome-hybridizing arms or handles of the Oligopaints.
  l. Heat the sample slides in 2× SSCT+50% formamide at 92° C. for 2.5 minutes.
  m. Add the Oligopaint probe (20-30 pmol of Oligopaint probe is typically sufficient to produce strong staining in fixed tissue culture cells; 10-fold more probe is recommended for tissue sections and whole mount tissues) in the smallest volume of hybridization master mix capable of covering the sample, and incubate >14 hours at 42° C. in a heated humidified incubator.
2. Prepare sample and HCR reagents for cyclic HCR
  a. Wash the sample with 2× SSCT, then incubate for 15 minutes at 60° C.
  b. Wash the sample four times with 0.2× SSC for five minutes each.
  c. Prepare 30 pmol of each hairpin by snap cooling in 10 uL of 5× SASC (heat at 95° C. for 90 seconds and cool to room temperature on benchtop for 30 minutes). The HCR hairpins are modified with extended handles for interrogation by sequencing by hybridization, e.g. hybridizing a fluorescent probe, such that each independent and orthogonal HCR system has a unique and orthogonal 25 base hybridization site. The hybridization sites can be computationally designed to be mutually orthogonal and orthogonal to the HCR systems, preventing cross-species hybridization, as by use of computational DNA design tools.
  d. Prepare hairpin solution by adding all snap-cooled hairpins to a volume of 5× SASCT of 200 uL per cycle of HCR.
  e. Add the hairpin solution for all 20 HCR sets to the sample and incubate at room temperature for 30 minutes to 16 hours.
  f. Wash 5× in 2× SASCT for 5 minutes each.
3. Cyclic HCR by mechanisms for Forward and Reverse Step D for each cycle of HCR:
  a. For each cycle of HCR read-out, hybridize four probes, each conjugated to a spectrally distinct fluorophore, with an intermediate 3' Thiol-dI base, add probes at 2.5 uM concentration in 2× SASCT for 10 minutes at room temperature
  b. Wash four times in 0.2× SASCT for 5 minutes each
  c. Image
  d. Add silver nitrate to final concentration of 50 mM to cleave the fluorophore from the DNA strand hybridized to the handle of the HCR polymer
  e. Wash four times in 0.2× SASCT for 5 minutes each Additional Embodiments of Exponential Barcoding As shown in FIGS. 17A-17B, which depict an example of exponential barcoding according to the methods of the present disclosure, an RNA or DNA molecule is targeted and hybridized with a plurality of complementary probes, each with one of three 3' and 5' handle motifs. Each probe contains four linker domains, each containing the combined information about the cycle of HCR and HCR initiator. A linker is annealed to the information-bearing domain introducing the initiator sequence, which is used to generate an HCR amplicon and corresponding fluorescent signal. After imaging, the signal is reset using any of the methods described, and the next cycle is performed. Only four orthogonal, independent, spectrally distinct HCR systems are used to generate over 16 million unique barcodes ($4^{12}$) via 4N orthogonal linker domains.

As shown in FIGS. 18A-18D which depict an example of exponential barcoding probe design method according to the present disclosure, in one design of the probe set, where each probe contains a region for targeted hybridization against a target RNA or DNA molecule, and an information-bearing probe sequence containing the combined pairwise information about the cycle of HCR (N) and HCR probe set (k). Here the information-bearing probe is 25 bases long. The set of all probes are designed for 5 cycles of HCR using 4 orthogonal HCR probe sets, requiring 20 orthogonal information-bearing probe sets and giving 1024 possible barcodes. At each cycle of HCR, four Step B probes are added to the sample, which hybridize to the "Label" motif of the primary probe, linking an HCR initiator to the Primary Probe. HCR is used to amplify and detect the fluorescent signal.

Figures 15C, 15D:
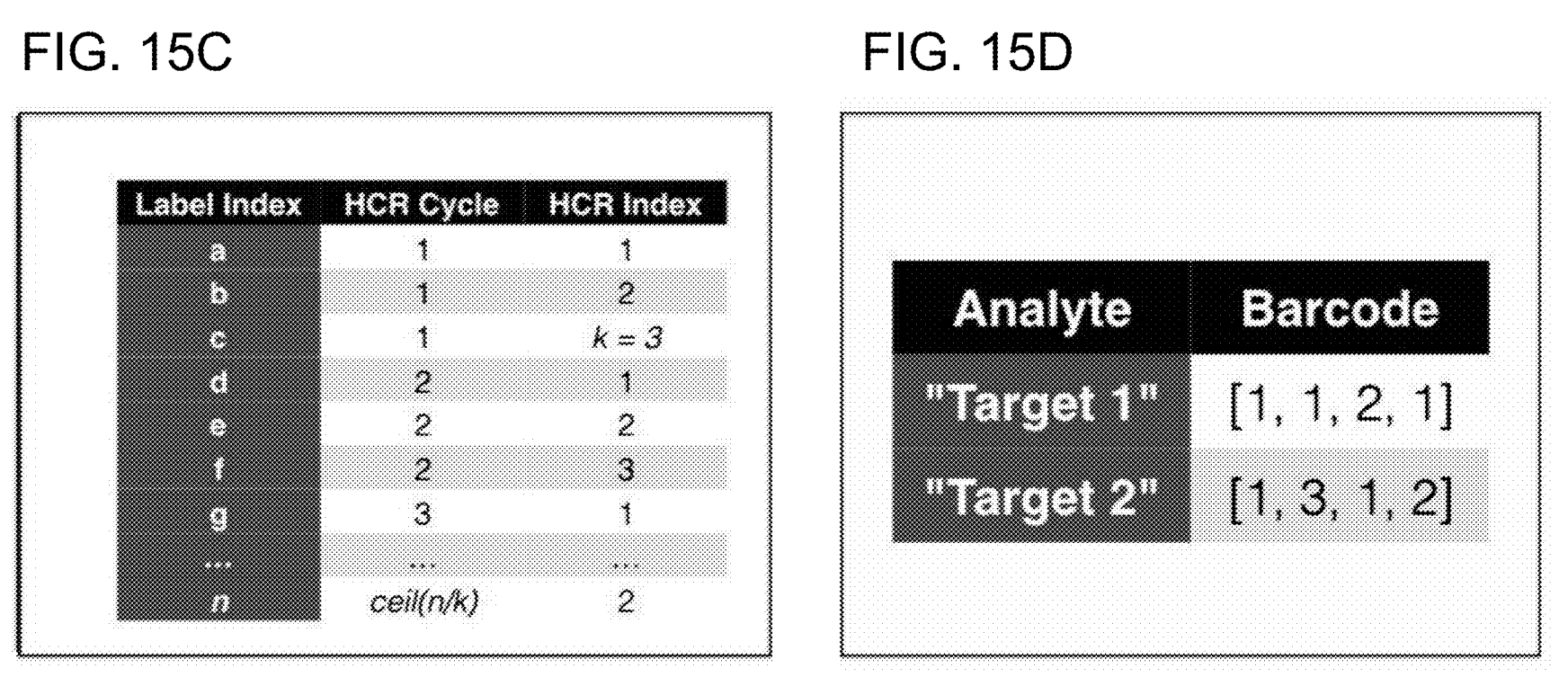

As shown in FIGS. 15A-15D, which depicts an example of exponential barcoding method according to the present disclosure, at the first HCR cycle, three Step B probes are added, linking the information-bearing primary probe sequence to an HCR initiator via the Step B probe motif "Label x", which contains the combined information about the cycle of HCR and the orthogonal and spectrally distinguishable HCR system that will generate the amplified fluorescence polymer. HCR is used to read out the fluorescent signal. As shown in FIG. 15A, the combined set of ordered fluorescence signals may be generated by a plurality of probes at each target molecule, where each primary probe contains only a fraction of the barcode, i.e. the identifier for the original information in the target analyte to be detected specifically via the binding of the primary probe. As shown in FIG. 15B, the combined set of ordered fluorescence signals may be generated by a single probe at each target molecule, where the primary probe contains the entire barcode.

Synthesis Methods for Modified HCR Reagents

Depending on the configuration, a number of possible HCR probe set designs are possible. These probes generally have the features of being an orthogonal set of one or more metastable HCR monomers such as hairpins capable of HCR. The HCR hairpins themselves may be generated by chemical DNA synthesis, as well as enzymatic synthesis. Additional features such as fluorescent labeling and chemistries for programmatically generating and resetting the fluorescence signal are introduced.

Figure 20:
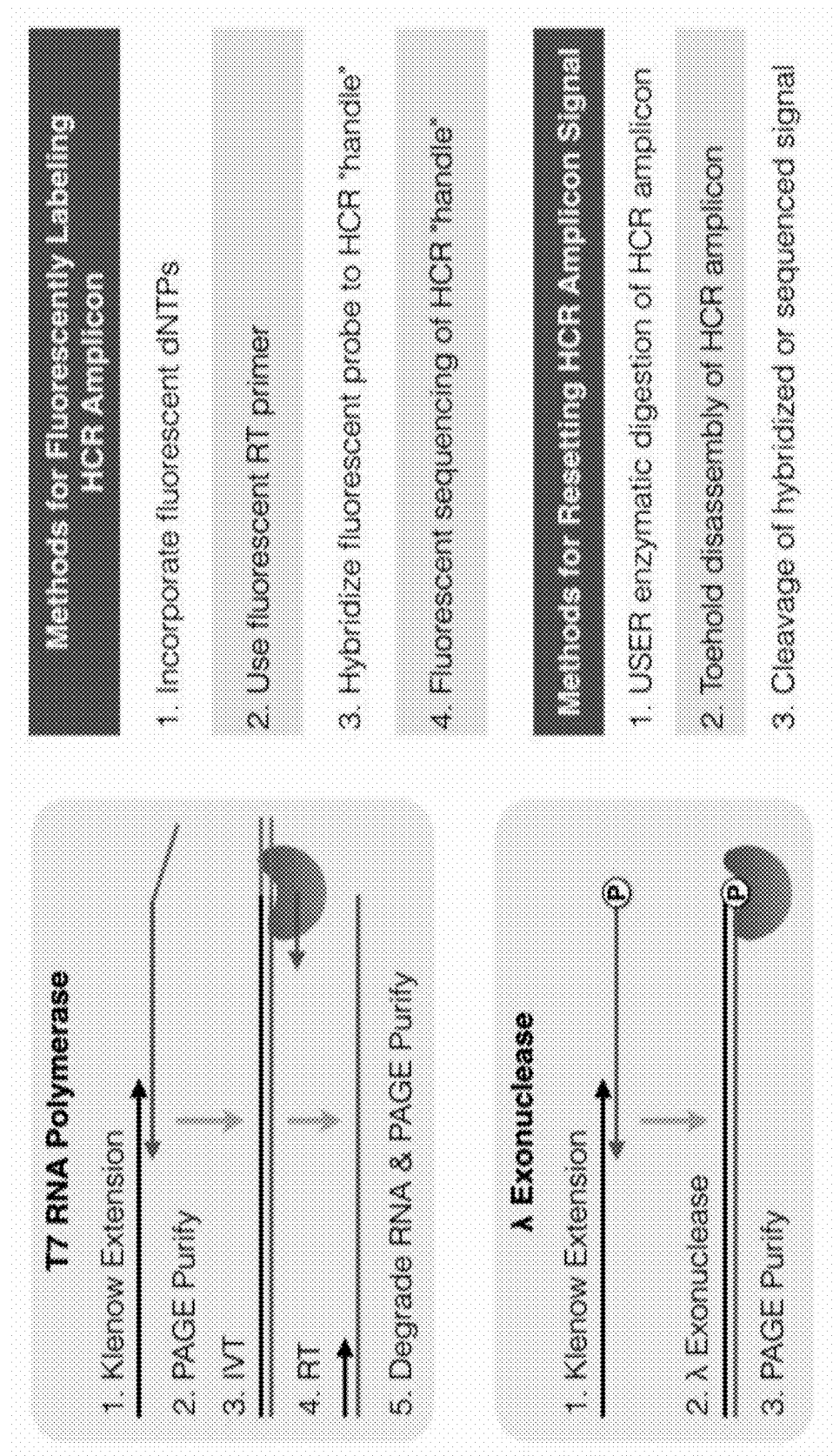
FIG. 20 depicts a schematic overview of methods for synthesizing multiplex HCR hairpins using in vitro transcription or polymerase extension followed by lambda exonuclease digestion to yield single-stranded DNA hairpins.

A schematic overview of methods according the present disclosure for synthesizing multiplex HCR monomers or hairpins is shown in FIG. 20.

HCR labeling strategies I & II.

Figure 21:
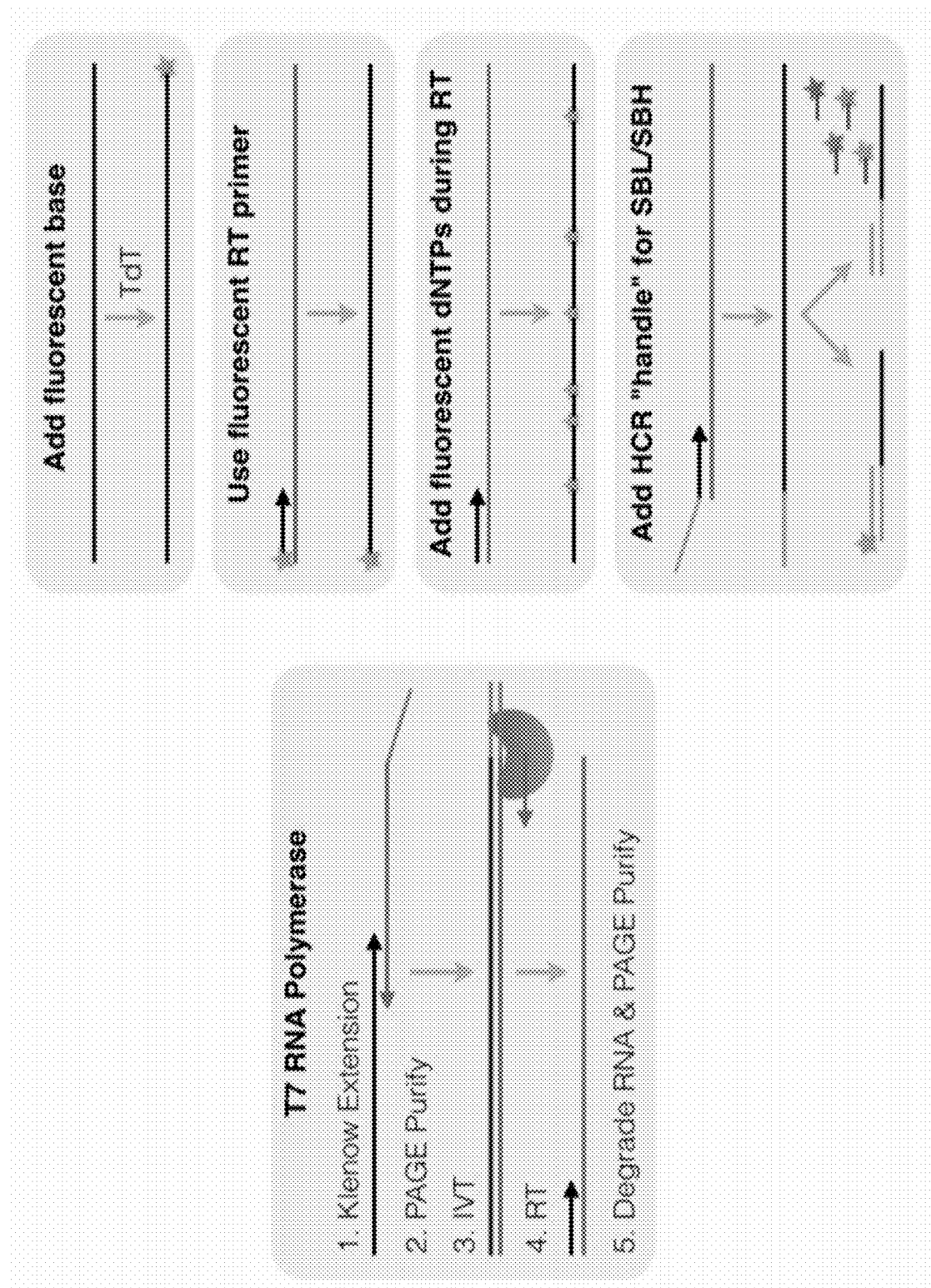
FIG. 21 depicts an HCR labeling strategies I. A dsDNA template is generated through chemical synthesis or chemical synthesis followed by DNA polymerase strand extension. The dsDNA template contains the sequence for the HCR hairpin, as well as any additional sequences such as handles for fluorescent probe hybridization or toehold strand displacement. The dsDNA template contains an RNA polymerase promoter, such as the T7 RNA polymerase promoter sequence. The dsDNA template may also be purified, as by polyacrylamide gel electrophoresis (PAGE). The dsDNA template is used to generate RNA molecules by in vitro transcription (IVT). The RNA may be purified from the dsDNA template. The RNA molecule is used as a template for reverse transcription (RT) to generate a complementary ssDNA molecule. The RNA is degraded and/or the ssDNA is purified and folded into the metastable hairpin. The HCR hairpin is fluorescently labeled in a number of ways, such as by terminal deoxy transferase reaction to add one or more terminal fluorescently-modified DNA bases. The RT primer contains one or more fluorophores, which are incorporated into the resulting ssDNA molecule. Fluorescent DNA bases are incorporated into the ssDNA molecule during reverse transcription. Or, additional sequence is added to the HCR molecule, as during reverse transcription, which serves as a site for fluorescent labeling by sequencing by hybridization (SBH), sequencing by synthesis (SBS), or sequencing by ligation (SBL).

FIG. 21 is directed to an HCR labeling strategy I according to the methods of the present disclosure. A dsDNA template is generated through chemical synthesis or chemical synthesis followed by DNA polymerase strand extension. The dsDNA template contains the sequence for the HCR monomer or hairpin, as well as any additional sequences such as handles for fluorescent probe hybridization or toehold strand displacement. The dsDNA template contains an RNA polymerase promoter, such as the T7 RNA polymerase promoter sequence. The dsDNA template may also be purified, as by polyacrylamide gel electrophoresis (PAGE). The dsDNA template is used to generate RNA molecules by in vitro transcription (IVT). The RNA may be purified from the dsDNA template. The RNA molecule is used as a template for reverse transcription (RT) to generate a complementary ssDNA molecule. The RNA is degraded and/or the ssDNA is purified and folded into the metastable hairpin. The HCR hairpin is fluorescently labeled in a number of ways, such as by terminal deoxy transferase reaction to add one or more terminal fluorescently-modified DNA bases. The RT primer contains one or more fluorophores, which are incorporated into the resulting ssDNA molecule. Fluorescent DNA bases are incorporated into the ssDNA molecule during reverse transcription. Or, additional sequence is added to the HCR molecule, as during reverse transcription, which serves as a site for fluorescent labeling by sequencing by hybridization (SBH), sequencing by synthesis (SBS), or sequencing by ligation (SBL) using methods known to those of skill in the art.

Figure 22:
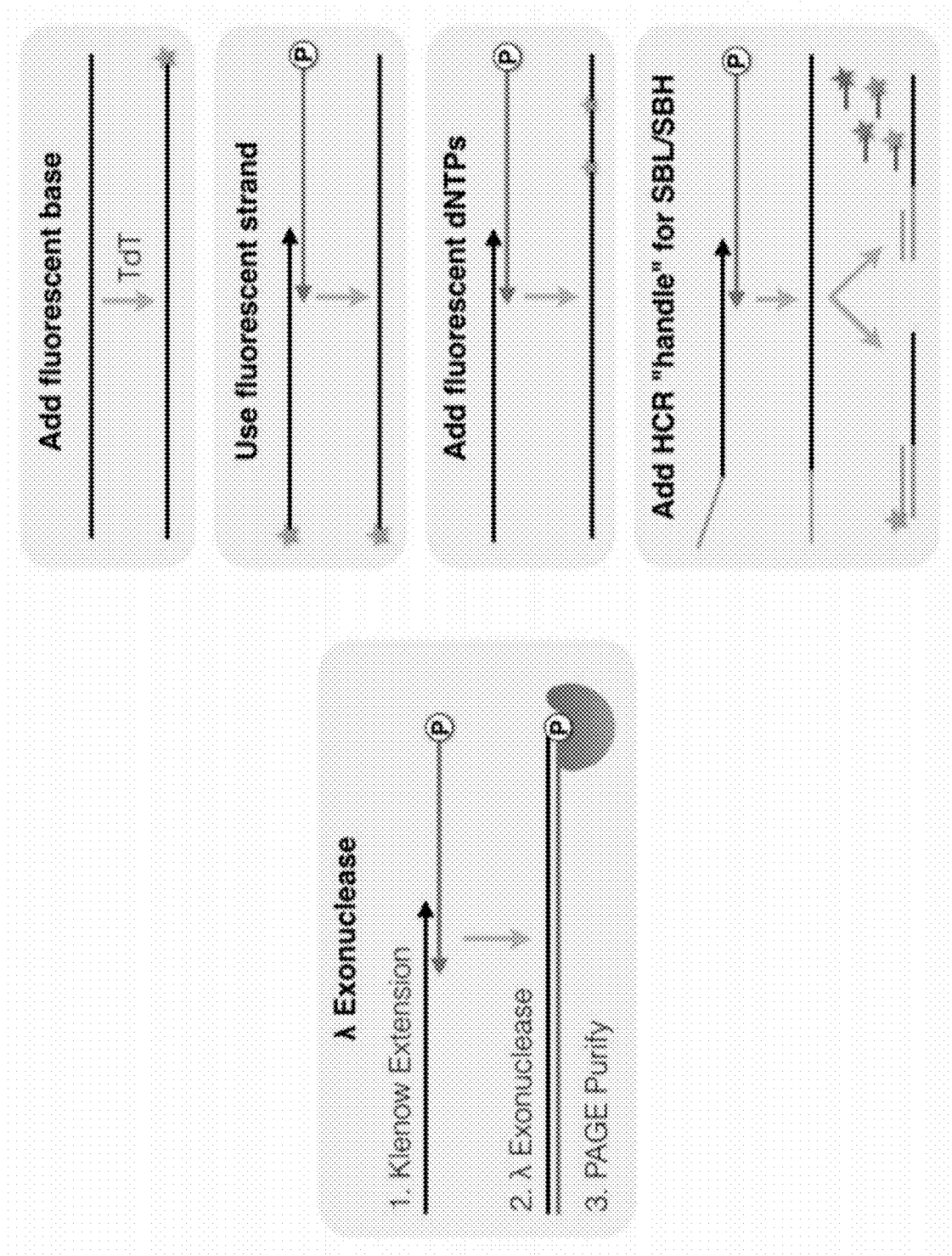
FIG. 22 depicts an HCR labeling strategies II. An ssDNA hairpin is generated by DNA polymerase extension followed by lambda exonuclease digestion of one of the strands of DNA, leaving an ssDNA molecule, which may be purified by PAGE and folded into the HCR hairpin. The HCR hairpin is fluorescently labeled in a number of ways, such as by terminal deoxy transferase reaction to add one or more terminal fluorescently-modified DNA bases. The DNA strand protected from exonuclease digestion may contain one or more fluorophores. Fluorescent DNA bases are incorporated into the ssDNA molecule during polymerase extension. Or, additional sequence is added to the HCR molecule, as during reverse transcription, which serves as a site for fluorescent labeling by sequencing by hybridization (SBH), sequencing by synthesis (SBS), or sequencing by ligation (SBL).
Figure 23:
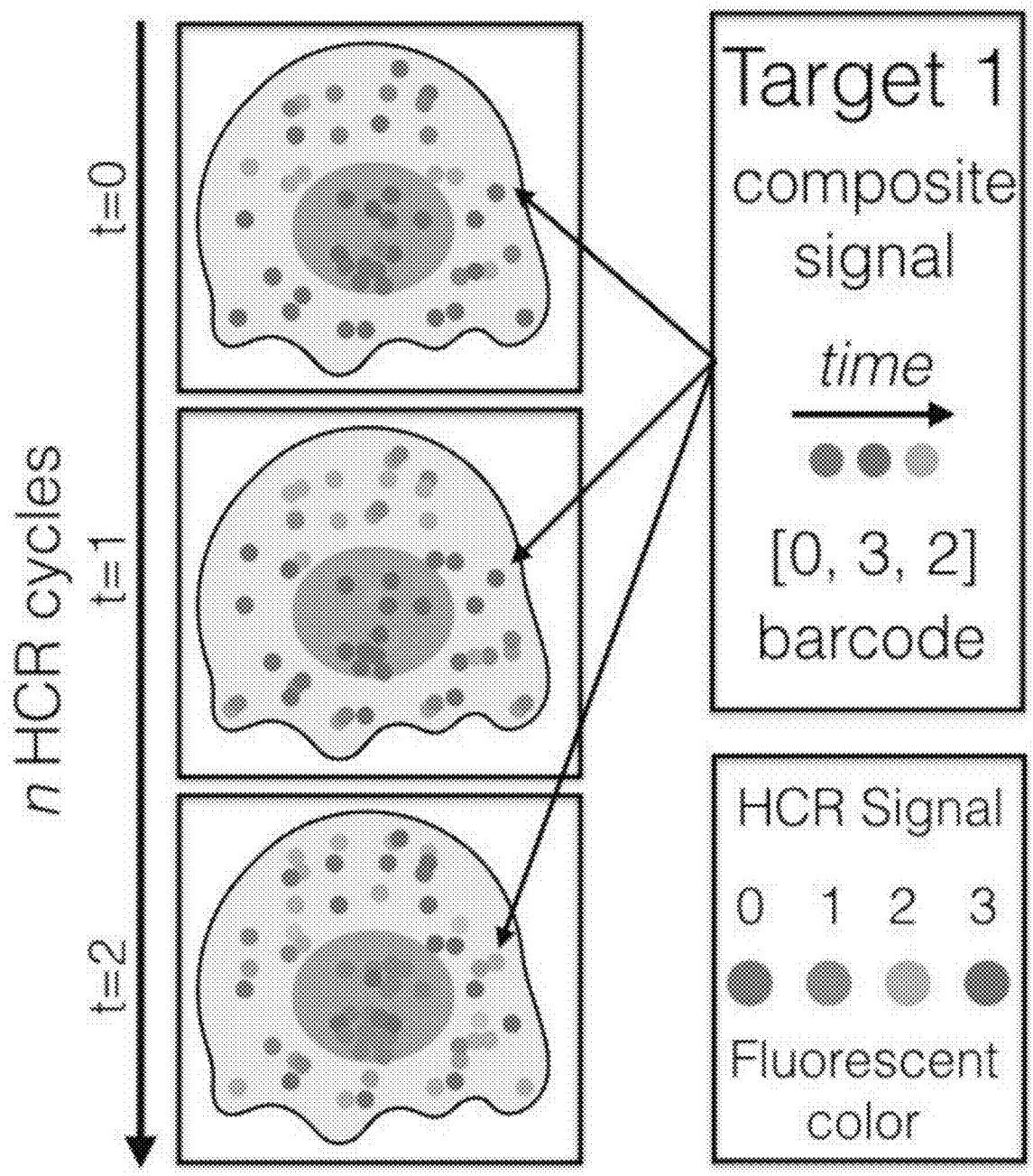
FIG. 23 depicts a schematic of cyclic HCR experimental data from three cycles of Cyclic HCR. The vertical axis depicts the time axis, over which three timepoints corresponding to the three cycles of HCR. Each box depicts a four-color image of a single cell. The four colors correspond to signals from four spectrally resolvable fluorescent moieties cognate to four orthogonal HCR systems, used at each time point of Cyclic HCR. The box labeled "Target 1" depicts the composite label for a particular target analyte, indicated by the arrows connecting the box "Target 1" to the fluorescent HCR signal in each time point. In this depiction, the target analyte 1 is identified by the unique time-ordered composite label, or barcode, [0, 3, 2]. The box "HCR Signal" depicts the four spectrally resolvable fluorescent signals corresponding to the four orthogonal HCR systems, along with the quaternary numerical value associated with each signal. A large number of target analytes are simultaneously detected within the cell. Within each cycle of HCR, the fluorescent signals are degenerate, or not uniquely identifying, but over the totality of HCR cycles, the combined time-ordered composite signal is a unique identifying label for each target analyte. Each target analyte is tracked over time, allowing the signals from each cycle to be combined into the composite label. Each target analyte is identified as a particular molecular species, molecular quality, or molecular configuration. In this way, the spatial localization and spatial distribution of each target analyte can be measured, as well as the abundance of each target analyte.
Figure 24:
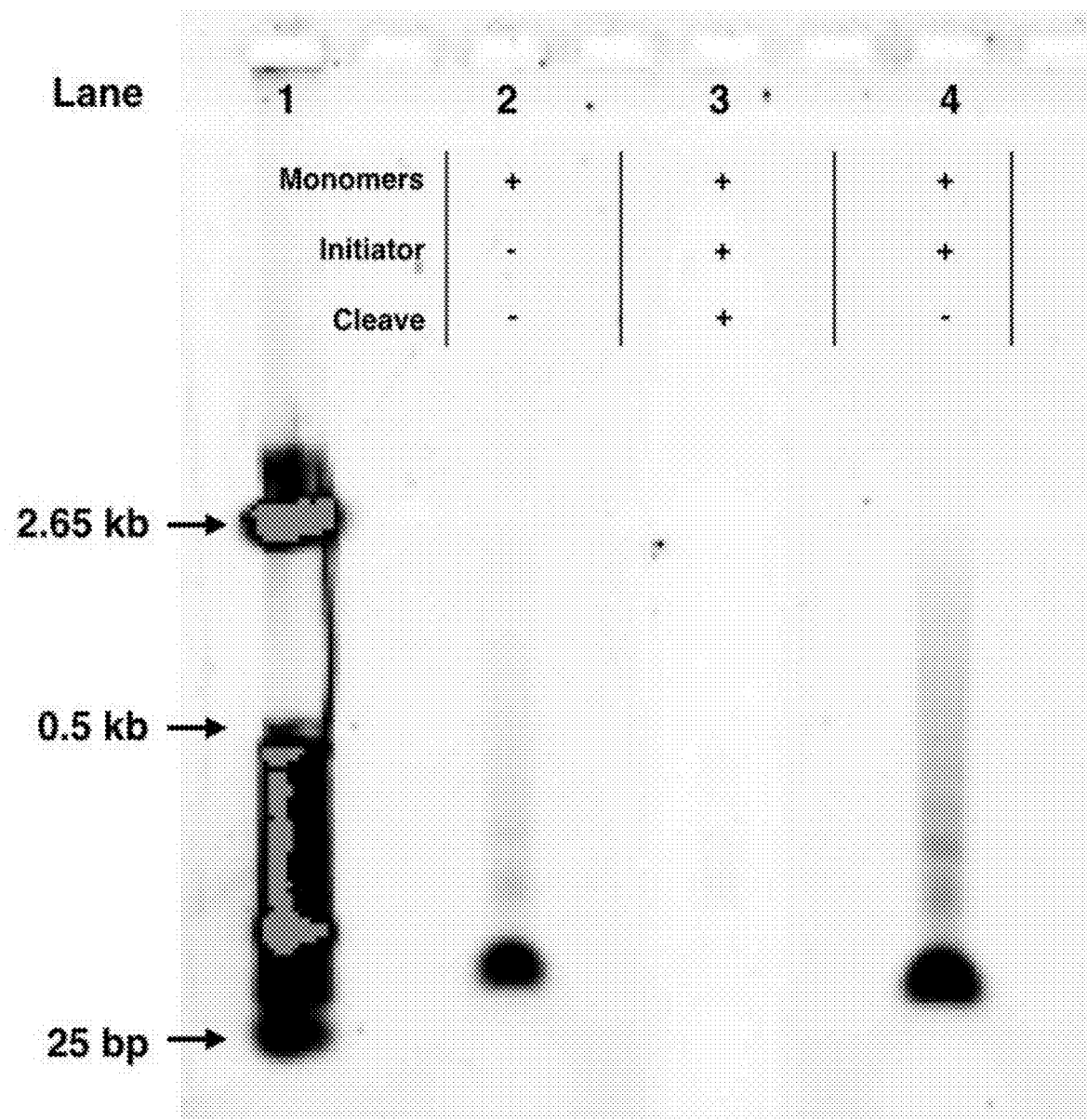
FIG. 24 depicts an in vitro demonstration of the use of modified synthesized HCR reagents, specifically the cleavable HCR monomers for programming Step C of cyclic HCR. This 1% agarose DNA electrophoresis gel shows a size ladder in Lane 1 with size bands corresponding to 25 bp, 0.5 kb, and 2.65 kb indicated by arrows. Lane 2 shows the monomer without initiator and without cleavage demonstrates minimal amplification leakage of the metastable monomers. Lane 3 shows that in the presence of the cleavage reagent, which in the case of these hairpins is silver nitrate, cleaving a bridging phosphorothioate linkage, the hairpins and monomers are degraded and no band is apparent. Lane 4 shows that in the presence of initiator and monomers, but without cleavage reagent, the monomers amplify into larger polymers, seen as the higher molecular weight smearing up to several kilobases in size.

FIG. 22 is directed to an HCR labeling strategy II according to the methods of the present disclosure. An ssDNA hairpin is generated by DNA polymerase extension followed by lambda exonuclease digestion of one of the strands of DNA, leaving a ssDNA molecule, which may be purified by PAGE and folded into the HCR hairpin. The HCR hairpin is fluorescently labeled in a number of ways, such as by terminal deoxy transferase reaction to add one or more terminal fluorescently-modified DNA bases. The DNA strand protected from exonuclease digestion may contain one or more fluorophores. Fluorescent DNA bases are incorporated into the ssDNA molecule during polymerase extension. Or, additional sequence is added to the HCR molecule, as during reverse transcription, which serves as a site for fluorescent labeling by sequencing by hybridization (SBH), sequencing by synthesis (SBS), or sequencing by ligation (SBL).

TABLE 1

Exemplary FISH Probe Set
(Probe set for cyclic HCR against *drosophila melanogaster* gene RNAP II)

| Probe Name | Label ID (Strep B Probe Motif) | Sequence | SEQ ID No. |
|---|---|---|---|
| dros_1_4_Br0 | 0 | ccgaccgaaaagtgtgactg<u>TAT</u>AAATATTCTCGGTACGTACCCCGCC | Seq ID No. 1 |
| dros_2_418_Br4 | 4 | tcatcaggggacaaaatgcc<u>TAT</u>AATGACCTCCGTGCGAGGATTTACT | Seq ID No. 2 |
| dros_3_596_Br8 | 8 | gtcgatgtgtccaaagtgac<u>TAT</u>TTAAAACGGTTTGTCGGCAGCCCAC | Seq ID No. 3 |
| dros_4_673_Br12 | 12 | gagcagtagaagcacacaca<u>TAT</u>AACCATTCATCGCTCCGTCGCCTTA | Seq ID No. 4 |
| dros_5_1031_Br16 | 16 | catgcccagaataaagcact<u>TAT</u>GGAAAAGTCGTTGGCGGGGTTTACG | Seq ID No. 5 |
| dros_6_1149_Br0 | 0 | gcgtcaaatcatcctgattc<u>TAT</u>AAATATTCTCGGTACGTACCCCGCC | Seq ID No. 6 |
| dros_7_1176_Br4 | 4 | ttgccttgatgatatcggac<u>TAT</u>AATGACCTCCGTGCGAGGATTTACT | Seq ID No. 7 |
| dros_8_1483_Br8 | 8 | gttagattctgggcaatgga<u>TAT</u>TTAAAACGGTTTGTCGGCAGCCCAC | Seq ID No. 8 |
| dros_9_1776_Br12 | 12 | acaggttcatgcggaaagtc<u>TAT</u>AACCATTCATCGCTCCGTCGCCTTA | Seq ID No. 9 |
| dros_10_1810_Br16 | 16 | ccgtcgaaatcagcattgta<u>TAT</u>GGAAAAGTCGTTGGCGGGGTTTACG | Seq ID No. 10 |
| dros_11_1983_Br0 | 0 | tgatgaatacgtcgcgcttg<u>TAT</u>AAATATTCTCGGTACGTACCCCGCC | Seq ID No. 11 |
| dros_12_2013_Br4 | 4 | acatgagcagattcatcacc<u>TAT</u>AATGACCTCCGTGCGAGGATTTACT | Seq ID No. 12 |

TABLE 1-continued

Exemplary FISH Probe Set
(Probe set for cyclic HCR against drosophila melanogaster gene RNAP II)

| Probe Name | Label ID (Strep B Probe Motif) | Sequence | SEQ ID No. |
|---|---|---|---|
| dros_13_2303_Br8 | 8 | gtgaccaagttccaggaaac<u>TAT</u>TTAAAACGGTTTGTCGGCAGCCCAC | Seq ID No. 13 |
| dros_14_2355_Br12 | 12 | accaattgttgatcacggtc<u>TAT</u>AACCATTCATCGCTCCGTCGCCTTA | Seq ID No. 14 |
| dros_15_2387_Br16 | 16 | accaataccgatactatggc<u>TAT</u>GGAAAAGTCGTTGGCGGGGTTTACG | Seq ID No. 15 |
| dros_16_2537_Br0 | 0 | cttgttctcgaacgtctgac<u>TAT</u>AAATATTCTCGGTACGTACCCCGCC | Seq ID No. 16 |
| dros_17_2562_Br4 | 4 | gagcatcgtttaggatacgg<u>TAT</u>AATGACCTCCGTGCGAGGATTTACT | Seq ID No. 17 |
| dros_18_2625_Br8 | 8 | ccatagcctttagattgttg<u>TAT</u>TTAAAACGGTTTGTCGGCAGCCCAC | Seq ID No. 18 |
| dros_19_2747_Br12 | 12 | aaagtggggaagagtgcgtt<u>TAT</u>AACCATTCATCGCTCCGTCGCCTTA | Seq ID No. 19 |
| dros_20_2843_Br16 | 16 | acccatagcgtggaaataga<u>TAT</u>GGAAAAGTCGTTGGCGGGGTTTACG | Seq ID No. 20 |
| dros_21_2927_Br0 | 0 | cgactccatagcctttataa<u>TAT</u>AAATATTCTCGGTACGTACCCCGCC | Seq ID No. 21 |
| dros_22_3038_Br4 | 4 | tggcatgttctggaactcaa<u>TAT</u>AATGACCTCCGTGCGAGGATTTACT | Seq ID No. 22 |
| dros_23_3096_Br8 | 8 | cgttgctccagtcaaatttg<u>TAT</u>TTAAAACGGTTTGTCGGCAGCCCAC | Seq ID No. 23 |
| dros_24_3199_Br12 | 12 | gaaaccaaacgatcccactc<u>TAT</u>AACCATTCATCGCTCCGTCGCCTTA | Seq ID No. 24 |
| dros_25_3221_Br16 | 16 | ttgtctcaaactgtcgcgat<u>TAT</u>GGAAAAGTCGTTGGCGGGGTTTACG | Seq ID No. 25 |
| dros_26_3289_Br0 | 0 | tgcacattccagatcatacg<u>TAT</u>AAATATTCTCGGTACGTACCCCGCC | Seq ID No. 26 |
| dros_27_3453_Br4 | 4 | ggattaggcactggaatagc<u>TAT</u>AATGACCTCCGTGCGAGGATTTACT | Seq ID No. 27 |
| dros_28_3545_Br8 | 8 | gaaacgcgtctcgatttctc<u>TAT</u>TTAAAACGGTTTGTCGGCAGCCCAC | Seq ID No. 28 |
| dros_29_3677_Br12 | 12 | acccaatgttacgttctttg<u>TAT</u>AACCATTCATCGCTCCGTCGCCTTA | Seq ID No. 29 |
| dros_30_3719_Br16 | 16 | gggcttttttggatatgttga<u>TAT</u>GGAAAAGTCGTTGGCGGGGTTTACG | Seq ID No. 30 |
| dros_31_3927_Br0 | 0 | gatcaaagtcgggcatttcg<u>TAT</u>AAATATTCTCGGTACGTACCCCGCC | Seq ID No. 31 |
| dros_32_3961_Br4 | 4 | tcaatacgtagcaaccaggg<u>TAT</u>AATGACCTCCGTGCGAGGATTTACT | Seq ID No. 32 |
| dros_33_4120_Br8 | 8 | ttgttctcttcgttgttcat<u>TAT</u>TTAAAACGGTTTGTCGGCAGCCCAC | Seq ID No. 33 |
| dros_34_4184_Br12 | 12 | ctcaatgcagcgcaagaaca<u>TAT</u>AACCATTCATCGCTCCGTCGCCTTA | Seq ID No. 34 |
| dros_35_4287_Br16 | 16 | cagtgatcacgatacgcttc<u>TAT</u>GGAAAAGTCGTTGGCGGGGTTTACG | Seq ID No. 35 |
| dros_36_4355_Br0 | 0 | cactttcatcatcgatgtgc<u>TAT</u>AAATATTCTCGGTACGTACCCCGCC | Seq ID No. 36 |
| dros_37_4534_Br4 | 4 | gtcatcacatcgcacaacag<u>TAT</u>AATGACCTCCGTGCGAGGATTTACT | Seq ID No. 37 |
| dros_38_4784_Br8 | 8 | cgtattgggaatctcgatgc<u>TAT</u>TTAAAACGGTTTGTCGGCAGCCCAC | Seq ID No. 38 |
| dros_39_5257_Br12 | 12 | gagtatcccgatgaagatgg<u>TAT</u>AACCATTCATCGCTCCGTCGCCTTA | Seq ID No. 39 |
| dros_40_5313_Br16 | 16 | caaacgacggactcgactgg<u>TAT</u>GGAAAAGTCGTTGGCGGGGTTTACG | Seq ID No. 40 |
| dros_41_5385_Br0 | 0 | aattggggagtagttggac<u>TAT</u>AAATATTCTCGGTACGTACCCCGCC | Seq ID No. 41 |
| dros_42_5471_Br4 | 4 | cgatgtgggcgaatagcaag<u>TAT</u>AATGACCTCCGTGCGAGGATTTACT | Seq ID No. 42 |
| dros_43_5548_Br8 | 8 | gctgaatagttccggacttgt<u>TAT</u>TTAAAACGGTTTGTCGGCAGCCCAC | Seq ID No. 43 |
| dros_44_5678_Br12 | 12 | tggcgtatattgtggtgatc<u>TAT</u>AACCATTCATCGCTCCGTCGCCTTA | Seq ID No. 44 |
| dros_45_5841_Br16 | 16 | gcgagtagatggacatgttc<u>TAT</u>GGAAAAGTCGTTGGCGGGGTTTACG | Seq ID No. 45 |

TABLE 1-continued

Exemplary FISH Probe Set
(Probe set for cyclic HCR against *drosophila melanogaster* gene RNAP II)

| Probe Name | Label ID (Strep B Probe Motif) | Sequence | SEQ ID No. |
|---|---|---|---|
| dros_46_6084_Br0 | 0 | gcgtagtcggtacttaacta<u>TAT</u>AAATATTCTCGGTACGTACCCCGCC | Seq ID No. 46 |
| dros_47_6283_Br4 | 4 | cttcgaattcgcttttctgg<u>TAT</u>AATGACCTCCGTGCGAGGATTTACT | Seq ID No. 47 |
| dros_48_6595_Br8 | 8 | acatttgtgtgcaggcgaaa<u>TAT</u>TTAAAACGGTTTGTCGGCAGCCCAC | Seq ID No. 48 |

Table 1 contains a set of DNA ISH probes targeting the mRNA *drosophila melanogaster* gene RNAP II for CHCR using Step B. The Lable ID (Step B Probe Motif) refers to the handle sequence complementary to a Step B Probe also containing an HCR initiator. The underlined "TAT" sequence in each Sequence serves as a spacer between the region complementary to the target mRNA (shown in lower case) and the region complementary to the Step B Probe (shown in upper case). The Barcode for this gene is determined by the set of Labels [0, 4, 8, 12, 16], which are converted into a set of ordered fluorescence signals via CHCR, where the relationship between the Label and the HCR signal is determined by the Step B Probe, which functionally links the Primary Probe to the HCR initiator.

TABLE 2

Exemplary Linker Set
(Cleavable linker set between RNAPII probes and HCR initiators)

| Lable ID (Step B Probe Motif) | HCR System | Step B Probe Sequence | Spacer | Linker Oligo Sequence | SEQ ID No. |
|---|---|---|---|---|---|
| 0 | 0 | GGCGGGGTACGTA CCGAGAATATTT | TTXTT | gaggagggcagcaaacgggaagagtcttcctttacg <u>TTXTT</u>GGCGGGGTACGTACCGAGAATATTT | SEQ ID No. 49 |
| 1 | 1 | TAACACGGGAAAC ACTACGGACATT | TTXTT | cctcgtaaatcctcatcaatcatccaagtaaaccgc c<u>TTXTT</u>TAACACGGGAAACACTACGGACATT | SEQ ID No. 50 |
| 2 | 2 | ATGCTAACATCCG GGGTCACCGTAC | TTXTT | gtccctgcctctatatctccactcaactttaacccg <u>TTXTT</u>ATGCTAACATCCGGGGTCACCGTAC | SEQ ID No. 51 |
| 3 | 3 | TAGGCGATCCGTC GTATACTGTACC | TTXTT | cctcaacctacctccaactctcaccatattcgcttc <u>TTXTT</u>TAGGCGATCCGTCGTATACTGTACC | SEQ ID No. 52 |
| 4 | 0 | AGTAAATCCTCGC ACGGAGGTCATT | TTXTT | gaggagggcagcaaacgggaagagtcttcctttacg <u>TTXTT</u>AGTAAATCCTCGCACGGAGGTCATT | SEQ ID No. 53 |
| 5 | 1 | TGCGTTACGAGAT AGCTCGGACCTT | TTXTT | cctcgtaaatcctcatcaatcatccagtaaaccgcc <u>TTXTT</u>TGCGTTACGAGATAGCTCGGACCTT | SEQ ID No. 54 |
| 6 | 2 | GATCTCTGTCCGA CGCACAACCGTT | TTXTT | gtccctgcctctatatctccactcaactttaacccg <u>TTXTT</u>GATCTCTGTCCGACGCACAACCGTT | SEQ ID No. 55 |
| 7 | 3 | GCGCGTTGGGTAA CTTCGACGTCAA | TTXTT | cctcaacctacctccaactctcaccatattcgcttc <u>TTXTT</u>GCGCGTTGGGTAACTTCGACGTCAA | SEQ ID No. 56 |
| 8 | 0 | GTGGGCTGCCGAC AAACCGTTTTAA | TTXTT | gaggagggcagcaaacgggaagagtcttcctttacg <u>TTXTT</u>GTGGGCTGCCGACAAACCGTTTTAA | SEQ ID No. 57 |
| 9 | 1 | ATTGTCCGCCCGG TAAATCAATGAA | TTXTT | cctcgtaaatcctcatcaatcatccagtaaaccgcc <u>TTXTT</u>ATTGTCCGCCCGGTAAATCAATGAA | SEQ ID No. 58 |
| 10 | 2 | GGACTCCGCACGT TCGAGAACACTT | TTXTT | gtccctgcctctatatctccactcaactttaacccg <u>TTXTT</u>GGACTCCGCACGTTCGAGAACACTT | SEQ ID No. 59 |
| 11 | 3 | TTAATTCACTCCA CGCGAACGCGAA | TTXTT | cctcaacctacctccaactctcaccatattcgcttc <u>TTXTT</u>TTAATTCACTCCACGCGAACGCGAA | SEQ ID No. 60 |
| 12 | 0 | TAAGGCGACGGAG CGATGAATGGTT | TTXTT | gaggagggcagcaaacgggaagagtcttcctttacg <u>TTXTT</u>TAAGGCGACGGAGCGATGAATGGTT | SEQ ID No. 61 |
| 13 | 1 | CCACAGGTCAAGT TCGTTAGAACCA | TTXTT | cctcgtaaatcctcatcaatcatccagtaaaccgcc <u>TTXTT</u>CCACAGGTCAAGTTCGTTAGAACCA | SEQ ID No. 62 |
| 14 | 2 | GGACTACGTCGTA AGTCTAACCCTT | TTXTT | gtccctgcctctatatctccactcaactttaacccg <u>TTXTT</u>GGACTACGTCGTAAGTCTAACCCTT | SEQ ID No. 63 |
| 15 | 3 | TTTCGTGCGCAAT CGACTGTGGGAA | TTXTT | cctcaacctacctccaactctcaccatattcgcttc <u>TTXTT</u>TTTCGTGCGCAATCGACTGTGGGAA | SEQ ID No. 64 |
| 16 | 0 | CGTAAACCCCGCC AACGACTTTTCC | TTXTT | gaggagggcagcaaacgggaagagtcttcctttacg <u>TTXTT</u>CGTAAACCCCGCCAACGACTTTTCC | SEQ ID No. 65 |

TABLE 2-continued

Exemplary Linker Set
(Cleavable linker set between RNAPII probes and HCR initiators)

| Lable ID (Step B Probe Motif) | HCR System | Step B Probe Sequence | Spacer | Linker Oligo Sequence | SEQ ID No. |
|---|---|---|---|---|---|
| 17 | 1 | TTGGTGGGACTCC GACCTACAACAA | TTXTT | cctcgtaaatcctcatcaatcatccagtaaaccgcc TTXTTTTGGTGGGACTCCGACCTACAACAA | SEQ ID No. 66 |
| 18 | 2 | CCGCTGTAGTCGT TAGTTGGCAGTT | TTXTT | gtccctgcctctatatctccactcaactttaacccg TTXTTCCGCTGTAGTCGTTAGTTGGCAGTT | SEQ ID No. 67 |
| 19 | 3 | TACTAAGGTAGCC GGACTAGGGTCC | TTXTT | cctcaacctacctccaactctcaccatattcgcttc TTXTTACTAAGGTAGCCGGACTAGGGTCC | SEQ ID No. 68 |

Table 2 contains the Step B Probe sequences corresponding to a plurality of Primary Probes including those listed in Table 1, which target RNAP II. The column "Label ID" refers to the Step B Probe sequence motif complementary to the Primary Probe, and encodes information about both the cycle of CHCR and the HCR signal. "HCR System" refers to which of the four orthogonal HCR systems is associated with each Label ID. "Step B Probe Sequence" refers to the sequence of the Step B Probe that binds the Primary Probe, which is the reverse complement of the sequence contained in the Primary Probe for each Label. "Spacer" is a short sequence designed to spatially isolate the region of the Probe B sequence responsible for binding the Primary Probe with the region containing the HCR initiator. The HCR initiator sequences are found in Table 3. The column "Linker Oligo Sequence" contains the HCR initiator sequence corresponding to the HCR System for that oligo, shown in lower case, combined with the Spacer sequence, shown underlined, combined with the Step B Probe Sequence, shown in upper case. X indicates a 5'Thiol-dI modified base containing a bridging phosphorothioate linkage that can be cleaved using silver nitrate solution.

TABLE 3

Exemplary HCR Initiator Sequences

| HCR System ID | HCR Initiator Sequence | Seq ID No. |
|---|---|---|
| 0 | gaggagggcagcaaacgggaagagtcttcctttacg | Seq ID No. 69 |
| 1 | cctcgtaaatcctcatcaatcatccagtaaaccgcc | Seq ID No. 70 |
| 2 | gtccctgcctctatatctccactcaactttaacccg | Seq ID No. 71 |
| 3 | cctcaacctacctccaactctcaccatattcgcttc | Seq ID No. 72 |

TABLE 4

Exemplary Modified HCR Hairpins
(Sequence for cleavable HCR hairpins using enzymatic and chemical cleavage)
A number of modified HCR hairpin sequences designed for enzymatic
or chemical cleavage. A Key contains references for modified
sequences included within the oligo sequences.

| Name | Sequence | Cycling Method | Seq ID No. |
|---|---|---|---|
| B1H1 Chemical Cleavable | cgtaaaggaagactcttcccgtttgctgccctcctcxcatt ctttcttgaggagggcagcaaacgggaagag | Silver nitrate at Step C | SEQ ID No. 73 |
| B1H2 Chemical Cleavable | gaggagggcagcaaacgggaagagtcttcctttacgxtctt cccgtttgctgccctcctcaagaaagaatgc | Silver nitrate at Step C | SEQ ID No. 74 |
| B1H1 Chemical Cleavable with Fluorophore | cgtaaaggaagactcttcccgtttgctgccctcctcxcatt ctttcttgaggagggcagcaaacgggaagagy | Silver nitrate at Step C | SEQ ID No. 75 |
| B1H2 Chemical Cleavable with Fluorophore | zgaggagggcagcaaacgggaagagtcttcctttacgxtct tcccgtttgctgccctcctcaagaaagaatgc | Silver nitrate at Step C | SEQ ID No. 76 |
| B1H1 USER Cleavable with Fluorophore | cguaaaggaagacucttcccgttugctgccctccucgcatt cttucttgaggagggcagcaaacgggaagagy | USER at Step C | SEQ ID No. 77 |
| B1H2 USER Cleavable with Fluorophore | zgaggagggcagcaaacgggaagagucttccttuacgxtct tcccgtutgctgccctccucaagaaagaaugc | USER at Step C | SEQ ID No. 78 |
| B1H1 Endo V Cleavable with Fluorophore | cgiaaaggaagacicttcccgttigctgccctccicgcatt cttictttgaggagggcagcaaacgggaagagy | Endo V at Step C | SEQ ID No. 79 |

TABLE 4-continued

Exemplary Modified HCR Hairpins
(Sequence for cleavable HCR hairpins using enzymatic and chemical cleavage)
A number of modified HCR hairpin sequences designed for enzymatic
or chemical cleavage. A Key contains references for modified
sequences included within the oligo sequences.

| Name | Sequence | Cycling Method | Seq ID No. |
| --- | --- | --- | --- |
| B1H2 Endo V Cleavable with Fluorophore | zgaggagggcagcaaacgggaagagicttccttiacgctct tcccgtitgctgccctccicaagaaagaaigc | Endo V at Step C | SEQ ID No. 80 |
| B3H1 with Handle Sequence for Toehold Strand Displacement | <u>cagtaaaccgccc</u>gggttaaagttgagtggagatatagagg cagggacaaagtctaatccgtccctgcctctatatctccac tcy | Toehold Strand Displacement at Step C | SEQ ID No. 81 |

Key
X = 5'Thiol-dI
Y = 3' Fluorescent Dye
Z = 5' Fluroescent Dye
U = u (DNA uracil)
I = i (DNA inosine)
Underlined sequence = toehold motif

TABLE 5

Exemplary Sequences for Programmable Fluorescent Labeling of HCR Polymer

| Name | Sequence | Cycling Method | Seq ID No. |
| --- | --- | --- | --- |
| B1H1 with Handle | TCTTCAGCGTTCCCGAGAcacgtaaaggaagactcttcccgtttgc tgccctcctcgcattctttcttgaggagggcagcaaacgggaagag | SBH of Fluorescent Step D Probe | SEQ ID No. 82 |
| B1H2 with Handle | gaggagggcagcaaacgggaagagtcttcctttacgctcttcccgt ttgctgccctcctcaagaaagaatgcTCTTCAGCGTTCCCGAGA | SBH of Fluorescent Step D Probe | SEQ ID No. 83 |
| Fluroescent Step D Probe | TCTCGGGAACGCTGAAGA[3'Thiol-dI][3'DYE] | Silver nitrate reversal of Step D | SEQ ID No. 84 |

Handle sequences for SBH of a fluorescent probe to the HCR polymer for programmable association of fluorescence signal with the HCR polymer shown in upper case. Sequences responsible for HCR polymerization shown in lower case. A cleavable Step D probe is also shown, where the Step D probe can be hybridized to the HCR polymer to associate fluorescence with the polymer, and subsequent to detection, silver nitrate can be added to cleave the fluorescent dye from the Step D probe, returning the HCR polymer to a non-fluorescent state.

The contents of all references, patents and published patent applications cited throughout this application are hereby incorporated by reference in their entirety for all purposes.

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. A method for identifying a plurality of target analytes in a sample, comprising:
   (a) for each target analyte of said plurality of target analytes, contacting said sample with a probe coupled to a linker to bind said probe to said target analyte, wherein said linker is unique to said target analyte;
   (b) subsequently adding a first hybridization chain reaction (HCR) initiator comprising an initiator sequence to said sample and contacting said sample with said first HCR initiator under conditions sufficient to permit said first HCR initiator to bind to said linker, wherein said first HCR initiator is separate from said probe, and wherein upon contacting said sample with said first HCR initiator, said linker couples said probe with said first HCR initiator;

(c) contacting said sample with HCR amplifiers to trigger a hybridization chain reaction, generating a first amplification product coupled to said probe;

(d) detecting said first amplification product;

(e) disrupting or reversing binding between said first HCR initiator and said linker;

(f) contacting said sample with a second HCR initiator comprising a second initiator sequence under conditions sufficient to permit said second HCR initiator to bind to said linker, wherein said second HCR initiator is separate from said probe, and wherein upon contacting said sample with said second HCR initiator, said linker couples said probe with said second HCR initiator;

(g) contacting said sample with additional HCR amplifiers to trigger an additional hybridization chain reaction, thereby generating a second amplification product coupled to said probe;

(h) detecting said second amplification product, and (i) using at least signals from detecting said first amplification product and signals from detecting said second amplification product to generate a combined time-ordered composite signal unique for the each target analyte.

2. The method of claim 1, wherein said disrupting or reversing comprises using toehold displacement to remove said first HCR initiator bound to said linker.

3. The method of claim 1, further comprising generating said first amplification product or said second amplification product in situ.

4. The method of claim 1, further comprising, detecting a spatial localization of said target analyte.

5. The method of claim 1, wherein said probe comprises a protein, a peptide, an aptamer, a deoxyribonucleic acid hybridization probe, a ribonucleic acid hybridization probe, or any combination thereof.

6. The method of claim 1, wherein said probe comprises a nucleotide sequence that is complementary to a sequence of said target analyte.

7. The method of claim 1, wherein said probe comprises an antibody capable of binding to said target analyte.

8. The method of claim 1, wherein said disrupting or reversing comprises using heat or a denaturant to remove said first HCR initiator bound to said linker.

9. The method of claim 1, wherein said disrupting or reversing comprises using chemical, enzymatic, or light treatment that disrupts a linkage between said first HCR initiator and said linker.

10. The method of claim 1, wherein an HCR amplifier of said HCR amplifiers comprises an HCR monomer that comprises a detectable label.

11. The method of claim 10, wherein said detectable label comprises a fluorescent label.

12. The method of claim 10, wherein said detectable label of said HCR monomer comprises a sequencing template for fluorescent sequencing and (d) comprises sequencing said sequencing template by fluorescent sequencing by hybridization, fluorescent sequencing by ligation, or fluorescent sequencing by synthesis.

13. The method of claim 10, wherein said HCR monomer comprises one or more enzymatic or chemical sensitive groups, or photo-labile groups in a DNA backbone of said HCR monomer.

14. The method of claim 2, wherein said toehold displacement comprises using a modified HCR monomer comprising one or more additional sequences for toehold strand displacement.

15. The method of claim 1, wherein said target analyte is associated with a unique plurality of signals comprising signals detected from said first amplification product or said second amplification product.

16. The method of claim 1, wherein said disrupting or reversing comprises cleaving said first HCR initiator.

* * * * *

```
                        SEQUENCE LISTING

<160> NUMBER OF SEQ ID NOS: 104

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
ccgaccgaaa agtgtgactg tataaatatt ctcggtacgt accccgcc                 48

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
tcatcagggg acaaaatgcc tataatgacc tccgtgcgag gatttact                 48

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
gtcgatgtgt ccaaagtgac tatttaaaac ggtttgtcgg cagcccac                 48

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
gagcagtaga agcacacaca tataaccatt catcgctccg tcgcctta                 48

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
catgcccaga ataaagcact tatggaaaag tcgttggcgg ggtttacg                 48
```

```
<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
gcgtcaaatc atcctgattc tataaatatt ctcggtacgt accccgcc                 48

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ttgccttgat gatatcggac tataatgacc tccgtgcgag gatttact                 48

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
gttagattct gggcaatgga tatttaaaac ggtttgtcgg cagcccac                 48

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
acaggttcat gcggaaagtc tataaccatt catcgctccg tcgcctta                 48

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ccgtcgaaat cagcattgta tatggaaaag tcgttggcgg ggtttacg                 48

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tgatgaatac gtcgcgcttg tataaatatt ctcggtacgt accccgcc                 48
```

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthetic probe

<400> SEQUENCE: 12
acatgagcag attcatcacc tataatgacc tccgtgcgag gatttact      48

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic probe

<400> SEQUENCE: 13
gtgaccaagt tccaggaaac tatttaaaac ggtttgtcgg cagcccac      48

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic probe

<400> SEQUENCE: 14
accaattgtt gatcacggtc tataaccatt catcgctccg tcgcctta      48

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic probe

<400> SEQUENCE: 15
accaataccg atactatggc tatggaaaag tcgttggcgg ggtttacg      48

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Synthetic probe

<400> SEQUENCE: 16
cttgttctcg aacgtctgac tataaatatt ctcggtacgt accccgcc      48

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic probe

<400> SEQUENCE: 17
gagcatcgtt taggatacgg tataatgacc tccgtgcgag gatttact      48

<210> SEQ ID NO 18

```
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
ccatagcctt tagattgttg tatttaaaac ggtttgtcgg cagcccac                 48

<210> SEQ ID NO 19
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
aaagtgggga agagtgcgtt tataaccatt catcgctccg tcgcctta                 48

<210> SEQ ID NO 20
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
acccatagcg tggaaataga tatggaaaag tcgttggcgg ggtttacg                 48

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
cgactccata gcctttataa tataaatatt ctcggtacgt accccgcc                 48

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tggcatgttc tggaactcaa tataatgacc tccgtgcgag gatttact                 48

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
cgttgctcca gtcaaatttg tatttaaaac ggtttgtcgg cagcccac                 48

<210> SEQ ID NO 24
<211> LENGTH: 48
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gaaaccaaac gatcccactc tataaccatt catcgctccg tcgcctta            48

<210> SEQ ID NO 25
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
ttgtctcaaa ctgtcgcgat tatggaaaag tcgttggcgg ggtttacg            48

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
tgcacattcc agatcatacg tataaatatt ctcggtacgt accccgcc            48

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ggattaggca ctggaatagc tataatgacc tccgtgcgag gatttact            48

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
gaaacgcgtc tcgatttctc tatttaaaac ggtttgtcgg cagcccac            48

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
acccaatgtt acgttctttg tataaccatt catcgctccg tcgcctta            48

<210> SEQ ID NO 30
<211> LENGTH: 48
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 30 gggcttttg gatatgttga tatggaaaag tcgttggcgg ggtttacg                    48

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
gatcaaagtc gggcatttcg tataaatatt ctcggtacgt accccgcc                   48

<210> SEQ ID NO 32
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
tcaatacgta gcaaccaggg tataatgacc tccgtgcgag gatttact                   48

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
ttgttctctt cgttgttcat tatttaaaac ggtttgtcgg cagcccac                   48

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
ctcaatgcag cgcaagaaca tataaccatt catcgctccg tcgcctta                   48

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
cagtgatcac gatacgcttc tatggaaaag tcgttggcgg ggtttacg                   48

<210> SEQ ID NO 36
<211> LENGTH: 48
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 36
cactttcatc atcgatgtgc tataaatatt ctcggtacgt accccgcc                 48

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
gtcatcacat cgcacaacag tataatgacc tccgtgcgag gatttact                 48

<210> SEQ ID NO 38
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
cgtattggga atctcgatgc tatttaaaac ggtttgtcgg cagcccac                 48

<210> SEQ ID NO 39
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
gagtatcccg atgaagatgg tataaccatt catcgctccg tcgcctta                 48

<210> SEQ ID NO 40
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
caaacgacgg actcgactgg tatggaaaag tcgttggcgg ggtttacg                 48

<210> SEQ ID NO 41
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
aattggggga gtagttggac tataaatatt ctcggtacgt accccgcc                 48

<210> SEQ ID NO 42
<211> LENGTH: 48
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 42
cgatgtgggc gaatagcaag tataatgacc tccgtgcgag gatttact                    48

<210> SEQ ID NO 43
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
gctgaatagt tcggacttgt tatttaaaac ggtttgtcgg cagcccac                    48

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
tggcgtatat tgtggtgatc tataaccatt catcgctccg tcgcctta                    48

<210> SEQ ID NO 45
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
gcgagtagat ggacatgttc tatggaaaag tcgttggcgg ggtttacg                    48

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
gcgtagtcgg tacttaacta tataatatt ctcggtacgt accccgcc                     48

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
cttcgaattc gcttttctgg tataatgacc tccgtgcgag gatttact                    48

<210> SEQ ID NO 48
<211> LENGTH: 48
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 48
acatttgtgt gcaggcgaaa tatttaaaac ggtttgtcgg cagcccac         48

<210> SEQ ID NO 49
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 49
gaggagggca gcaaacggga agagtcttcc tttacgttnt tggcggggta cgtaccgaga    60
atattt                                                              66

<210> SEQ ID NO 50
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 50
cctcgtaaat cctcatcaat catccagtaa accgccttnt ttaacacggg aaacactacg    60
gacatt                                                              66

<210> SEQ ID NO 51
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 51
gtccctgcct ctatatctcc actcaactt aacccgttnt tatgctaaca tccggggtca     60
ccgtac                                                              66

<210> SEQ ID NO 52
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 52
cctcaaccta cctccaactc tcaccatatt cgcttcttnt ttaggcgatc cgtcgtatac    60

```
tgtacc                                                             66

<210> SEQ ID NO 53
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 53
gaggagggca gcaaacggga agagtcttcc tttacgttnt tagtaaatcc tcgcacggag    60
gtcatt                                                             66

<210> SEQ ID NO 54
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 54
cctcgtaaat cctcatcaat catccagtaa accgccttnt ttgcgttacg agatagctcg    60
gacctt                                                             66

<210> SEQ ID NO 55
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 55
gtccctgcct ctatatctcc actcaacttt aacccgttnt tgatctctgt ccgacgcaca    60
accgtt                                                             66

<210> SEQ ID NO 56
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 56
cctcaaccta cctccaactc tcaccatatt cgcttcttnt tgcgcgttgg gtaacttcga    60
cgtcaa                                                             66
```

```
<210> SEQ ID NO 57
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 57
gaggagggca gcaaacggga agagtcttcc tttacgttnt tgtgggctgc cgacaaaccg    60
ttttaa                                                              66

<210> SEQ ID NO 58
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 58
cctcgtaaat cctcatcaat catccagtaa accgccttnt tattgtccgc ccggtaaatc    60
aatgaa                                                              66

<210> SEQ ID NO 59
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 59
gtccctgcct ctatatctcc actcaactttt aacccgttnt tggactccgc acgttcgaga   60
acactt                                                              66

<210> SEQ ID NO 60
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 60
cctcaaccta cctccaactc tcaccatatt cgcttcttnt tttaattcac tccacgcgaa    60
cgcgaa                                                              66

<210> SEQ ID NO 61
<211> LENGTH: 66
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 61
gaggagggca gcaaacggga agagtcttcc tttacgttnt ttaaggcgac ggagcgatga    60
atggtt                                                              66

<210> SEQ ID NO 62
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 62
cctcgtaaat cctcatcaat catccagtaa accgccttnt tccacaggtc aagttcgtta    60
gaacca                                                              66

<210> SEQ ID NO 63
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 63
gtccctgcct ctatatctcc actcaactt aacccgttnt tggactacgt cgtaagtcta    60
accctt                                                              66

<210> SEQ ID NO 64
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 64
cctcaaccta cctccaactc tcaccatatt cgcttcttnt ttttcgtgcg caatcgactg    60
tgggaa                                                              66

<210> SEQ ID NO 65
<211> LENGTH: 66
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 65
gaggagggca gcaaacggga agagtcttcc tttacgttnt tcgtaaaccc cgccaacgac    60
ttttcc                                                              66

<210> SEQ ID NO 66
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 66
cctcgtaaat cctcatcaat catccagtaa accgccttnt tttggtggga ctccgaccta    60
caacaa                                                              66

<210> SEQ ID NO 67
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 67
gtccctgcct ctatatctcc actcaacttt aacccgttnt tccgctgtag tcgttagttg    60
gcagtt                                                              66

<210> SEQ ID NO 68
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 5'Thiol-d-Inosine

<400> SEQUENCE: 68
cctcaaccta cctccaactc tcaccatatt cgcttcttnt ttactaaggt agccggacta    60
gggtcc                                                              66

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gaggagggca gcaaacggga agagtcttcc tttacg                                    36

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cctcgtaaat cctcatcaat catccagtaa accgcc                                    36

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gtccctgcct ctatatctcc actcaacttt aacccg                                    36

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cctcaaccta cctccaactc tcaccatatt cgcttc                                    36

<210> SEQ ID NO 73
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: 5'Thiol-d-Inosine

<400> SEQUENCE: 73
cgtaaaggaa gactcttccc gtttgctgcc ctcctcncat tctttcttga ggagggcagc          60
aaacgggaag ag                                                              72

<210> SEQ ID NO 74
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: 5'Thiol-d-Inosine

<400> SEQUENCE: 74
gaggagggca gcaaacggga agagtcttcc tttacgntct tcccgtttgc tgccctcctc          60

<210> SEQ ID NO 75
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (37)..(37)
<223> OTHER INFORMATION: 5'Thiol-d-Inosine

<400> SEQUENCE: 75
cgtaaaggaa gactcttccc gtttgctgcc ctcctcncat tctttcttga ggagggcagc    60
aaacgggaag ag    72

<210> SEQ ID NO 76
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (37)..(37)
<223> OTHER INFORMATION: 5'Thiol-d-Inosine

<400> SEQUENCE: 76
gaggagggca gcaaacggga agagtcttcc tttacgntct tcccgtttgc tgccctcctc    60
aagaaagaat gc    72

<210> SEQ ID NO 77
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 77
cguaaaggaa gacucttccc gttugctgcc ctccucgcat tcttucttga ggagggcagc    60
aaacgggaag ag    72

<210> SEQ ID NO 78
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 78
gaggagggca gcaaacggga agagucttcc ttuacgctct tcccgtutgc tgccctccuc    60
aagaaagaau gc    72

<210> SEQ ID NO 79
<211> LENGTH: 72

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (14)..(14)
<223> OTHER INFORMATION: Inosine
<220> FEATURE:
<221> NAME/KEY: modified_base
<222> LOCATION: (24)..(24)
<223> OTHER INFORMATION: Inosine
<220> FEATURE:
<221> NAME/KEY: modified_base
<222> LOCATION: (35)..(35)
<223> OTHER INFORMATION: Inosine
<220> FEATURE:
<221> NAME/KEY: modified_base
<222> LOCATION: (45)..(45)
<223> OTHER INFORMATION: Inosine

<400> SEQUENCE: 79
cgnaaaggaa gacncttccc gttngctgcc ctccncgcat tcttncttga ggagggcagc    60
aaacgggaag ag                                                       72

<210> SEQ ID NO 80
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: Inosine
<220> FEATURE:
<221> NAME/KEY: modified_base
<222> LOCATION: (33)..(33)
<223> OTHER INFORMATION: Inosine
<220> FEATURE:
<221> NAME/KEY: modified_base
<222> LOCATION: (47)..(47)
<223> OTHER INFORMATION: Inosine
<220> FEATURE:
<221> NAME/KEY: modified_base
<222> LOCATION: (59)..(59)
<223> OTHER INFORMATION: Inosine
<220> FEATURE:
<221> NAME/KEY: modified_base
<222> LOCATION: (70)..(70)
<223> OTHER INFORMATION: Inosine

<400> SEQUENCE: 80
gaggagggca gcaaacggga agagncttcc ttnacgctct tcccgtntgc tgccctccnc    60
aagaaagaan gc                                                       72

<210> SEQ ID NO 81
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cagtaaaccg cccgggttaa agttgagtgg agatatagag gcagggacaa agtctaatcc    60

```
gtccctgcct ctatatctcc actc                                          84
```

<210> SEQ ID NO 82
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82

```
tcttcagcgt tcccgagaca cgtaaaggaa gactcttccc gtttgctgcc ctcctcgcat   60
tctttcttga ggagggcagc aaacgggaag ag                                 92
```

<210> SEQ ID NO 83
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

```
gaggagggca gcaaacggga agagtcttcc tttacgctct tcccgtttgc tgccctcctc   60
aagaaagaat gctcttcagc gttcccgaga                                    90
```

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (19)..(19)
<223> OTHER INFORMATION: 5'Thiol-d-Inosine

<400> SEQUENCE: 84

```
tctcgggaac gctgaagan                                                19
```

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85

```
ggcggggtac gtaccgagaa tattt                                         25
```

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86

```
taacacggga aacactacgg acatt                                         25
```

<210> SEQ ID NO 87
<211> LENGTH: 25

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
atgctaacat ccggggtcac cgtac                                              25

<210> SEQ ID NO 88
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
taggcgatcc gtcgtatact gtacc                                              25

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
agtaaatcct cgcacggagg tcatt                                              25

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
tgcgttacga gatagctcgg acctt                                              25

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
gatctctgtc cgacgcacaa ccgtt                                              25

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
gcgcgttggg taacttcgac gtcaa                                              25

<210> SEQ ID NO 93
<211> LENGTH: 25
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 93
gtgggctgcc gacaaaccgt tttaa                                               25

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
attgtccgcc cggtaaatca atgaa                                               25

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
ggactccgca cgttcgagaa cactt                                               25

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
ttaattcact ccacgcgaac gcgaa                                               25

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
taaggcgacg gagcgatgaa tggtt                                               25

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
ccacaggtca agttcgttag aacca                                               25

<210> SEQ ID NO 99
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 99
ggactacgtc gtaagtctaa ccctt                                              25

<210> SEQ ID NO 100
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
tttcgtgcgc aatcgactgt gggaa                                              25

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
cgtaaacccc gccaacgact tttcc                                              25

<210> SEQ ID NO 102
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
ttggtgggac tccgacctac aacaa                                              25

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
ccgctgtagt cgttagttgg cagtt                                              25

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
tactaaggta gccggactag ggtcc                                              25
```